(12) United States Patent
Khaled et al.

(10) Patent No.: US 11,179,436 B2
(45) Date of Patent: **\*Nov. 23, 2021**

(54) METHODS AND COMPOSITIONS COMPRISING A C-TERMINAL BAX PEPTIDE

(71) Applicant: University of Central Florida Research Foundation, Inc., Orlando, FL (US)

(72) Inventors: Annette Khaled, Orlando, FL (US); Rebecca Boohaker, Orlando, FL (US); Michael Lee, Orlando, FL (US); Jesus Perez Figueroa, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,004

(22) Filed: Dec. 18, 2018

(65) Prior Publication Data

US 2019/0183965 A1 Jun. 20, 2019

Related U.S. Application Data

(63) Continuation of application No. 14/717,884, filed on May 20, 2015, now Pat. No. 10,159,706, which is a continuation of application No. 14/240,801, filed as application No. PCT/US2012/052354 on Aug. 24, 2012, now Pat. No. 9,040,662.

(60) Provisional application No. 61/645,891, filed on May 11, 2012, provisional application No. 61/527,524, filed on Aug. 25, 2011.

(51) Int. Cl.

| | |
|---|---|
| *A61K 38/10* | (2006.01) |
| *A61K 38/17* | (2006.01) |
| *A61K 38/16* | (2006.01) |
| *A61K 45/06* | (2006.01) |
| *C07K 7/08* | (2006.01) |
| *A01N 43/38* | (2006.01) |
| *A61K 9/51* | (2006.01) |
| *A61P 35/00* | (2006.01) |

(52) U.S. Cl.
CPC ............ *A61K 38/10* (2013.01); *A01N 43/38* (2013.01); *A61K 9/513* (2013.01); *A61K 38/16* (2013.01); *A61K 38/1761* (2013.01); *A61K 45/06* (2013.01); *A61P 35/00* (2018.01); *C07K 7/08* (2013.01); *A61K 9/5153* (2013.01)

(58) Field of Classification Search
CPC ...... A61K 9/5153; A61K 38/10; A61K 38/16; A61K 45/06; A61K 9/513; A61K 38/1761; A01N 43/38; A61P 35/00; C07K 7/08

See application file for complete search history.

(56) References Cited

U.S. PATENT DOCUMENTS

| | | |
|---|---|---|
| 9,040,662 B2 | 5/2015 | Khaled et al. |
| 9,403,888 B2 | 8/2016 | Khaled et al. |
| 2002/0052316 A1 | 5/2002 | Shore et al. |
| 2003/0096367 A1 | 5/2003 | Korsmeyer |
| 2004/0191843 A1 | 9/2004 | Wright et al. |
| 2010/0099742 A1 | 4/2010 | Stassi et al. |
| 2011/0286919 A1 | 11/2011 | Joshi et al. |
| 2014/0178300 A1 | 6/2014 | Pomper et al. |
| 2014/0248210 A1 | 9/2014 | Bradbury et al. |
| 2014/0255299 A1 | 9/2014 | Khaled et al. |
| 2014/0349344 A1 | 11/2014 | Khaled et al. |
| 2015/0004103 A1 | 1/2015 | Borbely et al. |
| 2015/0104387 A1 | 4/2015 | Pomper et al. |

FOREIGN PATENT DOCUMENTS

| | | |
|---|---|---|
| CA | 2846629 | 2/2013 |
| EP | 2747773 | 7/2014 |
| WO | 2013029011 | 2/2013 |
| WO | 2013086430 | 6/2013 |

OTHER PUBLICATIONS

Riedl et al, Membrane-active host defense peptides—Challenges and perspectives for the development of novel anticancer drugs, Chemistry and Physics of Lipids, 2011, 164, pp. 766-781.*
Mulder et al, Current scenario of peptide-based drugs: the key roles of cationic antitumor and antiviral peptides, Front. Microbiol., 2013, 4, pp. 1-23.*
DeVita et al, A History of Cancer Chemotherapy, Cancer Res, 2008, 68, pp. 8643-8653.*
Boohaker et al, Development of a cytotoxic peptide based on the C-terminal domain of Bax, Abstract for the 103rd Annual Meeting of the American Association for Cancer Research held on Mar. 31-Apr. 4, 2012, pp. 1-2.*
Tschammer, Helical Packing Regulates Structural Transitions In Bax, 2007, pp. 1-136.*
Emi et al, Targeted therapy against Bcl-2-related proteins in breast cancer cells, Breast Cancer Research, 2005, 7, pp. R940-R952.*
Mierzwa et al, Recent Advances in Combined Modality Therapy, The Oncologist, 2010, 15, pp. 372-381.*
Cohen, Optimization of Dose-Time Factors for a Tumor and Multiple Associated Normal Tissues, Int. J. Radiat. Oncol. Biol. Phys., 1987, 13, pp. 251-258.*
Garg, Biophysical Characterization of the Membrane Binding Domain of the Pro-apoptotic Protein Bax, Summer Term, 2011, pp. 1-78.*
Tatulian et al, Molecular Basis for Membrane Pore Formation by Bax Protein Carboxyl Terminus, p. 1, Feb. 26, 2012.*

(Continued)

*Primary Examiner* — Li N Komatsu
(74) *Attorney, Agent, or Firm* — Meunier Carlin & Curfman LLC

(57) ABSTRACT

In an aspect, the invention relates to compositions and methods for permeabilizing membranes of cells. In an aspect, the invention relates to compositions and methods for killing cells. In an aspect, the invention relates to compositions and methods of permeabilizing the membranes of cancer cells or microbial cells.

11 Claims, 26 Drawing Sheets

Specification includes a Sequence Listing.

(56) References Cited

OTHER PUBLICATIONS

Antonsson, B., et al. "Bax is present as a high molecular weight oligomer/complex in the mitochondrial membrane of apoptotic cells." J. Biol. Chem., vol. 276, pp. 11615-11623 (2001).
Ausili, A., et al. "The interaction of the bax c-terminal domain with negatively charged lipids modifies the secondary structure and changes its way of insertion into membranes." J. Struct. Biol., vol. 164, pp. 146 (2008).
Barash, S., et al. "Human secretory signal peptide description by hidden markov model and generation of a strong artificial signal peptide for secreted protein expression." Biochem. Biophys. Res. Commun., vol. 463, pp. 835-842 (2002).
Basanez, G., et al. "Bax-type apoptotic proteins porate pure lipid bilayers through a mechanism sensitive to intrinsic monolayer curvature." J. Biol. Chem., vol. 277, pp. 49360 (2002).
Boohaker, R.J., et al. "Bax supports the mitochondrial network, promoting bioenergetics in nonapoptotic cells." Am. J. Physiol. Cell Physiol., vol. 300, pp. C1466-C1478 (2011).
Bovine serum albumin, from http://www.ncbi.nlm.nih.gov/protein/CAA76847.1, pp. 1-2, accessed May 5, 2016.
Brustovetsky, T., et al. "Bax insertion, oligomerization, and outer membrane permeabilization in brain mitochondria: role of permeability transition and SH-redox regulation." Biochem. Biophys. Acta., vol. 1797, pp. 1795-1806 (2010).
Cartron, P.F., et al. "The first alpha helix of bax plays a necessary role in its ligand-induced activation by the BH3-only proteins bid and puma." Mol. Cell, vol. 16(5), pp. 807-818 (2004).
Cartron, P.F., et al. "Distinct domains control the addressing and the insertion of bax into mitochondria." J. Biol. Chem., vol. 280, pp. 10587-10598 (2005).
Cartron, P.F., et al. "The expression of a new variant of the pro-apoptotic molecule bax, baxpsi, is correlated with an increased survival of glioblastoma multiforme patients." Hum. Mol. Genet., vol. 11, pp. 678 (2002).
Cartron, P.F., et al. "The n-terminal end of bax contains a mitochondrial-targeting signal." J. Biol. Chem., vol. 278, pp. 11633 (2003).
Deng, J., et al. "BH3 profiling identifies three distinct classes of apoptotic blocks to predict response to ABT-737 and conventional chemotherapeutic agents." Cancer Cell, vol. 12, pp. 171 (2007).
Del Martinez-Senac, M., et al. "Conformation of the c-terminal domain of the pro-apoptotic protein bax and mutants and its interaction with membranes." Biochemistry, vol. 40, pp. 9983-9992 (2001).
Er, E., et al. "Control of bax homodimerization by its carboxyl terminus." J. Biol. Chem., vol. 282, pp. 24938 (2007).
Eskes, R., et al. "Bax-induced cytochrome c release from mitochondria is independent of the permeability transition pore but highly dependent on mg2+ ions." J. Cell Biol., vol. 143, pp. 217-224 (1998).
European Office Action issued in EP Application No. 15821541.8, dated Feb. 23, 2018.
Garcia-Saez, A.J., et al. "Membrane-insertion fragments of bcl-x1, bax, and bid." Biochemistry, vol. 43, pp. 10930 (2004).
Garcia-Saez, A.J., et al. "Peptides corresponding to helices 5 and 6 of bax can independently form large lipid pores." FEBS J., vol. 273, pp. 971 (2006).
Garcia-Saez, A.J., et al. "Peptides derived from apoptotic bax and bid reproduce the poration activity of the parent full-length proteins." Biophys. J., vol. 88, pp. 3976 (2005).
Garcia-Saez, A.J., et al. "Permeabilization of the outer mitochondrial membrane by bcl-2 proteins." Adv. Exp. Med. Biol., vol. 677, pp. 91-105 (2010).
Gavathiotis, E., et al. "Bax activation is initiated at a novel interaction site." Nature, vol. 455(7216), pp. 1076-1081 (2008).
Geisse, S., et al. "Recombinant protein production by transient gene transfer into mammalian cells." Methods Enzymol., vol. 463, pp. 223-238 (2009).
George, N.M., et al. "Bax contains two functional mitochondrial targeting sequences and translocates to mitochondria in a conformational change- and homo-oligomerization-driven process." J. Biol. Chem., vol. 285, pp. 1384 (2010).
Ghibelli, L., et al. "Multistep and multitask bax activation." Mitochondrion, vol. 10, pp. 604-613 (2010).
Han, S-X, et al. "Secretory transactivating transcription-apoptin fusion protein induces apoptosis in hepatocellular carcinoma hepg2 cells." World Journal of Gastroenterology, vol. 14(23), pp. 3642-3649 (2008).
Horie, C., et al. "Characterization of signal that directs c-tail-anchored proteins to mammalian mitochondrial outer membrane." Mol. Biol. Cell, vol. 13, pp. 1615-1625 (2002).
International Preliminary Report on Patentability dated Apr. 22, 2014 for International Patent Application No. PCT/US2012/052354, which was filed on Aug. 24, 2012 and published as WO 2013/029011 on Feb. 28, 2013 (Inventor—Khaled // Applicant—University of Central Florida Research Foundation, Inc.) (pp. 1-13).
International Preliminary Report on Patentability dated Jun. 10, 2014 for International Patent Application No. PCT/US2012/068590, which was filed on Dec. 7, 2012 and published as WO 2013/086430 on Jun. 13, 2013 (Inventor—Khaled // Applicant—University of Central Florida Research Foundation, Inc.) (pp. 1-9).
International Search Report and Written Opinion dated Apr. 23, 2013 for International Patent Application No. PCT/US2012/068590, which was filed on Dec. 7, 2012 and published as WO 2013/086430 on Jun. 13, 2013 (Inventor—Khaled // Applicant—University of Central Florida Research Foundation, Inc.) (pp. 1-13).
International Search Report and Written Opinion dated Feb. 1, 2013 for International Patent Application No. PCT/US2012/052354, which was filed on Aug. 24, 2012 and published as WO 2013/029011 on Feb. 28, 2013 (Inventor—Khaled // Applicant—University of Central Florida Research Foundation, Inc.) (pp. 1-17).
International Search Report and Written Opinion issued in International Application No. PCT/US2015/39806, dated Dec. 4, 2015, 12 pages.
International Search Report and Written Opinion issued in International Application No. PCT/US2016/29804, dated Aug. 25, 2016, 15 pages.
Jiang et al, Synthesis and Characterization of an Amphiphilic Hyperbranched Poly(amine-Ester)-co-D,L-lactide (HPAE-co-PLA) Copolymers and Their Nanoparticles for Protein Drug Delivery, Journal of Applied Polymer Science, 2010, 117, pp. 1156-1167.
Kaufmann, T., et al. "Characterization of the signal that directs bcl-x(1), but not bcl-2, to the mitochondrial outer membrane." J. Cell Biol., vol. 160, pp. 53-64 (2003).
Kelekar, A., et al. "Bcl-2-family proteins: the role of the bh3 domain in apoptosis." Trends in Cell Biol., vol. 8(8), pp. 324-330 (1998).
Krauson et al, Determining the mechanism of membrane permeabilizing peptides: Identification of potent, equilibrium pore-formers, Biochimica et Biophysica Acta, 2012, pp. 1625-1632.
Leber, B., et al. "Embedded together: the life and death consequences of interaction of the bcl-2 family with membranes." Apoptosis, vol. 12, pp. 897-911 (2007).
Lee et al, The CT20 peptide causes detachment and death of metastatic breast cancer cells by promoting mitochondrial aggregating and cytoskeletal disruption, Cell Death Dis, May 22, 2014, 5:e1249, p. 6, col. 2; p. 7, col. 1; p. 10, col. 2.
Li et al, Interaction of procyanidin B3 with bovine serum albumin, RSC Adv., 2014, 4, pp. 7301-7312.
Lu et al, Alkaloids Isolated from Natural Herbs as the Anticancer Agents, Evidence-Based Complementary and Alternative Medicine, 2012, pp. 1-12.
Nechushtan, A., et al. "Conformation of the bax c-terminus regulates subcellular location and cell death." EMBO J., vol. 18, pp. 2330-2341 (1999).
Non-Final Office Action issued in U.S. Appl. No. 15/327,353, dated Jun. 4, 2018.
Office Action issued in U.S. Appl. No. 15/327,353, dated Jan. 25, 2019.
Advisory Action issued in U.S. Appl. No. 15/327,353, dated Mar. 14, 2019.
Oltersdorf, T., et al. "An inhibitor of bcl-2 family proteins induces regression of solid tumours." Nature, vol. 435, pp. 677-681 (2005).

(56) References Cited

OTHER PUBLICATIONS

Oltvai, Z.N., et al. "Bcl-2 heterodimerizes in vivo with a conserved homolog, bax, that accelerates programmed cell death." Cell, vol. 74, pp. 609-619 (1993).
Preliminary Amendment filed Jun. 7, 2014 for U.S. Appl. No. 14/363,793, filed Jun. 7, 2014 (Inventor—Khaled // Applicant—University of Central Florida Research Foundation, Inc.) (pp. 1-6).
Putcha, G.V., et al. "Bax translocation is a critical event in neuronal apoptosis: regulation by neuroprotectants, BCL-2 and caspases." J. Neurosci., vol. 19, pp. 7476-7485 (1999).
Robertson, J.D., et al. "Outer mitochondrial membrane permeabilization: an open-and-shut case?" Cell Death Differ., vol. 10, pp. 485-487 (2003).
Roucou, X., et al. "Bax oligomerization in mitochondrial membranes requires tbid (caspase-8-cleaved bid) and a mitochondrial protein." Biochem. J., vol. 368, pp. 915-921 (2002).
Santra, S., et al. "Aliphatic hyperbranched polyester: a new building block in the construction of multifunctional nanoparticles and nanocomposites." Langmuir, vol. 26, pp. 5364 (2010).
Schinzel, A., et al. "Conformational control of bax localization and apoptotic activity by pro168." J. Cell Biol., vol. 164, pp. 1021-1032 (2004).
Schlesinger, P.H., et al. "The bax pore in liposomes." Biophysics, Cell Death Differ., vol. 13, pp. 1403-1408 (2006).
Singh et al, Nanoparticle-based targeted drug delivery, Experimental and Molecular Pathology, 2009, 86, pp. 215-223.
Suzuki, M., et al. "Structure of bax: coregulation of dimer formation and intracellular localization." cell, vol. 103, pp. 645-654 (2000).
Tait, S.W., et al. "Mitochondria and cell death: outer membrane permeabilization and beyond." Nat. Rev. Mol. Cell. Biol., vol. 11, pp. 621-632 (2010).
Valero, J.G., et al. "Bax-derived membrane-active peptides act as potent and direct inducers of apoptosis in cancer cells." J. Cell Sci., vol. 124, pp. 556-564 (2011).
Vishnubhotla et al., Chaperonin-containing T Complex (CCT) is a novel target for treatment of metastatic breast cancer, J Clin Oncol, Abstract, Jun. 2015, Abstract only.
Water, from http://www.biology-online.org/dictionary/Water, pp. 1-3, accessed Apr. 24, 2014.
Westphal, D., et al. "Molecular biology of bax and bak activation and action." Biochim. Biophys. Acta, vol. 1813, pp. 521-531 (2011).
Wolter, K.G., et al. "Movement of bax from the cytosol to mitochondria during apoptosis." J. Cell Biol., vol. 139, pp. 1281-1292 (1997).
Youle, R.J., et al. "The bcl-2 protein family: opposing activities that mediate cell death." Nat. Rev. Mol. Cell. Biol., vol. 9, pp. 47-59 (2008).
Zhang, L., et al. "Role of bax in the apoptotic response to anticancer agents." Science, vol. 290, pp. 989 (2000).
Zhang, L., et al. "Role of bax in the apoptotic response to anticancer agents." Science, vol. 290, pp. 989-992 (2000).
Zhou, L., et al. "Dynamics and structure of the bax-bak complex responsible for releasing mitochondrial proteins during apoptosis." J. Cell Sci., vol. 121, pp. 2186-2196 (2008).
First Examination Report issued in Australian Application No. 2015290058 dated Mar. 6, 2020, 4 pages.
Office Action dated Sep. 10, 2019, from related Canadian Application No. 2,846,629, 6 pages.

* cited by examiner

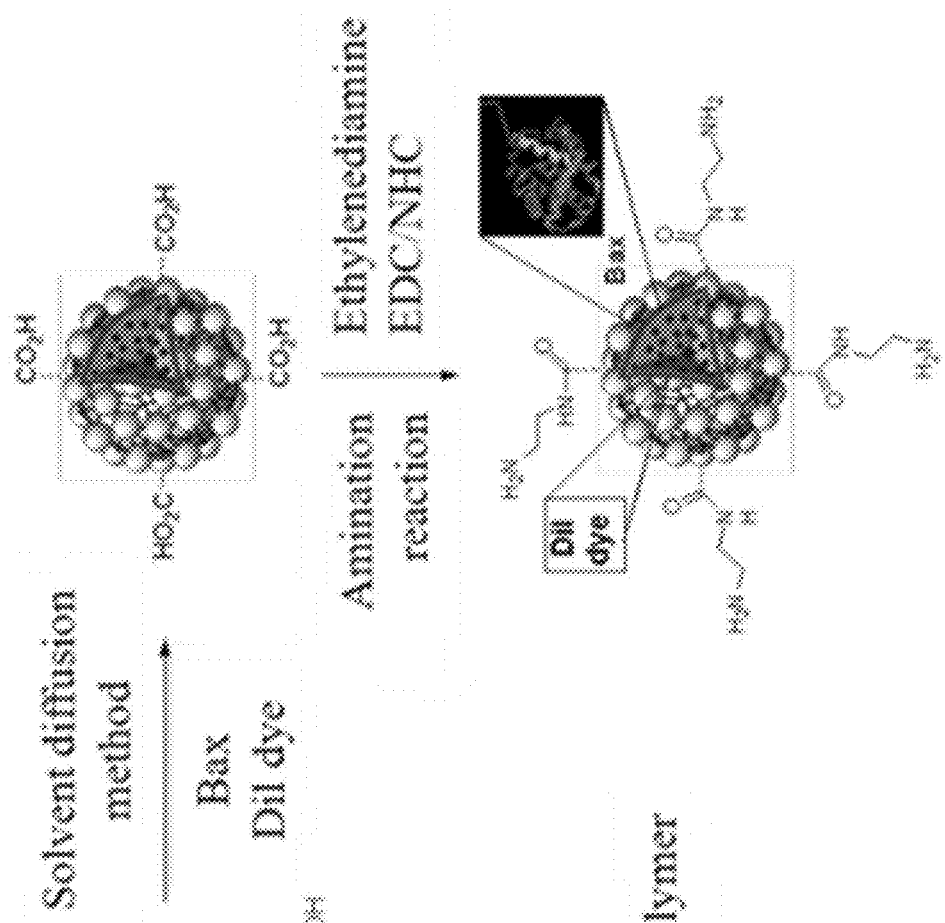
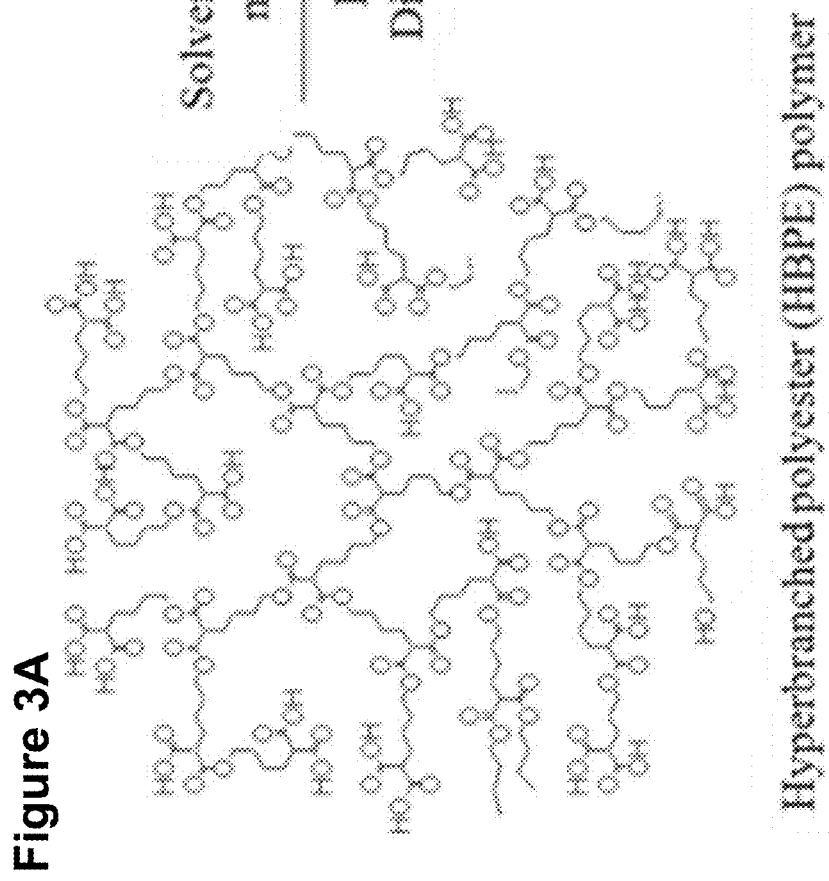
Figure 3A

Figure 3C
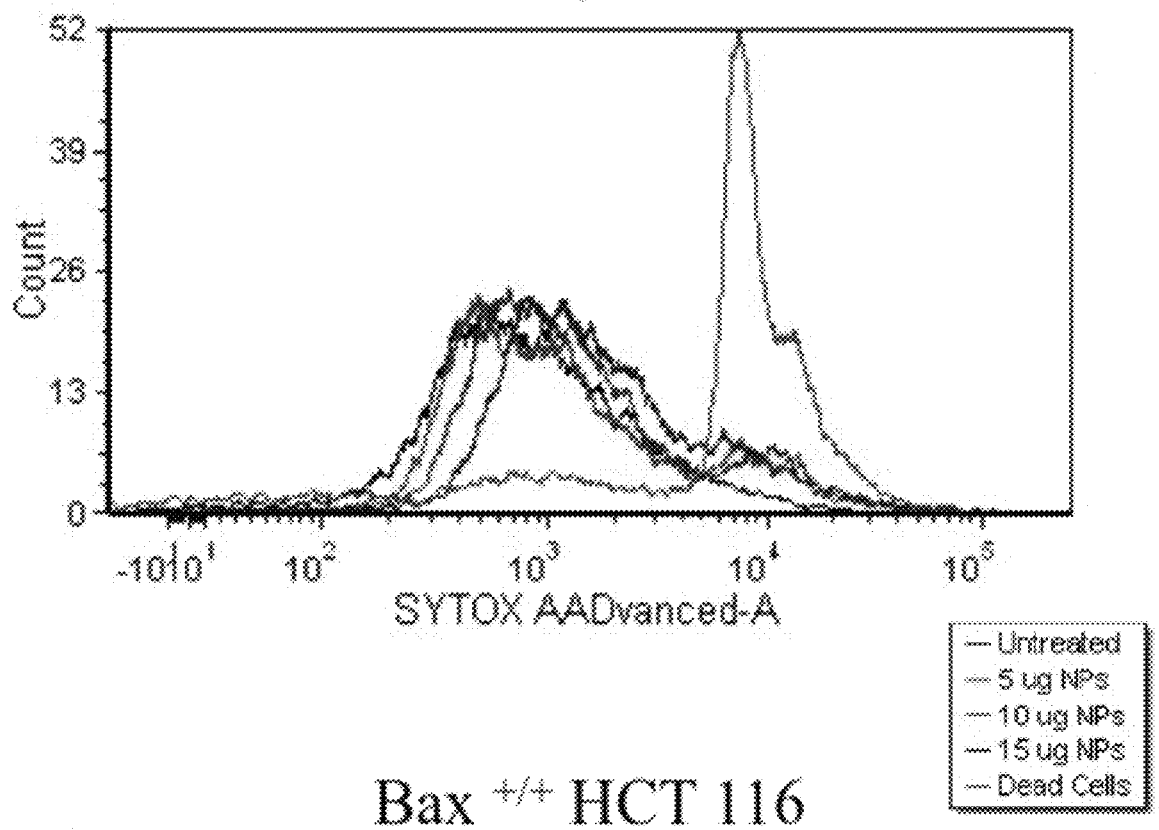
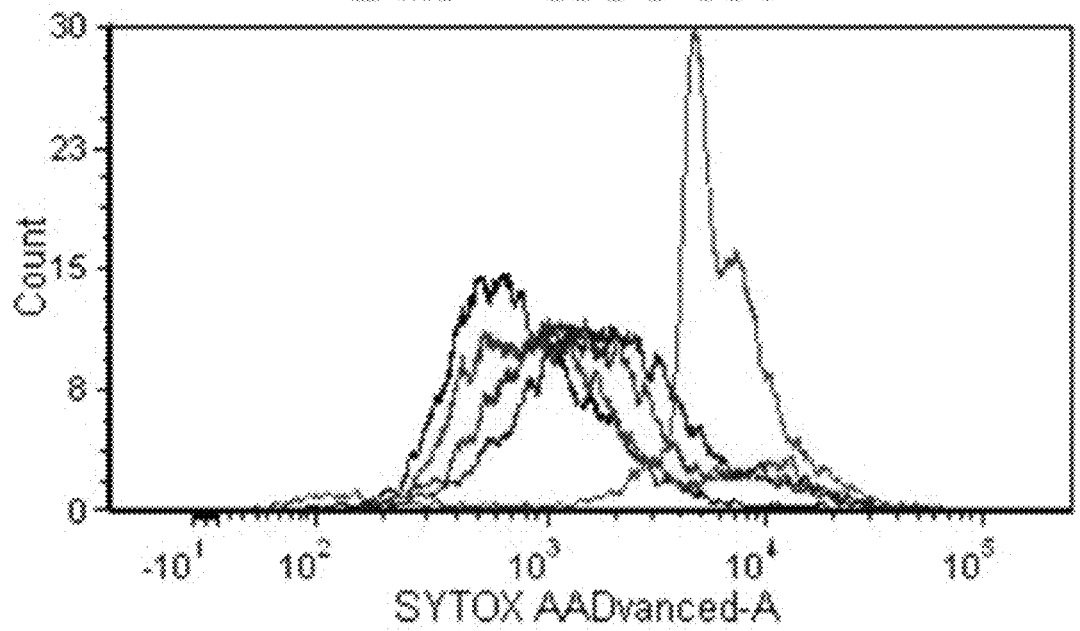

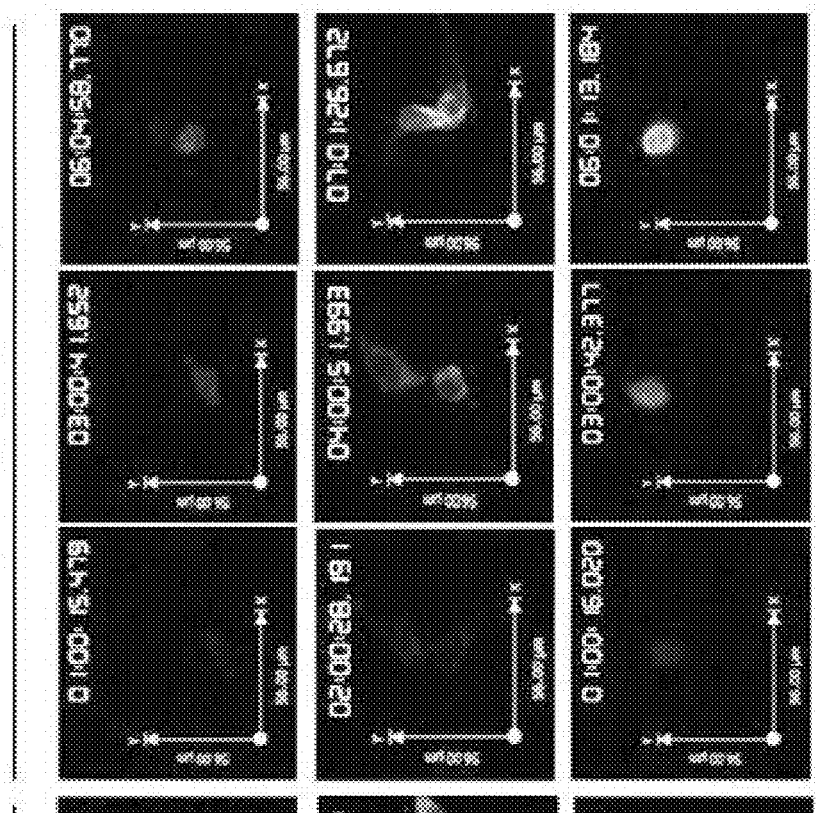
Figure 8D Bax⁺/⁺ HCT-116 Cells
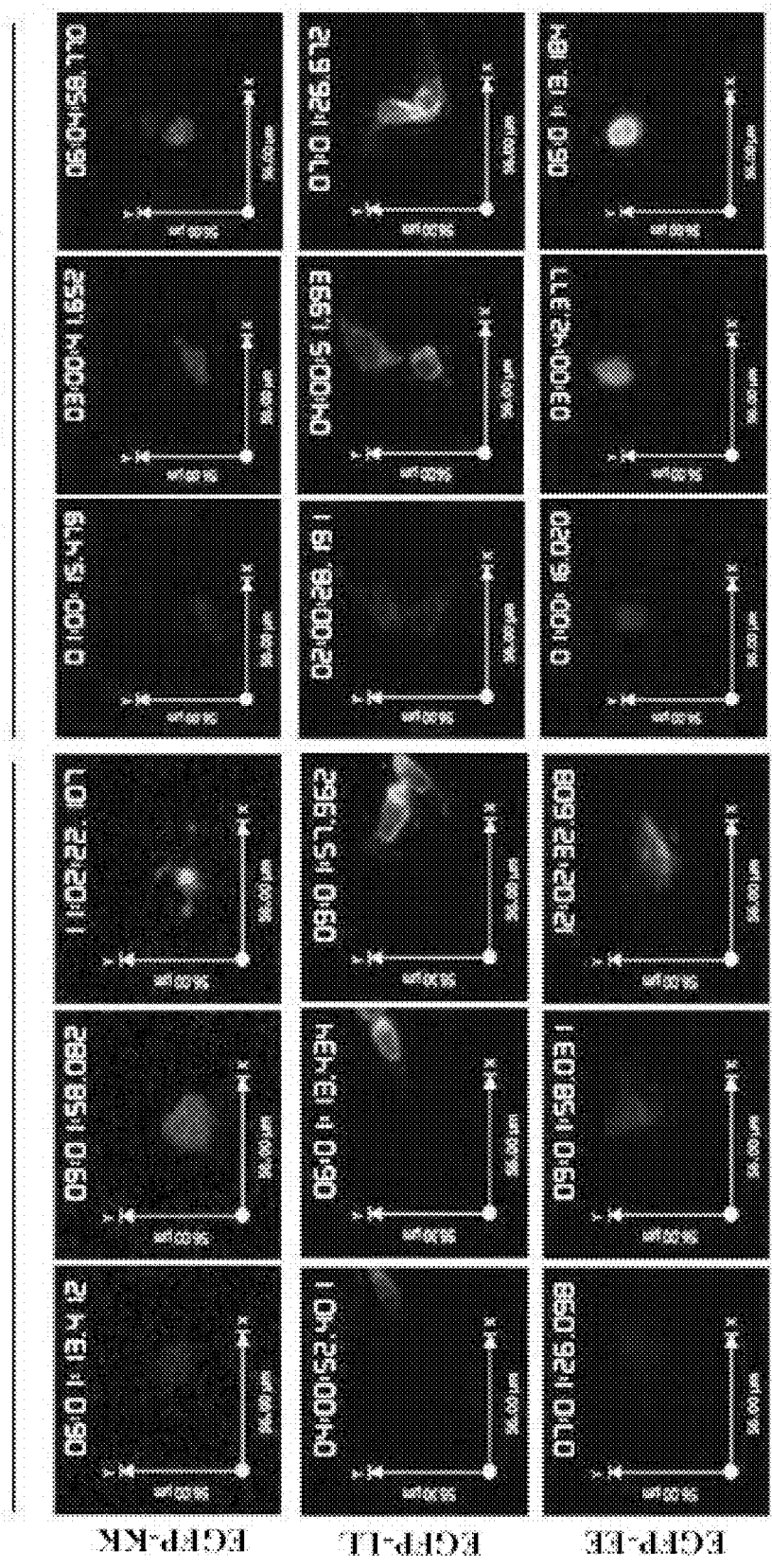
Figure 8C Bax⁻/⁻ HCT-116 Cells

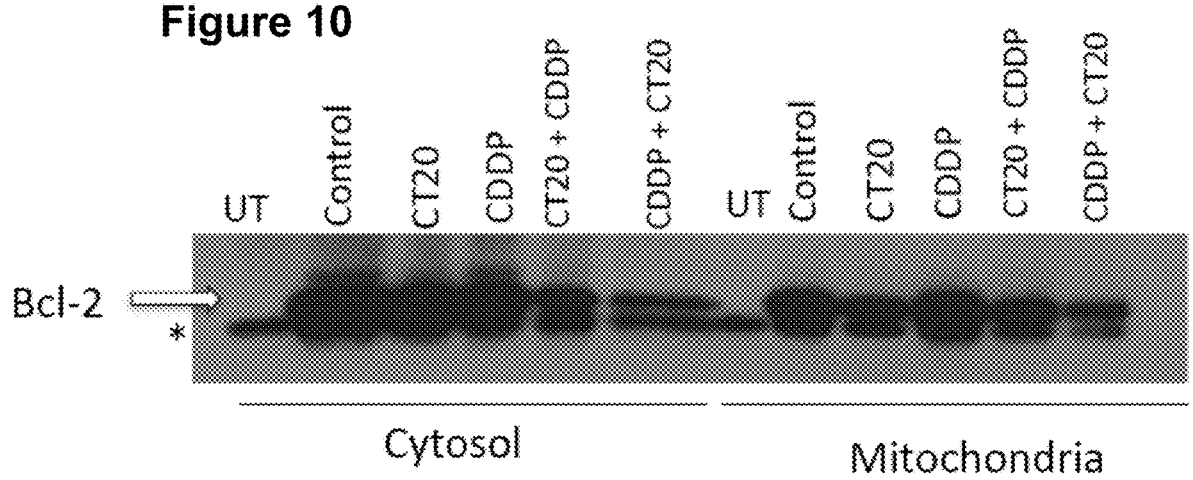

Figure 11A
Figure 11B
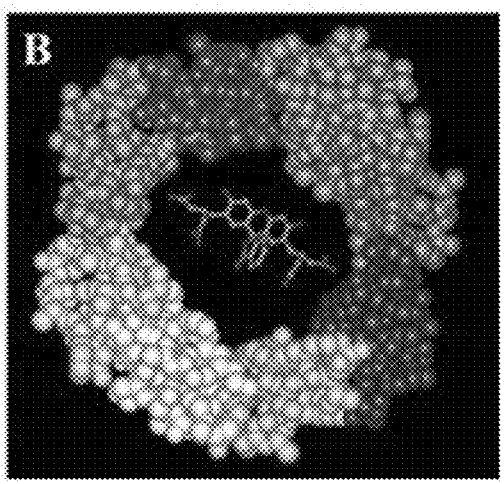

Figure 13

| PEPTIDE | SOURCE | SEQUENCE | % HYD | NET CHARGE | STRUCTURE | SEQ ID NO |
|---|---|---|---|---|---|---|
| CT20p | Human | VITFVAGVLTASLTIWKKMG | 60 | 2 | alpha | 1 |
| lactoferricin | Bos taurus | FKCRRWQWRMKKLGAPSITCVRRAF | 46 | 1 | beta | 39 |
| Indolicidin | Bos taurus | ILPWKWPWWPWRR | 53 | 3 | beta | 40 |
| Mellitin | Honey Bee | GIGAVLKVLTTGLPALISWIKRKRQQ | 46 | 5 | alpha | 41 |
| Brevinin 1 | Frog | FLPVLAGIAAKVVPALFCKITKKC | 66 | 4 | unknown | 42 |
| Ranalexin | Frog | FLGGLIKIVPAMICAVTKKC | 65 | 3 | alpha | 43 |
| Cecropin A | Insect | KWKLFKKIEKVGQNIRDGIIKAGPAVAVVGQATQIAK | 45 | 6 | alpha | 44 |
| Dermaseptin B2 | Frog | ALWKTMLKKLGTMALHAGKAALGAAADTISQGTQ | 54 | 3 | alpha | 45 |
| Magainin 2 | Frog | GIGKFLHSAKKFGKAFVGEIMNS | 43 | 3 | alpha | 46 |
| CT20p REV | n/a | GMKKWITLSATLVGAVFTIV | 60 | 2 | n/a | 47 |
| KLA peptide | synthetic | KLAKLAKKLAKLAK | 57 | 6 | alpha | 48 |
| Bax a5-a6 | Human | DGNFNWGRVVALFYFASKLVLKVPELIRT | 52 | 2 | alpha | 49 |
| BIM BH3 | Human | MRPEIWIAQELRRIGDEFNA | 40 | 0 | unknown | 50 |
| BID BH3 | Human | EDIIRNIARHLAQVGDSMDR | 40 | 0 | unknown | 51 |
| BAK BH3 | Human | GQVGRQLAIIGDDINR | 40 | 0 | unknown | 52 |

METHODS AND COMPOSITIONS COMPRISING A C-TERMINAL BAX PEPTIDE

CROSS-REFERENCE TO RELATED APPLICATIONS

This application is a continuation of application Ser. No. 14/717,884, filed May 20, 2015, now U.S. Pat. No. 10,159,706, which is a continuation of application Ser. No. 14/240,801, filed Feb. 25, 2014, now U.S. Pat. No. 9,040,662. U.S. Pat. No. 9,040,662 is a national stage application filed under 35 U.S.C. § 371 of PCT/US2012/052354, filed Aug. 24, 2012. PCT/US2012/052354 and U.S. Pat. No. 9,040,662 claim the benefit of U.S. Provisional Application No. 61/527,524, filed Aug. 25, 2011, and U.S. Provisional Application No. 61/645,891, filed May 11, 2012. Each of the above listed applications is incorporated herein by reference in their entireties.

STATEMENT REGARDING FEDERALLY SPONSORED RESEARCH OR DEVELOPMENT

This invention was made with Government Support under Grant No. GM083324 awarded by the National Institutes of Health. The Government has certain rights in the invention.

REFERENCE TO SEQUENCE LISTING

The Sequence Listing submitted May 20, 2015 as a text file named "10613_021US2_2015_05_20_Sequence_Listing.TXT", created on May 20, 2015, and having a size of 17,889 bytes, is hereby incorporated by reference pursuant to 37 C.F.R. § 1.52(e)(5).

BACKGROUND

The ability to kill cells provides a powerful therapeutic approach to treatment of disease or infection. Bacteria and fungi are becoming resistant to many of the currently available antimicrobial or antimycotic therapeutic compounds. Cancer cells frequently acquire mutations that enhance resistance to standard treatments. Principal among these mechanisms of drug resistance is abnormal expression of members of the B cell lymphoma-2 (Bcl-2) family (Oltersdorf et al., 2005). The Bcl-2 family consists of more than twenty anti- and pro-apoptotic members that modulate the balance between life and death. Tumors expressing high levels of anti-apoptotic proteins, such as Bcl-2, Mcl-1 or Bcl-xl, can be resistant to the effects of chemotherapeutics (Oltersdorf et al., 2005). This is accomplished, in part, by inhibition of the pro-apoptotic Bcl-2 family members, such as Bax, first identified as a protein that interacts with Bcl-2 (Oltvai et al., 1993). The association of Bax with mitochondria is linked to the release of cytochrome c and other death-mediators from mitochondrial reserves (Eskes et al., 1998).

Bax is a 21 kD protein of 192 amino acids, comprised of nine alpha helices (Suzuki et al., 2000). Under non-apoptotic conditions, Bax predominantly resides in the cytosol, with a small percentage of the protein localized to the mitochondria (Boohaker et al., 2011; Kaufmann et al., 2003; Putcha et al., 1999).

Despite advances in understanding the physiology and pathophysiology of cancer and/or aberrant cell growth, there is still a scarcity of compounds that are efficacious and safe in the treatment of cancer and/or aberrant cell growth. Therapeutics that are effective against bacteria and fungi are needed as these microorganisms grow more resistant to current therapies. These needs and other needs are satisfied by the present invention.

SUMMARY

Disclosed herein is a method of permeabilizing membranes of cells. Such membranes may be outer membranes, cell membranes or interior cellular membranes. The cells may be individual cells or cells in a subject. Methods may comprise administering to at least a cell an effective amount of a C-terminal Bax peptide (CT20p peptide) or a composition comprising an effective amount of a CT20p peptide.

Disclosed herein is a method of killing cancer cells in a subject comprising administering to at least one cell of a subject an effective amount of CT20p peptide or a composition comprising an effective amount of CT20p peptide. As used herein, CT20, CT20p peptide or CT20p peptide refers to a peptide comprising the last 20 amino acids of the Bax C-terminus.

Disclosed herein is a method of killing microbial cells, including but not limited to bacteria and fungi, whether on a surface, present in a colony or in a subject, comprising administering to at least one cell of a subject an effective amount of a CT20p peptide or a composition comprising an effective amount of a CT20p peptide.

Disclosed herein is a method of permeabilizing membranes of cells. Such membranes may be outer membranes, cell membranes or interior cellular membranes. The cells may be individual cells or cells in a subject. The method comprises (i) administering an effective amount of a CT20p peptide, and (ii) forming at least one pore in a membrane of at least one cell, wherein the peptide or a composition comprising an effective amount of a CT20p peptide destabilizes at least one membrane, facilitates ion exchange, and/or causes a sequestered molecule to be released.

Disclosed herein is a method of killing cancer cells in a subject comprising (i) administering to a subject an effective amount of a CT20p peptide, (ii) permeabilizing at least one membrane in a cell of the subject, and (iii) inducing cell death.

Disclosed herein is a method of killing bacterial or fungal cells in a subject comprising (i) administering to a subject an effective amount of a CT20p peptide, (ii) permeabilizing at least one membrane in a cell of the subject, and (iii) inducing cell death.

Disclosed herein is a composition for permeabilizing membranes on or in cells comprising a CT20p peptide.

Disclosed herein is a composition for killing cells comprising a CT20p peptide.

Disclosed herein is a composition for permeabilizing lipid membranes in cells comprising a CT20p peptide and one or more therapeutic agents, including but not limited to antibiotics, antimycotis, and anti-cancer drugs.

Disclosed herein is a composition for killing cells comprising a CT20p peptide and one or more therapeutic agents, including but not limited to antibiotics, antimycotis, and anticancer drugs.

DESCRIPTION OF DRAWINGS

The accompanying figures, which are incorporated in and constitute a part of this specification, illustrate several aspects and together with the description serve to explain the principles of the invention.

FIG. 1A shows that the C-terminus of wild-type Bax is distributed among cytosolic and mitochondria lysates as well as various substitutions at the C-terminus that modulate the association of the full-length protein to the mitochondria. FIG. 1B shows additional substitutions that modulate the association of the full length protein to the mitochondria.

FIG. 3A shows a schematic representation of the three dimensional structure of aliphatic hyperbranched nanoparticles. FIG. 3C shows that DiI-loaded nanoparticles result in minimal to no cell death compared to the positive control (dead cells).

FIGS. 8C and 8D show $Bax^{+/+}$ HCT-116 cells (FIG. 8C) and $Bax^{-/-}$ HCT-116 cells (FIG. 8D) that were transfected with EGFP-Kk or K189/K190 mutants.

FIG. 10 shows the expression of Bcl-2 in transiently transfected MDA-MB-231 cells.

FIGS. 11A and B show a model for a membrane pore formed by the CT20 Bax peptide. FIG. 11A shows peptide molecules in ribbon format. FIG. 11B shows a top view of the pore formed by CT20p in CPK format. A calcein molecule is shown within the pore in a ball and stick format.

FIG. 13 is a table of CT20p peptide comparison with antimicrobial and apoptosis inducing peptides.

Figure 1A:
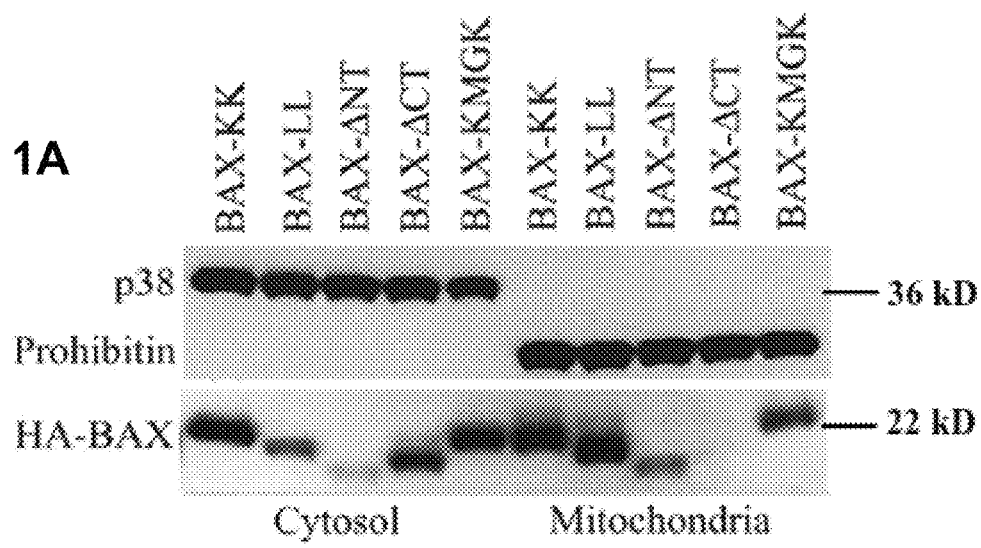
FIGS. 1A and 1B show distribution of Bax proteins in lysates.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention comprises methods and compositions for disrupting the cellular membranes of cells. The cells may be prokaryotes or eukaryotes, and may be found as individual cells, in colonies, on or within multi-celled organisms such as plants or animals. For example, microbial cells may be found on the surface of an animal, such as a human, or within the animal. Cancer cells may be found in a subject, such as a plant, human or animal.

Mitochondria play a central role in regulating both apoptotic and non-apoptotic or necrotic pathways by selectively releasing cell death promoting factors. The determination as to whether or not an apoptotic or non-apoptotic cell death pathway will be activated is dependent on the type of death mediator released from the mitochondria.

Most current anti-cancer drugs only trigger the apoptotic pathway. Defects in the apoptotic machinery can contribute to tumor formation and resistance to treatment, creating a need to identify anti-cancer agents that kill cells by novel mechanisms. The development of a new therapeutic agent that induces cell death via a non-apoptotic mechanism and can be used in combination with standards drugs that induce apoptosis will have significant impact on the treatment of drug resistance cancers and could greatly improve overall patient outcomes. As described herein, the death-inducing properties of the C-terminal (CT) of the alpha-9 helix of Bax, an amphipathic domain with putative membrane binding properties, were examined.

To examine the cytotoxic potential of the CT domain of Bax, a peptide (CT20) was generated. The CT20p peptide permeabilized mitochondrial-like lipid vesicles and caused cell death. The cell death pathway triggered by the CT20p peptide was independent of effector caspases and resistant to Bcl-2 over-expression. This indicates that the CT20p peptide can be used in combinatorial therapies to sensitize drug-resistant cancer cells to treatment. Other properties of the CT20 Bax peptide, show that the CT20p peptide causes cell membrane permeability, and such a peptide may be combined with antimicrobial therapeutics or therapies to cause cell death in microorganisms, such as gram-positive and gram-negative bacteria, other types of bacteria, fungi and other microorganisms and infectious agents.

A. Compositions

Disclosed herein are compositions comprising a CT20p peptide.

1. Compositions for Permeabilizing Membranes in Cells

Disclosed herein is a composition for permeabilizing membranes in cells comprising a CT20p peptide. The cells may be individual cells, or cells that are on or in a subject. In an aspect, the cells are eukaryotic or prokaryotic cells, including but not limited to bacteria and fungi. In an aspect, the cells are in a subject. In an aspect, the cells are on a surface, which may be inert or may be the surface of a subject. In an aspect, the cells are cancer cells or transformed cells. In an aspect, the cancer cell can be a cell from any type of cancer including, but not limited to, cancer of the head and neck cancer, esophagus, stomach, pancreas, kidney, bladder, bone, brain, and cervix. In an aspect, the cancer is breast cancer. In an aspect, the cancer is colorectal cancer. In an aspect, the cancer is lung cancer. In an aspect, the cancer is a drug resistant cancer. In an aspect, the cancer cell is a drug resistant cancer cell. In an aspect, a disclosed composition comprising a truncated Bax peptide is administered directly into a tumor.

In an aspect, a disclosed composition for permeabilizing membranes in cells forms one one or more pores in the membranes of the cells. In an aspect, the membrane may be an outer membrane, a cellular membrane or an organelle membrane. In an aspect, the membrane is a mitochondrial membrane. In an aspect, the one or more pores are formed in a mitochondrial membrane of a cancer cell.

In an aspect, a disclosed composition for permeabilizing membranes in cells destabilizes a cellular membrane. In an aspect, a disclosed composition facilitates ion exchange. In an aspect, a disclosed composition causes a sequestered molecule to be released. In an aspect, a disclosed composition destabilizes a cellular membrane, facilitates ion exchange, and causes a sequestered molecule to be released. In an aspect, a disclosed composition destabilizes a cellular membrane and facilitates ion exchange. In an aspect, a disclosed composition destabilizes a cellular membrane and causes a sequestered molecule to be released. In an aspect, a disclosed composition facilitates ion exchange and causes a sequestered molecule to be released.

In an aspect, a disclosed composition for permeabilizing membranes in cells comprising a CT20p peptide induces cell death. In an aspect, the cell death mimics necrosis. In an aspect, the cell death occurs independent of endogenous Bax activity. In an aspect, the cell death occurs independent of endogenous caspase activity. In an aspect, the cell death is resistant to Bcl-2 over-expression.

In an aspect, a disclosed composition for permeabilizing membranes in cells comprising a CT20p peptide induces cell death, wherein (i) the cell death mimics necrosis, (ii) the cell death occurs independent of endogenous Bax activity, (iii) the cell death occurs independent of endogenous caspase activity, or (iv) the cell death is resistant to Bcl-2 over-expression, or (v) the cell death exhibits a combination thereof.

In an aspect, a pore-forming composition may comprise an amount of a CT20p peptide so that pores comprising from two to ten peptides, from two to eight peptides, from four to ten peptides, from five, six, seven, eight, nine, ten or more peptides, can be formed.

In an aspect, a disclosed composition for permeabilizing membranes in cells comprises a CT20p peptide comprising SEQ ID NO: 1, SEQ ID NO: 2, SEQ ID NO: 3, and/or SEQ ID NO: 4. For example, in an aspect, a disclosed CT20p peptide is VTIFVAGVLTASLTIWKKMG (SEQ ID NO: 1). In an aspect, a disclosed CT20p peptide is VTIFVAGVLTASLTIWEEMG (SEQ ID NO: 2). In an aspect, a disclosed CT20p peptide is VTIFVAGVLTASLTIWLLMG (SEQ ID NO: 3). In an aspect, a disclosed CT20p peptide is VTIFVAGVLTASLTIWRRMG (SEQ ID NO: 4). In an aspect, a disclosed composition for permeabilizing membranes in cells comprises one or more CT20 Bax peptides, wherein the one or more CT20 Bax peptides comprise SEQ ID NO: 1, SEQ NO: 2, SEQ ID NO: 3; or SEQ ID NO: 4.

In an aspect, a CT20p peptide of a disclosed composition for permeabilizing membranes in cells is encapsulated in polymeric nanoparticles. In an aspect, the nanoparticles are aminated. In an aspect, the nanoparticles are carboxylated.

In an aspect, a disclosed composition for permeabilizing membranes in cells comprising a CT20p peptide further comprises one or more therapeutic compounds, such as one or more antimicrobial compounds, one or more antibacterial compounds, one or more antifungal compounds, or one or more anti-cancer drugs, or a combination thereof. In an aspect, the one or more anti-cancer drugs comprise cisplatin. In an aspect, the one or more anti-cancer drugs induce apoptosis. In an aspect, a disclosed composition comprising a CT20p peptide further comprises one or more chemotherapeutic drugs. In an aspect, a disclosed composition comprising a CT20p peptide further comprises one or more radiosensitizers.

In an aspect, a disclosed composition for permeabilizing membranes in cells comprising a CT20p peptide further comprises (i) one or more anti-cancer drugs, (ii) one or more chemotherapeutic drugs, and (iii) one or more radiosensitizers. In an aspect, a disclosed composition further comprises one or more anti-cancer drugs and one or more chemotherapeutic drugs. In an aspect, a disclosed composition further comprises one or more anti-cancer drugs and one or more radiosensitizers. In an aspect, a disclosed composition further comprises one or more chemotherapeutic drugs and one or more radiosensitizers.

In an aspect, a disclosed composition for permeabilizing membranes in cells is administered to a subject. In an aspect, the subject is a mammal. In an aspect, the mammal is a primate. In an aspect, the mammal is a human. In an aspect, the human is a patient.

In an aspect, a disclosed composition for permeabilizing membranes in cells comprising a CT20p peptide is administered to a subject at least two times. In an aspect, a disclosed composition is administered to the subject two or more times. In an aspect, a disclosed composition is administered at routine or regular intervals. For example, in an aspect, a disclosed composition is administered to the subject one time per day, or two times per day, or three or more times per day. In an aspect, a disclosed composition is administered to the subject daily, or one time per week, or two times per week, or three or more times per week, etc. In an aspect, a disclosed composition is administered to the subject weekly, or every other week, or every third week, or every fourth week, etc. In an aspect, a disclosed composition is administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect, following the administration of a disclosed composition for permeabilizing membranes in cells comprising a CT20p peptide, the cells are sensitized to treatment. In an aspect, following the administration of a disclosed composition comprising a CT20p peptide, a subject is sensitized to treatment. In an aspect, an increased sensitivity or a reduced sensitivity to a treatment, such as a therapeutic treatment, is measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed composition comprising a CT20p peptide to the sensitivity of a cell or subject that has not been administered a disclosed composition comprising a CT20p peptide.

For example, in an aspect, following the administration of a disclosed composition for permeabilizing membranes in cells comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed composition comprising a CT20p peptide. In an aspect, following the administration of a disclosed composition comprising a CT20p peptide the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed composition comprising a CT20p peptide. The determination of a cell's or a subject's sensitivity or resistance is routine in the art and within the skill of an ordinary clinician and/or researcher.

In an aspect, the determination of a cell's or a subject's sensitivity or resistance to treatment can be monitored. For example, in an aspect, data regarding sensitivity or resistance resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a a subject can be modified based on data regarding a cell's or a subject's sensitivity or resistance to treatment. For example, in an aspect, the treatment can modified by changing the the dose of a disclosed compositions, the route of administration of a disclosed compositions, the frequency of administration of a disclosed composition, etc.

Disclosed herein is a composition for permeabilizing lipid membranes in cells comprising a CT20p peptide and one or more anti-cancer drugs.

2. Compositions for Killing Cells

Disclosed herein is a composition for killing cells comprising a CT20p peptide. In an aspect, the cells are eukaryotic or prokaryotic cells, including but not limited to bacteria and fungi. In an aspect, the cells are in a subject. In an aspect, the cells are on a surface, which may be inert or may be the surface of a subject. In an aspect, the cells are cancer cells or transformed cells. In an aspect, the cancer cell can be a cell from any type of cancer including, but not limited to, cancer of the head and neck cancer, esophagus, stomach, pancreas, kidney, bladder, bone, brain, and cervix. In an aspect, the cancer is breast cancer. In an aspect, the cancer is colorectal cancer. In an aspect, the cancer is lung cancer. In an aspect, the cancer is a drug resistant cancer. In an aspect, the cancer cell is a drug resistant cancer cell. In an aspect, a disclosed composition comprising a CT20p peptide is administered directly into a tumor.

In an aspect, a disclosed composition for killing cells forms one or more pores in the membranes of the cells. In an aspect, the membrane may be an outer membrane, a cellular membrane or an organelle membrane. In an aspect, the membrane is a mitochondrial membrane. In an aspect, the one or more pores are formed in a mitochondrial membrane. In an aspect, the one or more pores are formed in a mitochondrial membrane of a cancer cell.

In an aspect, a disclosed composition for killing cells destabilizes a cellular membrane. In an aspect, a disclosed composition facilitates ion exchange. In an aspect, a disclosed composition causes a sequestered molecule to be released. In an aspect, a disclosed composition destabilizes a cellular membrane, facilitates ion exchange, and causes a sequestered molecule to be released. In an aspect, a disclosed composition destabilizes a cellular membrane and facilitates ion exchange. In an aspect, a disclosed composition destabilizes a cellular membrane and causes a sequestered molecule to be released. In an aspect, a disclosed composition facilitates ion exchange and causes a sequestered molecule to be released.

In an aspect, a disclosed composition for killing cells comprising a CT20p peptide induces cell death. In an aspect, the cell death mimics necrosis. In an aspect, the cell death occurs independent of endogenous Bax activity. In an aspect, the cell death occurs independent of endogenous caspase activity. In an aspect, the cell death is resistant to Bcl-2 over-expression.

In an aspect, a disclosed composition for killing cells comprising a CT20p peptide induces cell death, wherein (i) the cell death mimics necrosis, (ii) the cell death occurs independent of endogenous Bax activity, (iii) the cell death occurs independent of endogenous caspase activity, or (iv) the cell death is resistant to Bcl-2 over-expression, or (v) the cell death exhibits a combination thereof.

In an aspect, a composition for killing cells comprises a pore-forming composition which may comprise an amount of a CT20p peptide so that pores comprising from two to ten peptides, from two to eight peptides, from four to ten peptides, from five, six, seven, eight, nine, ten or more peptides, can be formed.

In an aspect, a disclosed composition for killing cells comprises a CT20p peptide comprising SEQ ID NO: 1, SEQ ID NO: 2, SEQ ID NO: 3, and/or SEQ ID NO: 4. For example, in an aspect, a disclosed CT20p peptide peptide is VTIFVAGVLTASLTIWKKMG (SEQ ID NO: 1). In an aspect, a disclosed CT20p peptideis VTIFVAGVLTASLTIWEEMG (SEQ ID NO: 2). In an aspect, a disclosed CT20p peptideis VTIFVAGVLTASLTIWLLMG (SEQ ID NO: 3). In an aspect, a disclosed CT20p peptide is VTIFVAGVLTASLTIWRRMG (SEQ ID NO: 4). In an aspect, a disclosed composition for killing cells comprises one or more CT20 Bax peptides, wherein the one or more CT20 Bax peptides comprise SEQ ID NO: 1, SEQ NO: 2, SEQ ID NO: 3; or SEQ ID NO: 4.

In an aspect, a CT20p peptide of a disclosed composition for killing cells is encapsulated in polymeric nanoparticles.

In an aspect, the nanoparticles are aminated. In an aspect, the nanoparticles are carboxylated.

In an aspect, a disclosed composition for killing cells comprising a CT20p peptide further comprises one or more therapeutic compounds, such as one or more antimicrobial compounds, one or more antibacterial compounds, one or more antifungal compounds, or one or more anti-cancer drugs, or a combination thereof. In an aspect, the one or more anti-cancer drugs comprise cisplatin. In an aspect, the one or more anti-cancer drugs induce apoptosis. In an aspect, a disclosed composition for killing cells comprising a CT20p peptide further comprises one or more chemotherapeutic drugs. In an aspect, a disclosed composition for killing cells comprising a CT20p peptide further comprises one or more radiosensitizers.

In an aspect, a disclosed composition for killing cells comprising a CT20p peptide further comprises (i) one or more anti-cancer drugs, (ii) one or more chemotherapeutic drugs, and (iii) one or more radiosensitizers. In an aspect, a disclosed composition for killing cells further comprises one or more anti-cancer drugs and one or more chemotherapeutic drugs. In an aspect, a disclosed composition for killing cells further comprises one or more anti-cancer drugs and one or more radiosensitizers. In an aspect, a disclosed composition for killing cells further comprises one or more chemotherapeutic drugs and one or more radiosensitizers.

In an aspect, a disclosed composition for killing cells is administered to a subject. In an aspect, the subject is a mammal. In an aspect, the mammal is a primate. In an aspect, the mammal is a human. In an aspect, the human is a patient.

In an aspect, a disclosed composition for killing cells comprising a CT20p peptide is administered to a subject at least two times. In an aspect, a disclosed composition is administered to the subject two or more times. In an aspect, a disclosed composition is administered at routine or regular intervals. For example, in an aspect, a disclosed composition is administered to the subject one time per day, or two times per day, or three or more times per day. In an aspect, a disclosed composition is administered to the subject daily, or one time per week, or two times per week, or three or more times per week, etc. In an aspect, a disclosed composition is administered to the subject weekly, or every other week, or every third week, or every fourth week, etc. In an aspect, a disclosed composition is administered to the subject monthly, or every other month, or every third month, or every fourth month, etc. In an aspect, the repeated administration of a disclosed composition occurs over a predetermined or definite duration of time. In an aspect, the repeated administration of a disclosed composition occurs over an indefinite period of time.

In an aspect, following the administration of a disclosed composition for killing cells comprising a CT20p peptide, the cells are sensitized to treatment. In an aspect, following the administration of a disclosed composition for killing cells comprising a CT20p peptide, a subject is sensitized to treatment. In an aspect, an increased sensitivity or a reduced sensitivity sensitivity to a treatment, such as a therapeutic treatment, is measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or subject following administration of a disclosed composition for killing cells comprising a CT20p peptide to the sensitivity of a cell or subject that has not been administered a disclosed composition for killing cells comprising a CT20p peptide.

For example, in an aspect, following the administration of a disclosed composition for killing cells comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed composition for killing cells comprising a CT20p peptide. In an aspect, following the administration of a disclosed composition for killing cells comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed composition for killing cells comprising a CT20p peptide. The determination of a cell's or a subject's sensitivity or resistance is routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

Disclosed herein is a composition for killing cells comprising a CT20p peptide and one or more anti-cancer drugs.

3. Pharmaceutical Compositions

In an aspect, the invention relates to pharmaceutical compositions comprising a disclosed composition for permeabilizing membranes in cells. In an aspect, the invention relates to pharmaceutical compositions comprising a disclosed composition for killing cells. In an aspect, the disclosed compositions for permeabilizing membranes and cells and for killing cells comprise a CT20 Bax peptide. In an aspect, a pharmaceutical composition can be provided comprising a therapeutically effective amount of at least one disclosed composition and a pharmaceutically acceptable carrier.

B. Methods Comprising a Disclosed Composition

1. Permeabilizing Membranes of Cells

Disclosed herein are methods of permeabilizing membranes of cells. The cells may be individual cells, or cells that are on or in a subject. In an aspect, the cells are eukaryotic or prokaryotic cells, including but not limited to bacteria and fungi.

In an aspect, disclosed herein is a method of permeabilizing membranes of cells in a subject comprising administering to at least a cell a CT20p peptide. In an aspect, disclosed herein is a method of permeabilizing membranes of cells in a subject comprising administering to at least a cell a composition comprising an effective amount of a CT20p peptide. In an aspect, the membrane may be an outer membrane, a cellular membrane or an organelle membrane. In an aspect the cell is a bacterial cell. In an aspect, the cell is a fungal cell. In an aspect, the cell is a microbial cell. In an aspect, the cell is a cancer cell or a transformed cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer is breast cancer. In an aspect, the cancer is colorectal cancer. In an aspect, the cancer is lung cancer. In an aspect, the cancer is a drug resistant cancer. In an aspect, the cancer cell is a drug resistant cancer cell. In an aspect, a CT20p peptide or a composition comprising an effective amount of a CT20p peptide is administered directly into a tumor.

In an aspect of a disclosed a method of permeabilizing membranes of cells, a CT20p peptide or a composition comprising an effective amount of a CT20p peptide forms at least one pore in the membrane of the cell. In an aspect, a CT20p peptide or a composition comprising an effective amount of a CT20p peptide forms two or more pores in the membrane of the cell. In an aspect, cell is a cancer cell. In an aspect, the one or more pores are formed in a mitochondrial membrane. In an aspect, the one or more pores are formed in a mitochondrial membrane of a cancer cell.

In an aspect of a disclosed method of permeabilizing membranes of cells in a subject, a CT20p peptide or a composition comprising an effective amount of a CT20p peptide destabilizes a cellular membrane, facilitates ion exchange, and causes a sequestered molecule to be released. In an aspect, a CT20p peptide or a composition comprising an effective amount of a CT20p peptide destabilizes a cellular membrane. In an aspect, a CT20p peptide or a composition comprising an effective amount of a CT20p peptide facilitates ion exchange, exchange. In an aspect, a CT20p peptide or a composition comprising an effective amount of a CT20p peptide causes a sequestered molecule to be released. In an aspect, a CT20p peptide or a composition comprising an effective amount of a CT20p peptide destabilizes a cellular membrane and facilitates ion exchange. In an aspect, a CT20p peptide or a composition comprising an effective amount of a CT20p peptide destabilizes a cellular membrane and causes a sequestered molecule to be released. In an aspect, a CT20p peptide or a composition comprising an effective amount of a CT20p peptide facilitates ion exchange and causes a sequestered molecule to be released.

In an aspect, following the administration of a CT20p peptide or a composition comprising an effective amount of a CT20p peptide, the cells are sensitized to treatment. In an aspect, following the administration of CT20p peptide or a composition comprising an effective amount of a CT20p peptide, a subject is sensitized to treatment. In an aspect, an increased sensitivity or a reduced sensitivity to a treatment, such as a therapeutic treatment, is measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a CT20p peptide or a composition comprising an effective amount of a CT20p peptide to the sensitivity of a cell or subject that has not been administered a CT20p peptide or a composition comprising an effective amount of a CT20p peptide.

For example, in an aspect, following the administration of a CT20p peptide or a composition comprising an effective amount of a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a CT20p peptide or a disclosed composition comprising an effective amount of a CT20p peptide. In an aspect, following the administration of a CT20p peptide or a composition comprising an effective amount of a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a CT20p peptide or a disclosed composition comprising an effective amount of a CT20p peptide. The determination of a cell's or a subject's sensitivity or resistance is routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

In an aspect, a disclosed method of permeabilizing membranes of cells in a subject further comprises repeating the administration a CT20p peptide or a composition comprising an effective amount of a CT20p peptide. In an aspect, a CT20p peptide or a composition comprising an effective amount of a CT20p peptide is administered to the subject at least two times. In an aspect, a CT20p peptide or a composition comprising an effective amount of a CT20p peptide is administered to the subject two or more times. In an aspect, a CT20p peptide or a composition comprising an effective amount of a CT20p peptide administered at routine or regular intervals. For example, in an aspect, a CT20p peptide or a composition comprising an effective amount of a CT20p peptide is administered to the subject one time per day, or two times per day, or three or more times per day. In an aspect, a CT20p peptide or a composition comprising an effective amount of a CT20p peptide is administered to the subject daily, or one time per week, or two times per week, or three or more times per week, etc. In an aspect, a CT20p peptide or a composition comprising an effective amount of a CT20p peptide is administered to the subject weekly, or every other week, or every third week, or every fourth week, etc. In an aspect, a CT20p peptide or a composition comprising an effective amount of a CT20p peptide is administered to the subject monthly, or every other month, or every third month, or every fourth month, etc. In an aspect, the repeated administration of a CT20p peptide or a composition comprising an effective amount of a CT20p peptide occurs over a pre-determined or definite duration of time. In an aspect, the repeated administration of a CT20p peptide or a composition comprising an effective amount of a CT20p peptide occurs over an indefinite period of time.

In an aspect, a disclosed method of permeabilizing membranes of cells in a subject further comprises inducing cell death. In an aspect, cell death mimics necrosis. In an aspect, cell death occurs independent of endogenous Bax activity. In an aspect, cell death occurs independent of endogenous caspase activity. In an aspect, cell death is resistant to Bcl-2 over-expression.

In an aspect, a disclosed method of permeabilizing membranes of cells in a subject comprising administering a CT20p peptide or a composition comprising an effective amount of a CT20p peptide further comprises inducing cell death. Cell death may include, but is not limited to wherein (i) cell death mimics necrosis, (ii) cell death occurs independent of endogenous Bax activity, (iii) cell death occurs independent of endogenous caspase activity, or (iv) cell death is resistant to Bcl-2 over-expression, or (v) cell death exhibits a combination thereof.

In an aspect, a CT20p peptide or a composition comprising an effective amount of a CT20p peptide of a disclosed method of permeabilizing cell membranes comprises SEQ ID NO: 1, SEQ ID NO: 2, SEQ ID NO: 3, and/or SEQ ID NO: 4. For example, in an aspect, a CT20p peptide is VTIFVAGVLTASLTIWKKMG (SEQ ID NO: 1). In an aspect, a CT20p peptide is VTIFVAGVLTASLTIWEEMG (SEQ ID NO: 2). In an aspect, a CT20p peptide is VTIFVAGVLTASLTIWLLMG (SEQ ID NO: 3). In an aspect, a CT20p peptide is VTIFVAGVLTASLTIWRRMG (SEQ ID NO: 4). In an aspect, a disclosed composition comprising an effective amount of a CT20p peptide comprises one or more CT20 Bax peptides, wherein the one or more CT20 Bax peptides comprise SEQ ID NO: 1, SEQ NO: 2, SEQ ID NO: 3; or SEQ ID NO: 4, or two or more of each. In an aspect, a CT20p peptide of a disclosed method of permeabilizing membranes of cells in a subject is encapsulated in polymeric nanoparticles. In an aspect, the nanoparticles are aminated. In an aspect, the nanoparticles are carboxylated.

In an aspect, a disclosed method of permeabilizing membranes comprising administering a CT20p peptide or a composition comprising an effective amount of a CT20p peptide further comprises administering one or more anti-cancer drugs. In an aspect, the one or more anti-cancer drugs comprise cisplatin. In an aspect, the one or more anti-cancer drugs induce apoptosis. In an aspect, a disclosed method of permeabilizing membranes comprising administering a CT20p peptide or a composition comprising an effective amount of a CT20p peptide further comprises administering one or more chemotherapeutic drugs. In an aspect, a disclosed method of permeabilizing membranes comprising administering a CT20p peptide or or a composition comprising an effective amount of a CT20p peptide further comprises administering one or more radiosensitizers.

In an aspect, a disclosed method of permeabilizing membranes comprising administering a CT20p peptide or a composition comprising an effective amount of a CT20p peptide further comprises administering (i) one or more anti-cancer drugs, (ii) one or more chemotherapeutic drugs, and (iii) one or more radiosensitizers. In an aspect, a disclosed method further comprises administering one or more anti-cancer drugs and one or more chemotherapeutic drugs. In an aspect, a disclosed method further comprises administering one or more anti-cancer drugs and one or more radiosensitizers. In an aspect, a disclosed method further comprises administering one or more chemotherapeutic drugs and one or more radiosensitizers.

In an aspect of a disclosed method of permeabilizing membranes of cells, which may be in or on a subject, the subject is a mammal. In an aspect, the mammal is a primate. In an aspect, the mammal is a human. In an aspect, the human is a patient.

In an aspect, disclosed herein is a method of permeabilizing membranes of cells in a subject comprising (i) administering to a subject an effective amount of a CT20p peptide or a composition comprising an effective amount of a CT20p peptide, and (ii) forming at least one pore in a membrane of at least one cell of the subject, wherein the peptide destabilizes at least one membrane, facilitates ion exchange, and/or causes a sequestered molecule to be released.

2. Killing Cancer Cells

Disclosed herein are methods of killing cancer cells.

In an aspect, disclosed herein is a method of killing cancer cells in a subject comprising administering to at least one cell of a subject an effective amount of a CT20p peptide. In an aspect, disclosed herein is a method of killing cancer cells in a subject comprising administering to at least one cell of a subject a composition comprising an effective amount of a CT20p peptide. In an aspect, the cell is a cancer cell or a transformed cell. In an aspect, the cancer cell can be a cell from any type of cancer including, but not limited to, cancer of the head and neck cancer, esophagus, stomach, pancreas, kidney, bladder, bone, brain, and cervix. In an aspect, the cancer is breast cancer. In an aspect, the cancer is colorectal cancer. In an aspect, the cancer is lung cancer. In an aspect, the cancer is a drug resistant cancer. In an aspect, the cancer cell is a drug resistant cancer cell. In an aspect, a CT20p peptide or a composition comprising an effective amount of a CT20p peptide is administered directly into a tumor.

In an aspect, a disclosed method of killing cancer cells in a subject further comprises permeabilizing at least one membrane in the cell. In an aspect, the membrane is a mitochondrial membrane. In an aspect, the one or more pores are formed in a mitochondrial membrane. In an aspect, the one or more pores are formed in a mitochondrial membrane of a cancer cell.

In an aspect, permeabilizing at least one membrane in the cell comprises destabilizing a cellular membrane, facilitating ion exchange, and causing a sequestered molecule to be released. In an aspect, permeabilizing at least one membrane in the cell comprises destabilizes a cellular membrane. In an aspect, permeabilizing at least one membrane in the cell comprises facilitating ion exchange. In an aspect, permeabilizing at least one membrane in the cell comprises causing a sequestered molecule to be released. In an aspect, permeabilizing at least one membrane in the cell comprises destabilizing a cellular membrane and facilitating ion exchange. In an aspect, permeabilizing at least one membrane in the cell comprises destabilizing a cellular membrane and causing a sequestered molecule to be released. In an aspect, permeabilizing at least one membrane in the cell comprises facilitating ion exchange and causing a sequestered molecule to be released.

In an aspect of a disclosed method of killing cancer cells in a subject, the cancer cells are sensitized to treatment. In an aspect of a disclosed method of killing cancer cells in a subject, the subject is sensitized to treatment. In an aspect, an increased sensitivity or a reduced sensitivity to a treatment, such as a therapeutic treatment, is measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a CT20p peptide or a composition comprising a CT20p peptide to the sensitivity of a cell or subject that has not been administered a CT20p peptide or a composition comprising a CT20p peptide.

For example, in an aspect, following the administration of a CT20p peptide or a composition comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a CT20p peptide or a composition comprising a CT20p peptide. In an aspect, following the administration of a CT20p peptide or a composition comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a CT20p peptide or a composition comprising a CT20p peptide. The determination of a cell's or a subject's sensitivity or resistance is routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than periodic times. In an aspect, treatment for a subject can be modified based on data regarding a cell's or a subject's sensitivity or resistance to treatment.

In an aspect, a disclosed method of killing cancer cells in a subject further comprises repeating the administration of a CT20p peptide or a composition comprising an effective amount of a CT20p peptide. In an aspect, a CT20p peptide or a composition comprising an effective amount of a CT20p peptide is administered to the subject at least two times. In an aspect, a CT20p peptide or a composition comprising an effective amount of a CT20p peptide is administered to the subject two or more times. In an aspect, a CT20p peptide or a composition comprising an effective amount of a CT20p peptide is administered at routine or regular intervals. For example, in an aspect, a CT20p peptide or a composition comprising an effective amount of a CT20p peptide is administered to the subject one time per day, or two times per day, or three or more times per day. In an aspect, a CT20p peptide or a composition comprising an effective amount of a CT20p peptide is administered to the subject daily, or one time per week, or two times per week, or three or more times per week, etc. In an aspect, a CT20p peptide or a composition comprising an effective amount of a CT20p peptide is administered to the subject weekly, or every other week, or every third week, or every fourth week, etc. In an aspect, a CT20p peptide or a composition comprising an effective amount of a CT20p peptide is administered to the subject monthly, or every other month, or every third month, or every fourth month, etc. In an aspect, the repeated administration of a CT20p peptide or a composition comprising an effective amount of a CT20p peptide occurs over a pre-determined or definite duration of time. In an aspect, the repeated administration of a CT20p peptide or a composition comprising an effective amount of a CT20p peptide occurs over an indefinite period of time.

In an aspect, a disclosed method of killing cancer cells in a subject further comprises inducing cell death. In an aspect, cell death mimics necrosis. In an aspect, cell death occurs independent of endogenous Bax activity. In an aspect, cell death occurs independent of endogenous caspase activity. In an aspect, cell death is resistant to Bcl-2 over-expression. In an aspect, a disclosed method of killing cancer cells induces cell death, wherein (i) cell death mimics necrosis, (ii) cell death occurs independent of endogenous Bax activity, (iii) cell death occurs independent of endogenous caspase activity, or (iv) cell death is resistant to Bcl-2 over-expression, or (v) cell death exhibits a combination thereof.

In an aspect, a CT20p peptide of a disclosed method of killing cells comprises SEQ ID ID NO: 1, SEQ ID NO: 2, SEQ ID NO: 3, and/or SEQ ID NO: 4. For example, in an aspect, a C-terminal truncated Bax is VTIFVAGVLTASLTIWKKMG (SEQ ID NO: 1). In an aspect, a CT20p peptide is VTIFVAGVLTASLTIWEEMG (SEQ ID NO: 2). In an aspect, a CT20p peptide is VTIFVAGVLTASLTIWLLMG (SEQ ID NO: 3). In an aspect, a CT20p peptide is VTIFVAGVLTASLTIWRRMG (SEQ ID NO: 4). In an aspect, a disclosed composition comprising an effective amount of a CT20p peptide comprises one or more CT20 Bax peptides, wherein the one or more CT20 Bax peptides comprise SEQ ID NO: 1, SEQ NO: 2, SEQ ID NO: 3; or SEQ ID NO: 4.

In an aspect, a CT20p peptide of a disclosed method of killing cancer cells in a subject is encapsulated in polymeric nanoparticles. In an aspect, the nanoparticles are aminated. In an aspect, the nanoparticles are carboxylated.

In an aspect, a disclosed method for killing cancer cells comprising administering a CT20p peptide or a composition comprising an effective amount of a CT20p peptide further comprises administering one or more anti-cancer drugs. In an aspect, the one or more anticancer drugs comprise cisplatin. In an aspect, the one or more anti-cancer drugs induce apoptosis. In an aspect, a disclosed method for killing cancer cells comprising administering a CT20p peptide or a composition comprising an effective amount of a CT20p peptide further comprises administering one or more chemotherapeutic drugs. In an aspect, a disclosed method for killing cancer cells comprising administering a CT20p peptide or a composition comprising an effective amount of a CT20p peptide further comprises administering one or more radiosensitizers.

In an aspect, a disclosed method for killing cancer cells comprising administering a CT20p peptide or a composition comprising an effective amount of a CT20p peptide further comprises administering (i) one or more anti-cancer drugs, (ii) one or more chemotherapeutic drugs, and (iii) one or more radiosensitizers. In an aspect, a disclosed method for killing cancer cells further comprises administering one or more anti-cancer drugs and one or more chemotherapeutic drugs. In an aspect, a disclosed method for killing cancer cells further comprises administering one or more anti-cancer drugs and one or more radiosensitizers. In an aspect, a disclosed method for killing cancer cells further comprises administering one or more chemotherapeutic drugs and one or more radiosensitizers.

In an aspect of a disclosed method of killing cancer cells in a subject, the subject is a mammal. In an aspect, the mammal is a primate. In an aspect, the mammal is a human. In an aspect, the human is a patient.

Disclosed herein is a method of killing cancer cells in a subject comprising (i) administering to a subject an effective amount of a CT20p peptide, (ii) permeabilizing at least one membrane in a cell of the subject, and (iii) inducing cell death.

3. Killing Microbial Cells

Disclosed herein are methods of killing microbial cells.

In an aspect, disclosed herein is a method of killing microbial cells in a subject comprising administering to at least one cell of a subject an effective amount of a CT20p peptide. In an aspect, disclosed herein is a method of killing microbial cells in a subject comprising administering to at least one cell of a subject a composition comprising an effective amount of a CT20p peptide. In an aspect, the cell is a microbial cell, including eukaryotic and prokaryotic cells, such as bacteria and/or fungi. In an aspect, the cell is a drug resistant microbial cell. In an aspect, a CT20p peptide or a composition comprising an effective amount of a CT20p peptide is administered directly.

In an aspect, a disclosed method of killing microbial cells in a subject further comprises permeabilizing at least one membrane in the cell. In an aspect, the membrane is a mitochondrial membrane. In an aspect, the one or more pores are formed in a mitochondrial membrane. In an aspect, the one or more pores are formed in a mitochondrial membrane of a microbial cell.

In an aspect, permeabilizing at least one membrane in the cell comprises destabilizing a cellular membrane, facilitating ion exchange, and causing a sequestered molecule to be released. In an aspect, permeabilizing at least one membrane in the cell comprises destabilizes a cellular membrane. In an aspect, permeabilizing at least one membrane in the cell comprises facilitating ion exchange. In an aspect, permeabilizing at least one membrane in the cell comprises causing a sequestered molecule to be released. In an aspect, permeabilizing at least one membrane in the cell comprises destabilizing a cellular membrane and facilitating ion exchange. In an aspect, permeabilizing at least one membrane in the cell comprises destabilizing a cellular membrane and causing a sequestered molecule to be released. In an aspect, permeabilizing at least one membrane in the cell comprises facilitating ion exchange and causing a sequestered molecule to be released.

In an aspect of a disclosed method of killing microbial cells in a subject, the microbial cells are sensitized to treatment. In an aspect of a disclosed method of killing microbial cells in a subject, the subject is sensitized to treatment. In an aspect, an increased sensitivity or a reduced sensitivity to a treatment, such as a therapeutic treatment, is measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a CT20p peptide or a composition comprising a CT20p peptide to the sensitivity of a cell or subject that has not been administered a CT20p peptide or a composition comprising a CT20p peptide.

For example, in an aspect, following the administration of a CT20p peptide or a composition comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a CT20p peptide or a composition comprising a CT20p peptide. In an aspect, following the administration of a CT20p peptide or a composition comprising a CT20p peptide, the cell is 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a CT20p peptide or a composition comprising a CT20p peptide. The determination of a cell's or a subject's sensitivity or resistance is routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject. In an aspect, data regarding sensitivity or resistance can be acquired at various rather than periodic times. In an aspect, treatment for a subject can be modified based on data regarding a cell's or a subject's sensitivity or resistance to treatment.

In an aspect, a disclosed method of killing microbial cells in a subject further comprises repeating the administration of a CT20p peptide or a composition comprising an effective amount of a CT20p peptide. In an aspect, a CT20p peptide or a composition comprising an effective amount of a CT20p peptide is administered to the subject at least two times. In an aspect, a CT20p peptide or a composition comprising an effective amount of a CT20p peptide is administered to the subject two or more times. In an aspect, a CT20p peptide or a composition comprising an effective amount of a CT20p peptide is administered at routine or regular intervals. For example, in an aspect, a CT20p peptide or a composition comprising an effective amount of a CT20p peptide is administered to the subject one time per day, or two times per day, or three or more times per day. In an aspect, a CT20p peptide or a composition comprising an effective amount of a CT20p peptide is administered to the subject daily, or one time per week, or two times per week, or three or more times per week, etc. In an aspect, a CT20p peptide or a composition comprising an effective amount of a CT20p peptide is administered to the subject weekly, or every other week, or every third week, or every fourth week, etc. In an aspect, a CT20p peptide or a composition comprising an effective amount of a CT20p peptide is administered to the subject monthly, or every other month, or every third month, or every fourth month, etc. In an aspect, the repeated administration of a CT20p peptide or a composition comprising an effective amount of a CT20p peptide occurs over a pre-determined or definite duration of time. In an aspect, the repeated administration of a CT20p peptide or a composition comprising an effective amount of a CT20p peptide occurs over an indefinite period of time.

In an aspect, a disclosed method of killing microbial cells in a subject further comprises inducing cell death. In an aspect, cell death mimics necrosis. In an aspect, cell death occurs independent of endogenous Bax activity. In an aspect, cell death occurs independently of endogenous caspase activity. In an aspect, cell death is resistant to Bcl-2 over-expression. In an aspect, a disclosed method of killing cells induces cell death, wherein (i) cell death mimics necrosis, (ii) cell death occurs independent of endogenous Bax activity, (iii) cell death occurs independent of endogenous caspase activity, or (iv) cell death is resistant to Bcl-2 over-expression, or (v) cell death exhibits a combination thereof.

In an aspect, a CT20p peptide of a disclosed method of killing cells comprises SEQ ID NO: 1, SEQ ID NO: 2, SEQ ID NO: 3, and/or SEQ ID NO: 4. For example, in an aspect, a C-terminal truncated Bax is VTIFVAGVL-TASLTIWKKMG (SEQ ID NO: 1). In an aspect, a CT20p peptide is VTIFVAGVLTASLTIWEEMG (SEQ ID NO: 2). In an aspect, a CT20p peptide is VTIFVAGVL-TASLTIWLLMG (SEQ ID NO: 3). In an aspect, a CT20p peptide is VTIFVAGVLTASLTIWRRMG (SEQ ID NO: 4). In an aspect, a disclosed composition comprising an effective amount of a CT20p peptide comprises one or more CT20 Bax peptides, wherein the one or more CT20 Bax peptides comprise SEQ ID NO: 1, SEQ NO: 2, SEQ ID NO: 3; or SEQ ID NO: 4.

In an aspect, a CT20p peptide of a disclosed method of killing microbial cells in a subject is encapsulated in polymeric nanoparticles. In an aspect, the nanoparticles are aminated. In an aspect, the nanoparticles are carboxylated.

In an aspect, a disclosed method for killing microbial cells comprising administering a CT20p peptide or a composition comprising an effective amount of a CT20p peptide further comprises administering one or more anti-microbial drugs. In an aspect, a disclosed method for killing microbial cells comprising administering a CT20p peptide or a composition comprising an effective amount of a CT20p peptide further comprises administering one or more chemotherapeutic drugs. In an aspect, a disclosed method for killing cancer cells comprising administering a CT20p peptide or a composition comprising an effective amount of a CT20p peptide further comprises administering one or more antimicrobial therapeutics or therapies.

In an aspect of a disclosed method of killing microbial cells in or on a subject, the subject is a mammal. In an aspect, the mammal is a primate. In an aspect, the mammal is a human. In an aspect, the human is a patient.

Disclosed herein is a method of killing microbial cells in a subject comprising (i) administering to a subject an effective amount of a CT20p peptide, (ii) permeabilizing at least one membrane in a cell of the subject, and (iii) inducing cell death.

4. Other Uses

Also disclosed herein are uses of a disclosed composition as an investigational and/or research tool in the development and standardization of in vitro and in vivo test systems for evaluation in laboratory animals such as cats, dogs, rabbits, monkeys, rats and mice, as part of the search for (i) new therapeutic approaches for permeabilizing membranes of cells and for killing cancer or microbial cells as well as (ii) the evaluation of the permeabilization of membranes of cells and for the killing of cancer or microbial cells. In an aspect, the search for new therapeutic approaches and the evaluation of new therapeutic approaches involves a subject, such as a human subject or human patient.

Methods of killing microbial organisms on an inert surface.

The present invention comprises methods of treating a surface to render it antimicrobial, comprising contacting a CT20p peptide composition comprising CT20p peptide to a surface. The peptides may be air-dried and remain on the surface or may be affixed to the surface by binding to other proteins or binding-partners on the surface, or may be attached by adhesive compounds or other compounds known for attaching proteins to a surface, or the peptides may remain in solution in a liquid or semisolid or other form that contacts the surface. The CT20p peptide composition may comprise SEQ ID NO: 1, SEQ ID NO: 2, SEQ ID NO: 3, and/or SEQ ID NO: 4, or a combination of two or more of SEQ ID NOs 1-4. When a surface treated with a CT20p peptide composition comprising one or more CT20p peptides is then contacted by microbial organisms, it is believed that the cellular membranes of the microbial organisms are permeablized and microbial death may occur.

C. Definitions

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value value itself. For example, if the value "10" is disclosed, then "about 10" is also disclosed. It is is also understood that each unit between two particular units are also disclosed. For example, if 10 and 15 are disclosed, then 11, 12, 13, and 14 are also disclosed.

As used herein, the amino acid abbreviations are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

"Peptide" as used herein refers to any peptide, oligopeptide, polypeptide, gene product, expression product, or protein. For example, a peptide can be a fragment of a full-length protein, such as, for example, the CT20 Bax peptide. A peptide is comprised of consecutive amino acids. The term "peptide" encompasses naturally occurring or synthetic molecules.

In general, the biological activity or biological action of a peptide refers to any function exhibited or performed by the peptide that is ascribed to the naturally occurring form of the peptide as measured or observed in vivo (i.e., in the natural physiological environment of the protein) or in vitro (i.e., under laboratory conditions). For example, a biological activity of the CT20p peptide is the cytotoxic activity of the CT20 Bax peptide.

The term "enzyme" as used herein refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as those disclosed herein.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc for both eukaryotic and prokaryotic cells. The art is familiar with such compositions, methods, techniques, etc. for the optimization of the introduction and expression of a nucleic acid into and within a recipient cell.

As used herein, "a CT20p peptide" may refer to one peptide or may refer one or more peptides, such as molar concentrations of the peptide, as would be found in a composition. Those skilled in the art understand where an individual peptide is intended and where a molar, or smaller or larger amount, of many of the same peptide are intended.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In some aspects of the disclosed methods, the subject has been diagnosed with a need for treatment for cancer and/or aberrant cell growth.

Therapeutic agents may include antimicrobial agents, such as antibiotics or antimycotic compounds, including but not limited to, active agents such as antifungal agents, antibacterial agents, anti-viral agents and antiparasitic agents, and metals. An antimicrobial agent may comprise a substance, compound or molecule, that kills or inhibits the growth of microorganisms such as bacteria, fungi, or protozoans. Antimicrobial agents may either kill microbes (microbiocidal) or prevent the growth of microbes (microbiostatic). Disinfectants are antimicrobial substances used on non-living objects or outside the body. Anitmicrobial agents include those obtained from natural sources, such as Beta-lactam antibiotics (such as penicillins, cephalosporins), and protein synthesis inhibitors (such as aminoglycosides, macrolides, tetracyclines, chloramphenicol, polypeptides), and those from synthetic sources such as sulphonamides, cotrimoxazole, quinolones, anti-fungals, anti-cancer drugs, antimalarials, anti-tuberculosis drugs, anti-leprotics, and anti-protozoals.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ainpicillin, amphotericin B, ketoconazole, fluconazole, pyrimethaniine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms. As used herein, the term metal includes all metal salts or metal compounds, including, but not limited to, metal chlorides, metal phosphates, metal sulfates, metal iodides or metal bromides. The active form of some metal salts is the ionic form. Other antimicrobial agents include, but are not limited to, polyene antifungals, Amphotericin B, Candicidin, Filipin, Hamycin, Natamycin, Nystatin, Rimocidin, Imidazoles, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Triazoles, Albaconazole, Fluconazole, Isavuconazole, Itraconazole, Posaconazole, Ravuconazole, Terconazole, Voriconazole, Thiazoles, Abafungin, Allylamines, Amorolfin, Butenafine, Naftifine, Terbinafine, chinocandins, Anidulafungin, Caspofungin, Micafungin.

Examples of microbial organisms that may be treated by the present invention include, but are not limited to, pathogenic fungi including, but not limited to, Candida species, Aspergillus species, Cryptococcus species, histoplasa species, stachybotrus species, and pneumacystus species; bacteria including but not limited to:

| | |
|---|---|
| *Acetobacter aurantius* | *Calymmatobacterium granulomatis* |
| *Acinetobacter baumannii* | *Campylobacter* |
| *Actinomyces israelii* | *Campylobacter coli* |
| *Agrobacterium radiobacter* | *Campylobacter fetus* |
| *Agrobacterium tumefaciens* | *Campylobacter jejuni* |
| *Azorhizobium caulinodans* | *Campylobacter pylori* |
| *Azotobacter vinelandii* | *Chlamydia* |
| *Anaplasma* | *Chlamydia trachomatis* |
| *Anaplasma phagocytophilum* | *Chlamydophila* |
| *Acetobacter aurantius* | *Chlamydophila pneumoniae* |
| *Bacillus* | *Chlamydophila psittaci* |
| *Bacillus anthracis* | *Clostridium* |

-continued

| | |
|---|---|
| Bacillus brevis | Clostridium botulinum |
| Bacillus cereus | Clostridium difficile |
| Bacillus msiformis | Clostridium perfringens |
| Bacillus liclieniformis | Clostridium tetani |
| Bacillus megaterium | Corynebacterium |
| Bacillus mycoides | Corynebacterium diphtheriae |
| Bacillus stearothermophilus | Corynebacterium fusiforme |
| Bacillus subtilis | Coxiella burnetii |
| Bacteroides | Ehrlichia chaffeensis |
| Bacteroides fragilis | Enterobacter cloacae |
| Bacteroides gingivalis | Enterococcus |
| Bacteroides melaninogenicus | Enterococcus avium |
| Bartonella | Enterococcus durans |
| Bartonella henselae | Enterococcus faecalis |
| Bartonella quintana | Enterococcus faecium |
| Bordetella | Enterococcus galllinarum |
| Bordetella bronchiseptica | Enterococcus maloratus |
| Bordetella pertussis | Escherichia coli |
| Borrelia burgdorferi | Francisella tularensis |
| Brucella | Fusobacterium nucleatum |
| Brucella abortus | Haemophilus |
| Brucella melitensis | Haemophilus ducreyi |
| Gardnerella vaginalis | Haemophilus influenzae |
| Klebsiella pneumoniae | Haemophilus parainfluenzae |
| Lactobacillus | Haemophilus pertussis |
| Lactobacillus acidophilus | Haemophilus vaginalis |
| Lactobacillus casei | Helicobacter pylori |
| Lactococcus lactis | Neisseria |
| Legionella pneumophila | Neisseria gonorrhoeae |
| Listeria monocytogenes | Neisseria meningitidis |
| Lactobacillus Bulgaricus | Rhizobium radiobacter |
| Mycoplasma | Rickettsia |
| Mycoplasma fermentans | Rickettsia prowazekii |
| Mycoplasma genitalium | Rickettsia psittaci |
| Mycoplasma hominis | Rickettsia quintana |
| Mycoplasma penetrans | Rickettsia rickettsii |
| Mycoplasma pneumoniae | Rickettsia trachomae |
| Metlianobacterium extroquens | Rochalimaea |
| Microbacterium multiforme | Rochalimaea henselae |
| Micrococcus luteus | Rochalimaea quintana |
| Moraxella catarrhalis | Rothia dentocariosa |
| Mycobacterium | Rhizobium radiobacter |
| Mycobacterium avium | Salmonella |
| Mycobacterium bovis | Salmonella enteritidis |
| Mycobacterium diphtheriae | Salmonella typhi |
| Mycobacterium intracellulare | Salmonella typhimurium |
| Mycobacterium leprae | Serratia marcescens |
| Mycobacterium lepraemurium | Shigella dysenteriae |
| Mycobacterium phlei | Staphylococcus |
| Mycobacterium smegmatis | Staphylococcus aureus |
| Mycobacterium tuberculosis | Staphylococcus epidermidis |
| Pasteurella | Stenotrophomonas maltophilia |
| Pasteurella multocida | Streptococcus |
| Pasteurella tularensis | Streptococcus agalactiae |
| Peptostreptococcus | Streptococcus avium |
| Porphyromonas gingivalis | Streptococcus bovis |
| Pseudomonas aeruginosa | Streptococcus cricetus |
| Streptococcus mitior | Streptococcus faceium |
| Streptococcus mitis | Streptococcus faecalis |
| Streptococcus mutans | Streptococcus ferus |
| Streptococcus oralis | Streptococcus gallinarum |
| Streptococcus pneumoniae | Streptococcus lactis |
| Streptococcus pyogenes | Streptococcus sanguis |
| Streptococcus rattus | Streptococcus sobrinus |
| Streptococcus salivarius | Wolbachia |
| Treponema | Vibrio parahaemolyticus |
| Treponema pallidum | Vibrio vulnificus |
| Treponema denticola | Yersinia |
| Vibrio | Yersinia enterocolitica |
| Vibrio cholerae | Yersinia pestis |
| Vibrio comma | Yersinia pseudotuberculosis |

The terms "treating", "treatment", "therapy", and "therapeutic treatment" as used herein refer to curative therapy, prophylactic therapy, or preventative therapy. As used herein, the terms refers to the medical management of a subject or a patient with the intent to cure, ameliorate, stabilize, or prevent a disease, pathological condition, or disorder, such as, for example, cancer or a tumor. This term includes active treatment, that is, treatment directed directed specifically toward the improvement of a disease, pathological condition, or disorder, disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the disease, pathological condition, or disorder is cancer, such as, for example, breast cancer, lung cancer, colorectal, liver cancer, or pancreatic cancer.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician or a researcher, and found to have a condition that can be diagnosed or treated by compositions or methods disclosed herein. For example, "diagnosed with cancer" means having been subjected to a physical examination by a person of skill, for example, a physician or a researcher, and found to have a condition that can be diagnosed or treated by a compound or composition that alleviates or ameliorates cancer and/or aberrant cell growth.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer and/or aberrant cell growth) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a peptide (such as a CT20 Bax peptide), or a composition (such as a composition comprising a CT20 Bax peptide), or pharmaceutical preparation (such as a preparation comprising a CT20p peptide or a composition comprising a CT20 Bax peptide) to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intraarterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level, e.g., of a nucleotide or transcript or polypeptide. For example, determining the amount of a disclosed transcript or polypeptide in a sample as used herein can refer to the steps that the skilled person would take to measure or ascertain some quantifiable value of the transcript or polypeptide in the sample. The art is familiar with the ways to measure an amount of the disclosed nucleotides, transcripts, polypeptides, etc.

In an aspect, "determining" as used herein can refer to measuring or ascertaining the level of cell death or cell survival, for example, following administration of a CT20p peptide or a composition comprising an effective amount of a CT20p peptide. Methods of measuring or ascertaining cell survival and cell death are known to the art and include, but are not limited to, histochemical staining (e.g., TUNEL), cell proliferation assay, cell death assays, morphological examination, etc. In an aspect, the size of a tumor can be measured non-invasively through ultrasound.

As used herein, the term "level" refers to the amount of a target molecule in a sample, e.g., a sample from a subject. The amount of the molecule can be determined by any method known in the art and will depend in part on the nature of the molecule (i.e., gene, mRNA, cDNA, protein, enzyme, etc.). The art is familiar with quantification methods for nucleotides (e.g., genes, cDNA, mRNA, etc) as well as proteins, polypeptides, enzymes, etc. It is understood that the amount or level of a molecule in a sample need not be determined in absolute terms, but can be determined in relative terms (e.g., when compare to a control or a sham or an untreated sample).

As used herein, the terms "effective amount" and "amount effective" refer to an amount that is sufficient to achieve the desired result or to have an effect on an undesired condition. For example, in an aspect, an effective amount of a CT20p peptideis an amount that permeabilizes cell membranes and/or kills cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental coincidental with the specific compound employed and like factors well known in the medical medical arts.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

As used herein, "$EC_{50}$," is intended to refer to the concentration or dose of a substance (e.g., a CT20p peptide or a disclosed composition comprising a CT20p peptide) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured cancer cells or in an ex vivo organ culture system with isolated cancer cells, e.g., pancreatic cancer cells, breast cancer cells, liver cancer cells, lung cancer cells, colorectal cancer cells, etc.). Alternatively, the response can be measured in vivo using an appropriate research model such as rodent, including mice and rats. The mouse or rat can be an inbred strain with phenotypic characteristics of interest such as, for example, cancer and/or aberrant cell growth. As appropriate, the response can be measured in a transgenic or knockout mouse or rat wherein a gene or genes has been introduced or knocked-out, as appropriate, to replicate a disease process.

As used herein, "$IC_{50}$," is intended to refer to the concentration or dose of a substance (e.g., a CT20p peptide or a disclosed composition comprising a CT20p peptide) that is required for 50% inhibition or diminution of a biological process, or component of a process, including a protein, subunit, organelle, ribonucleoprotein, etc. $IC_{50}$ also refers to the concentration or dose of a substance that is required for 50% inhibition or diminution in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured cancer cells or in an ex vivo organ culture system with isolated cancer cells (e.g., breast cancer cells, pancreatic cancer cells, liver cancer cells, lung cancer cells, colorectal cancer cells, etc.). Alternatively, the response can be measured in vivo using an appropriate research model such as rodent, including mice and rats. The mouse or rat can be an inbred strain with phenotypic characteristics of interest such as, for example, cancer and/or aberrant cell growth. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and may be divided into different subtypes based on their biological characteristics. Cancer includes, but is not limited to, melanoma, leukemia, astocytoma, glioblastoma, lymphoma, glioma, Hodgkins lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

As used herein, the term "sensitizing" refers to an increased sensitivity of a cell or a subject to a treatment, such as a therapeutic treatment. The term "sensitizing" also refers to a reduction or decrease in the resistance of a cancer cell or a subject with cancer in responding to a therapeutic treatment. An increased sensitivity or a reduced sensitivity to a therapeutic treatment is measured according to a known method in the art for the particular treatment and methods including, but not limited to, cell proliferation assays and cell death assays. The sensitivity or resistance may also be measured in a subject by measuring the tumor size reduction over a period of time, such as, for example, every 1 to 3 to 6 month for a human subject and every 2 to 4 to 6 weeks for non-human subject (e.g., mouse or rat). The sensitivity of a cell or a subject to treatment can be measured or determined by comparing the sensitivity of a cell or a subject following administration of a CT20p peptide or a composition comprising an effective amount of a CT20p peptide to the sensitivity of a cell or subject that has not been administered a CT20p peptide or a composition comprising an effective amount of a CT20p peptide.

As used herein, the term "anti-cancer" or "anti-neoplastic" drug refers to one or more drugs that can be used in conjunction with a CT20p peptide or a composition comprising an effective amount of a CT20p peptide to treat cancer and/or aberrant cell growth. Examples of anti-cancer drugs or anti-neoplastic drugs include, but are not limited to, the following: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma 1 b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclizimab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocanycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A +myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone +pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor;platinum complex; platinum compounds; platinum-triamine complex; porfimer sodium; porfiromycin; propyl bis-acridone; prostaglandin J2; proteasome inhibitors; protein A-based immune modulator; protein kinase C inhibitors; microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

As used herein, radiosensitizers make a cancer cell more likely to be damaged. Radiosensitizers enhance the sensitivity of cancer cells and/or a tumor to ionizing radiation, thereby increasing the efficacy of radiotherapy. Examples of radiosensitizers include gemcitabine, 5-fluorouracil, pentoxifylline, and vinorelbine.

The majority of chemotherapeutic drugs can be divided in to: alkylating agents (e.g., cisplatin, carboplatin, oxaliplatin, mechloethamine, cyclophosphamide, chlorambucil, antimetabolites (e.g., azathioprine, mercaptopurine), anthracyclines, plant alkaloids and terpenoids (e.g., vinca alkaloids (e.g., vincristine, vinblastine, vinorelbine, vindesine, and podophyllotoxin) and taxanes (e.g., paclitaxel and docetaxel), topoisomerase inhibitors (e.g., irinotecan, topotecan, amsacrine, etoposide, etoposide phosphate, and teniposide), monoclonal antibodies (e.g., trastuzumab, cetuximab, rituximab, bevacizumab), other antitumour agents (e.g., dactinomycin), and hormonal therapy (e.g., steroids such as dexamethasone), finasteride, aromatase inhibitors, and gonadotropin-releasing hormone agonists).

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods methods of making and using the compositions of the invention. Thus, if there are a variety of of additional steps that can be performed it is understood that each of these additional steps can be performed with any specific embodiment or combination of embodiments of the methods of the invention.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of, and "consisting of can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

D. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Experiments a. Establishment of Cell Lines

The Flp-In T-REx-293 cell line (Invitrogen) stably expressed the lacZ-Zeocin fusion gene and Tet repressor. The 293 line was maintained in Dulbecco's Modified Eagle Medium (DMEM), 10% fetal bovine serum (FBS) (tetracycline-reduced), 2 mM L-glutamine and 1% Penicillin-Streptomycin. The HCT-116 $Bax^{-/-}$ and $Bax^{+/+}$ colorectal cancer cell lines (Zhang et al., 2000) were maintained in McCoy's 5A media, 10% FBS, and 1% Penicillin-Streptomycin. The breast cancer cell lines, MCF-7 and MCB-MD-231 (ATCC), were maintained in DMEM, 10% FBS, and 1% Penicillin-Streptomycin. MCF-7 cells were supplemented with 1% L-Glutamine every 15 days. Early passages of all cell lines were frozen as stocks at time of receipt. Cell lines were used at less than 10 passages from stocks.

b. Generation of the CT20 Bax Peptide

The CT20p peptide (Ac-VITFVAGVLTASLTIWKKMG-NH2) (Biopeptide Co., Inc.) (SEQ ID NO:53) was commercially synthesized at >98% purity.

c. Generation of Plasmids for Mutagenesis and Transfection

For inducible expression of Bax, the Flp-In T-REx System (Invitrogen) was utilized according to the manufacturer's protocol. Briefly, PCR-directed mutagenesis of K189/K190 was performed using HA-tagged primer sets (Table 1). Bax constructs were amplified from pEGFP-Bax, digested with EcoRV, and cloned into the plasmid pcDNA5/FRT/TO, which undergoes DNA recombination at the Flp Recombination Target (FRT) site when co-expressed with the Flp recombinase pOG44 plasmid. Constructs were confirmed by sequencing. Fugene transfection reagent (Roche) was used to co-transfect plasmids at a ratio of 9:1. Stable Flp-In T-REx expression cell lines were selected for Blasticidin resistance (10 µg/mL), Hygromycin resistance (100 µg/mL) and Zeocin sensitivity (200 µg/mL). Bax expression was induced with 1 µg/mL tetracycline. Cells were assayed after 24 hours of induction. See Table 1 for sequences and primers used herein.

To generate the Destabilization Domain (DD)-tagged Bax CT (amino acids 173-192) fusion proteins with K189/K190 (wild-type) or EE, LL, and RR mutations, primers (Table 1) were annealed and ligated into the ProteoTuner vector (Clontech) digested by EcoRI and BamHI. Generation of DD-tagged, full-length WT Bax was previously described (Boohaker et al., 2011). The ProteoTuner IRES2 system (Clontech) also had the marker protein GFP downstream to the internal ribosome entry sequence (IRES) and was translated independently of the DD-tagged protein. Cells were transiently transfected using the TransIT-LT1 transfection reagent (Minis) for 24 hours and microscopically assayed for GFP expression. Expression of DD-tagged proteins was induced for 4-5 hours by adding 500 nM of Shield (Clontech).

MDA-MB-231 cells were transiently transfected with pcDNA-Bcl2 (or as control pEGFP (Clontech)) using the TransIT-LT1 transfection reagent (Minis). To assess transfection efficiency, cells were assayed microscopically for EGFP expression. To assess Bcl-2 expression, cells lysates were immunoblotted.

d. Detection of Mitochondrial Translocation

Mitochondrial and cytosolic proteins were isolated using a mitochondrial enrichment kit (Pierce). Western blots were run using 12-15% SDS-PAGE gels and PVDF membranes and probed with the following primary antibodies: 16B12 anti-HA mouse monoclonal (Covance) for HA-tagged Bax; 631073Anti-DD monoclonal (Clontech) for DD-Bax; N-20 (Santa Cruz) for endogenous Bax; Ab-2 (Fitzgerald) for prohibitin; C20 (MAPK) (Santa Cruz) for p38 MAP kinase; and rabbit polyclonal for Bcl-2 (Santa Cruz). The appropriate secondary antibodies conjugated to horseradish peroxidase (HRP) was then used and visualized with enhanced chemiluminescence kit (Pierce). Molecular weight markers (SeeBlue Plus 2 (Invitrogen)) were used to approximate the position of protein bands in blots.

e. Co-Localization of Mitochondrial Proteins

To determine whether expression of DD-tagged Bax C-terminal peptides co-localized with mitochondria, $Bax^{+/+}$ HCT-116 cells and $Bax^{-/-}$ HCT-116 cells were cultured for 24 hours on coverslips pretreated with laminin. The DD-Bax C-terminal WT peptide and DD-Bax C-terminal EE, LL, and RR mutations constructs were transfected into the cells using Minis LT-1 reagent according manufacturer's protocol. After 24 hours, expression of the transfected peptides was induced by the addition of shield 1 for 4 hrs. Cells were fixed with 2% w/v formaldehyde/PBS for 15 minutes and permeabilized using 0.05% Triton X-100/PBS for 15 minutes. After washing, cells were incubated with primary antibodies HSP60 (H-300, Santa Cruz) and DD monoclonal antibody for 1 hour at room temperature, which was followed by incubation with secondary anti-rabbit-Cy3 (81-6115, Invitrogen) and anti-mouse-Texas red (715076020, Jackson Immunoresearch) for 30 minutes. After the final wash, cells were mounted with gel/mount medium (Mol, Biomeda) and images were acquired with UltraView (PerkinElmer) microscopy with a plan-apochromat 63×/1.4 oil objective. The scanned images were processed and Pearson's correlation coefficients determined using Velocity Version 5.5 (Perkin Elmer).

f. Generation and Expression of EGFP-CT20p Peptide Fusion Constructs

To generate the EGFP-CT20p peptide fusion proteins, primers incorporating the CT (amino acids 173-192) of Bax with mutations targeting K189/K190 (Table 1) were used to amplify EGFP from the template pEGFP (Clontech). The PCR insert was cloned into pcDNA5/FRT/TO as previously above. HCT-116 cells were transiently transfected using the TransIT-LT1 transfection reagent (Minis) and cells assayed microscopically for EGFP expression up to 12 hours later.

g. Confocal Imaging of Live Cells

Images were acquired through a PerkinElmer UltraView spinning disc confocal system with AxioObserver.Z1 stand (Carl Zeiss) in a humidity and temperature-controlled chamber (LiveCell) with cells cultured on MatTek plates (MatTek Corporation). Post-acquisition snapshots were taken from time-lapse movies at time points indicated in the figures. For EGFP-CT20 Bax fusion proteins, time-lapse movies were initiated two hours after transfection and images acquired through 12 hours of expression using a Plan-Apochromat 10× objective. For DD-CT20 Bax fusion proteins, cells were incubated with 1 nM MitoTracker Red 580 for 30 minutes prior to imaging. Time-lapse movies were recorded for up to 12 hours using a Plan-Apochromat 63× Oil DIC objective.

Visualization of the uptake and effects of the fluorescent dye (DiI)-loaded nanoparticles in HCT-116, MCF-7, and MDA-MD-231 cells was observed using a 10× air objective with a numerical aperture of 0.3, using ex/em of 514/587. All cells were loaded with MitoTracker. Visualization of the HCT-116 cell lines was observed using Plan-Apochromat 63× Oil objective. MCF-7 and MDA-MB-231 images were captured using Plan-Apochromat 40× Oil objective. All time-lapse images were generated in 2D by capturing 6 time points per hour for 24 hours of the same field.

h. Treatments and Detection of Apoptotic Cells by Flow Cytometry

HCT-116, MCF-7, or MDA-MB-231 cells were collected at a final concentration of $1 \times 10^6$ cells/mL and assayed using the SYTOX® AADvanced™ dead cell stain solution (Invitrogen). Cells were analyzed using the BD FACSCanto flow cytometer. SYTOX® AADvanced™ was visualized at 488 nm and emissions collected at 695 nm. Analysis of data was done using FSC Express software (DeNovo). Membrane asymmetry was assessed using the Violet Ratiometric Membrane Asymmetry Probe/Dead Cell Apoptosis Kit (Invitrogen) according to the manufacturer's protocol.

To evaluate apoptosis, cells were pre-treated with 100 µM of the pan-caspase inhibitor Z-VAD-fmk (EMD Biosciences) or transiently transfected with Bcl-2, then treated with either CT20/nanoparticles or cisplatin (CDDP) alone or in combination as indicated in figure legends. Following treatment, cells were analyzed for cell death and membrane asymmetry.

i. Synthesis of Polymeric Nanoparticles Encapsulating the Bax CT20 Bax Peptide

The Bax CT20p peptidewas encapsulated into hyperbranched polymeric (HBPE) nanoparticles following a previously reported method (Santra et al., 2010). A fluorescent dye (DiI) was co-encapsulated with the peptide. In brief, 1.0 µL, of DiI dye (10 µg/µL) and 36 µL, of CT20p peptide (0.05 µg/µL) solution in 250 µL, of DMSO were mixed in 250 µL of a DMSO solution containing the HBPE polymer (12 mg) for a ratio of ~0.15 µg peptide: 1 mg nanoparticles. The resulting polymer-DiI/Bax mixture in DMSO was added to deionized water (2.5 mL) to form the HBPE (Bax CT20/DiI) nanoparticles. The resulting nanoparticles were purified using a PD-10 column and dialyzed (MWCO 6-8K) against PBS (pH=7.4). Dynamic light scattering and zeta potential analysis of the nanoparticle reveals a size diameter of 88±2 nm and zeta potential of −54.5 mV.

j. Synthesis of Aminated Polymeric Nanoparticles Encapsulating the CT20 Bax Peptide The HBPE nanoparticles contain functional carboxylic groups on their surface that resulted in a negative charge. To introduce a positively charged surface, the nanoparticles were aminated using water-soluble carbodiimide chemistry [EDC: 1-ethyl-3-(3-dimethylamino-propyl) carbodiimide hydrochloride and NHS: N-hydroxysuccinimide chemistry], following a previously reported method (Santra et al., 2010). Briefly, to a solution of HBPE (Bax CT20/DiI) nanoparticles (1.0 mmol) in PBS (pH=7.4), a solution of EDC (10 mmol) and NHS (10 mmol) in MES buffer (pH=6.0) was added. Afterwards, ethylenediamine (10 mmol) in DMSO was added to obtain aminated DiI/Bax co-encapsulation polymeric nanoparticles (PNPs), which were purified and dialyzed. Dynamic light scattering and zeta potential analysis of the nanoparticle reveals a nanoparticle size diameter or 91±3 nm and zeta potential of +10.3 mV. All nanoparticles were stored at 4° C. A final working concentration of 350 pM was determined by testing the toxicity of 7 nM, 1.4 nM, 0.7 nM, and 0.35 nM using HCT-116$^{+/+}$ cells.

k. Determination of Calcein Release

Calcein release from artificial membranes was measured on a JASCO 810 spectropolarimeter (Jasco Inc.) with a Peltier water cooled thermostat and a photomultiplier tube mounted at 90 degrees for fluorescence measurements. Large unilamellar vesicles (LUVs) were prepared with the following modifications: Lipids (Avanti Polar Lipids) in chloroform were mixed in the following molar ratios: 52.5% 1-palmitoyl-2-oleyl-sn-glycero-3-phosphatidylcholine (POPC), 21% 1-palmitoyl-2-oleyl-sn-glycero-3-phosphatidylethanolamine (POPE), 13% bovine liver L-α phosphatidylinositol (PI), 10% cholesterol and 3.5% 1-palmitoyl-2-oleyl-sn-glycero-3-phosphatidylglycerol (POPG). These rations mimicked the outer mitochondrial membrane. After removing chloroform and desiccating, the dried lipid film was resuspended in 50 mM HEPES, pH 7, supplemented with 110 mM NaCl and 80 mM calcein and extruded with Avanti's mini extruder (Alabaster, Ala.). External calcein was removed by gel filtration through a 1.5×50 cm Econo-Column (Bio-Rad) freshly packed with Sephadex 50 (GE Healthcare). CT20 Bax peptides were added at concentrations equivalent to those used with cells in culture. Calcein fluorescence was excited at 495 nm and emission spectra recorded between 510 and 550 nm (excitation/ emission slits: 10/3 nm). Samples were maintained at 37° C. and a final measurement taken at 24 hours. Maximum calcein release was obtained by the addition of Triton ×100 (0.1% final concentration) to calcein loaded LUVs without nanoparticles that had had been incubated at 37° C. for 24 hours after the addition of 10 µL DMSO.

1. In Vivo Experiments

One to two million MBA-MD-231 cells were harvested from culture and injected subcutaneously into the right and left flanks of 16 female nude mice (nu/nu, Charles River). After 2-3 weeks, tumor volume and growth was assessed by ultrasound (VisualSonics Vevo 2100). Mice with tumors were injected intratumorally with PBS, unloaded polymeric nanoparticles, or CT20 Bax peptide-loaded polymeric nanoparticles at 4× the concentrations described above. Injections were performed twice over a 4-5 day period. Mice were observed 0-5 days post-treatments and tumor volume assessed by ultrasound.

2. C-Terminal α9 Helix of Bax Enables Membrane Binding and Permeabilization

To develop a novel anti-cancer agent that could be used to sensitize cancer cells to treatment, the death-inducing activity of Bax was examined. The protein's C-terminal domain was a point of focus because of its putative membrane-binding properties (Ausili et al., 2008; Martinez-Senac et al., 2001; Nechushtan et al., 1999; Schinzel et al., 2004). Mutagenesis of the C-terminus of full-length Bax was performed (Table 2). As the constitutive expression of N-terminal-tagged Bax induced spontaneous cell death. To avoid this, full-length HA-tagged Bax was expressed in stably transfected Flp-In T-REx 293 cells. Bax constructs were integrated into the genome at a single FRT (recombination) site and the levels of Bax expression in these isogenic cell lines did not cause apoptosis. These experiments determined the role of the C-terminus and amino acids K189/K190 in the localization of Bax under normal cellular conditions.

TABLE 2

Effect of K189/K190 Mutations on Bax Intracellular Localization.

| Bax C-terminus | Residues (189-190-191-192) | SEQ ID NO | Cellular Localization |
|---|---|---|---|
| Wild Type | KKMG | 54 | Cyto > Mito |
| (+) to hydrophobic | LKMG | 55 | Mito |
|  | KLMG | 56 |  |
|  | LLMG | 57 |  |
| (+) to (−) charge reversal | EKMG | 58 | Cytosol |
|  | KEMK | 59 |  |
|  | EEMG | 60 |  |
| (+) to polar | QQMG | 61 | Cyto = Mito |
| (+) to (−) charge reversal | DDMG | 62 | Cytosol |
| Increase (+) charge, length | RRMG | 63 | Mito |
| Rearrangement of (++) | KMGK | 64 | Cyto = Mito |
| Deletion of (+) | -KMG |  | Cyto = Mito |
| Deletion of (+) and rearrangement | -MGK |  | Cytosol |

Localization of full-length, wild-type (WT) Bax (Bax-KK) was distributed among cytosolic and mitochondrial lysates (FIG. 1A). Specifically, mitochondrial translocation of HA-tagged wild type Bax (Bax-KK) and K189/K190 mutants, expressed in 293 cells using the Flp-In T-Rex system, was examined by immunoblot. p38 MAPK and prohibitin were blotted for cytosolic and mitochondrial content, respectively. Data are representative of five independent assays. Images from full-length blots were cropped for concise presentation. N-terminal-deleted Bax (Bax-ΔNT) was localized primarily to mitochondria while the C-terminal-deleted Bax (Bax-ΔCT) was retained in the cytosol. These data indicate the role of the N- and C-terminal domains in Bax localization (FIG. 1A).

Figure 1B:
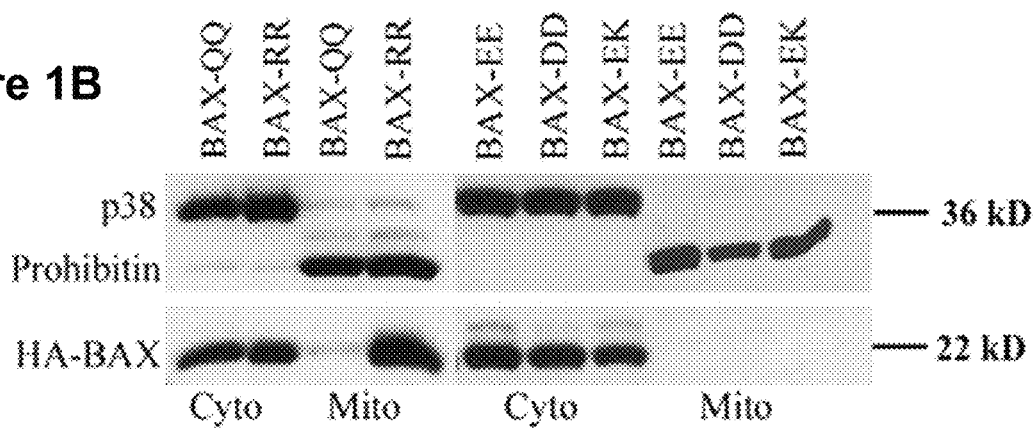

Substitution of K189/K190 with negatively charged residues, aspartic acid (D) or glutamic acid (E), resulted in the cytosolic retention of Bax (Bax-DD, Bax-EE) (FIG. 1B). Substitution of K189/K190 with positively charged arginine (R) (Bax-RR) led to mitochondrial localization (FIG. 1B). Substitution of K189/K190 with a polar amino acid, glutamine (Q) (Bax-QQ), led to less mitochondrial Bax, when compared Bax-KK and Bax-RR (FIGS. 1A and 1B). Substitution of K189/K190 with the hydrophobic amino acid leucine (L) (Bax-LL) resulted in mitochondrial association (FIG. 1A). Mutation of K189 (Bax-EK) also rendered Bax cytosolic, which was not observed by mutation of K190 (Bax-KMGK) (FIGS. 1A and 1B, Table 2). These results demonstrated that the C-terminus of Bax, and K189/K190, modulated the association of the full-length protein with mitochondria.

Figure 1C:
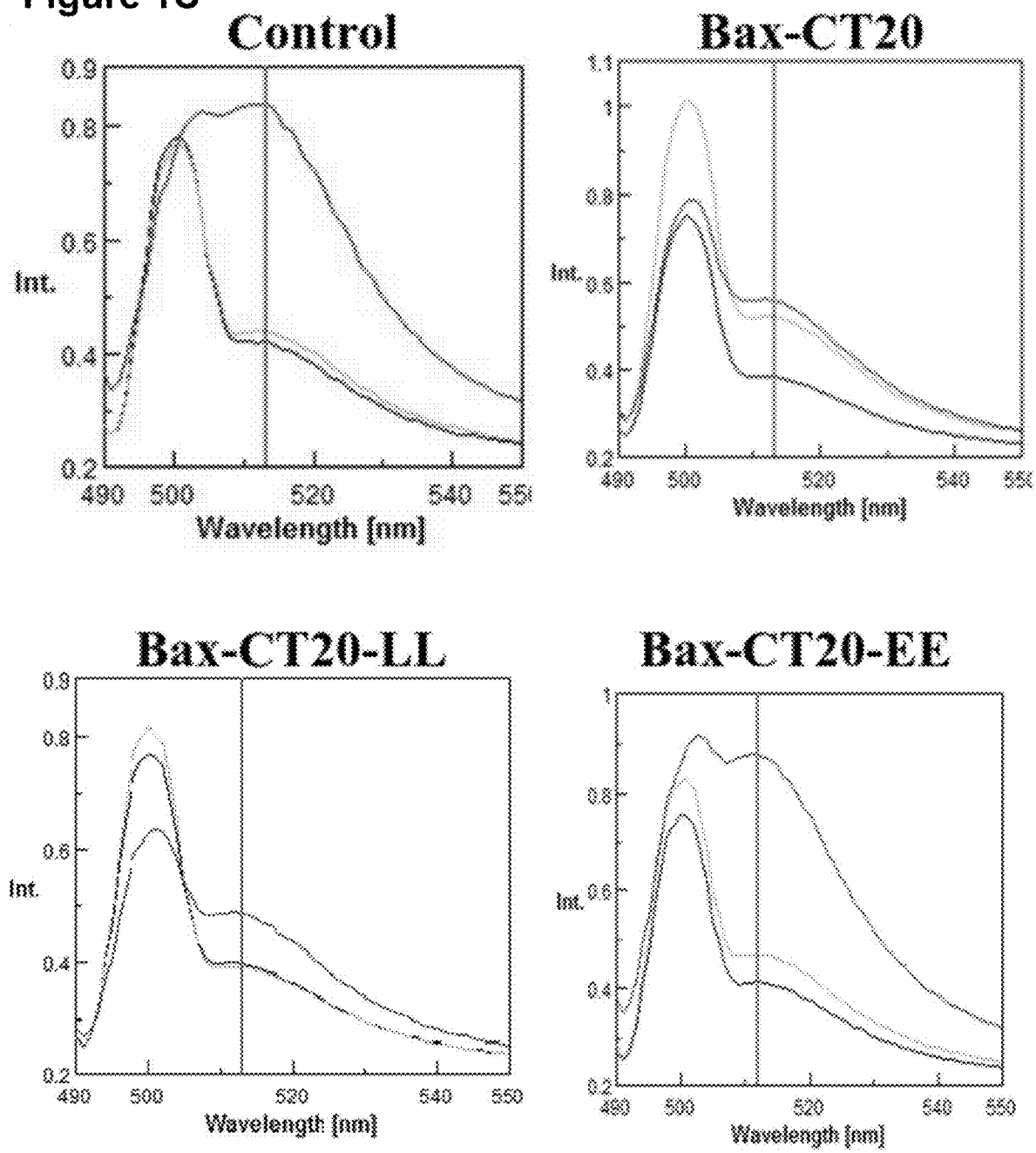
FIG. 1C shows the results of the analysis of the effects of mutations in Bax demonstrating that the C-terminus of Bax mediates membrane permeablization.

Analysis of the effects of mutations of K189/K190 in full-length Bax indicated that the C-terminal domain was a preferred region from which to fashion a membrane-binding and possibly a membrane-permeabilizing peptide. Using a commercially synthesized peptide composed of the last twenty amino acids (172-192) of the C-terminus of Bax (CT20), the ability of CT20p peptideto insert and permeabilize lipid membranes was examined. Liposomes contained phospholipids that composed the mitochondrial outer membrane and were loaded with calcein. FIG. 1C demonstrates that the CT20p peptideinserted itself into mitochondrial-like lipid vesicles and caused the release of calcein. In FIG. 1C, the red lines indicate maximal release of calcein with Triton X-100. The blue lines indicate treatment with DMSO and the green lines (except for control) indicate treatment with CT20 Bax peptides. A mutant CT20 Bax peptide, in which the terminal lysines (K189/K190 in the full-length protein) were exchanged with leucine (LL) or aspartic acid (EE), did not cause calcein release. This indicated that the original lysines at positions 189 and 190 were required for optimal membrane permeabilization. CT20 Bax or mutant CT20-LL peptides stabilized the lipid membranes and impaired the maximal release of calcein upon treatment with detergent (FIG. 1C). However, this did not occur with the CT20-EE peptide, indicating that the amino acid sequence of the peptide dictated the nature of the interaction with lipid membranes. These data demonstrated that the CT20 peptide bound to lipid membranes and caused the release of vesicular contents, and further demonstrated that the CT20p peptideadded rigidity or structure to the lipid membranes.

3. Expression of the CT20p Peptide Induces Cell Death

Having established the importance of the C-terminal domain of Bax in the intracellular localization of the protein and demonstrated the membrane-binding and permeabilization properties of the CT20 Bax peptide, the capacity of the CT20p peptide to induce cell death was next evaluated. Specifically, whether the CT20p peptide had cytotoxic properties based on its capacity to associate with lipid membranes of organelles like mitochondria was assessed. The CT20p peptide domain was fused to a short destabilization domain (DD) for detection and inducible expression. The CT20p peptide fused to DD (DD-CT20) was inducibly expressed in HCT-116 cells and peptide localization and induction of cell death was examined. For a control, the action of the DD-CT20 (KK and EE, LL and RR mutants) peptides to DD-tagged full-length (FL) Bax was compared. Induced expression of DD-FL Bax did not cause cell death in the absence of apoptotic stimuli.

Figure 2A:
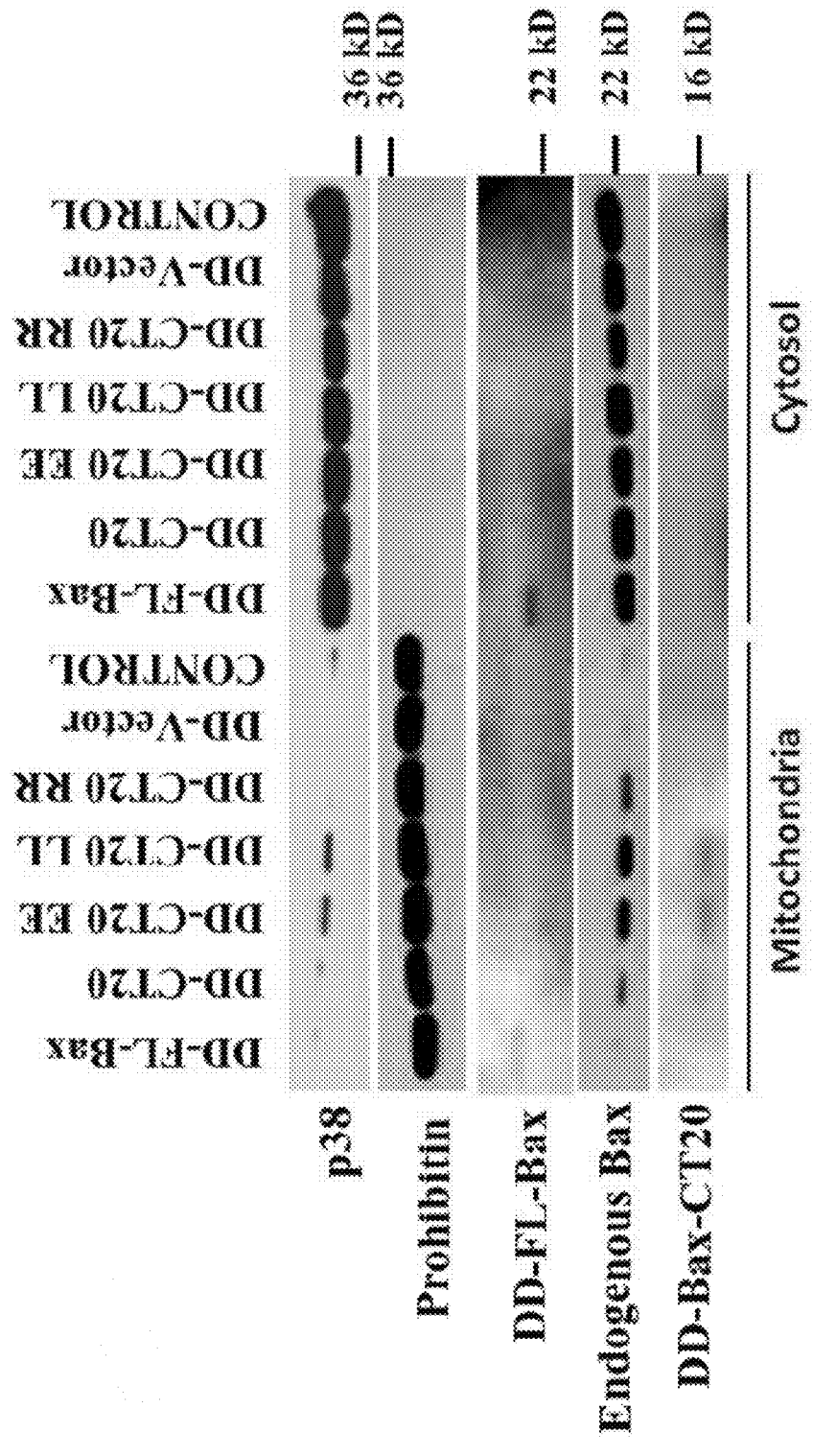
FIG. 2A shows that most of the DD-tagged Bax full length was found in cytosolic extracts.

Gene expression was induced for four hours after previous transfection of cells with DD-FL Bax or DD-CT20 peptide constructs. Constitutive GFP expression on the bi-cistronic plasmid was controlled by an IRES element and used to detect transfected cells. The mitochondrial translocation of DD-tagged Bax full-length (FL-Bax) and DD-tagged CT20 peptides, wild-type and EE, LL and RR mutants, was examined in Bax$^{+/+}$ HCT-116 cells by immunoblot. As shown in FIG. 2A, most of the DD-tagged FL Bax was found in cytosolic extracts. A fraction of DD-FL-Bax was also found in mitochondria extracts. The small 15-16 kD band of DD-CT20 KK peptides or DD-CT20 mutant peptides (EE, LL, and RR (fainter band)) was detected in mitochondrial extracts, indicating that the DD-CT20 peptides were targeting mitochondria.

Expression of DD-CT20 Bax also caused the mitochondrial translocation of a small amount endogenous Bax (FIG. 2A). Data are representative of two independent assays. In FIG. 2A, endogenous Bax was probed with anti-Bax antibody. p38 MAPK and prohibitin indicated cytosolic and mitochondrial content, respectively. DD-fusions were detected with an anti-DD antibody. Controls were cells transfected with empty vector or untransfected. Images from full-length blots were cropped for concise presentation.

Figure 7A:
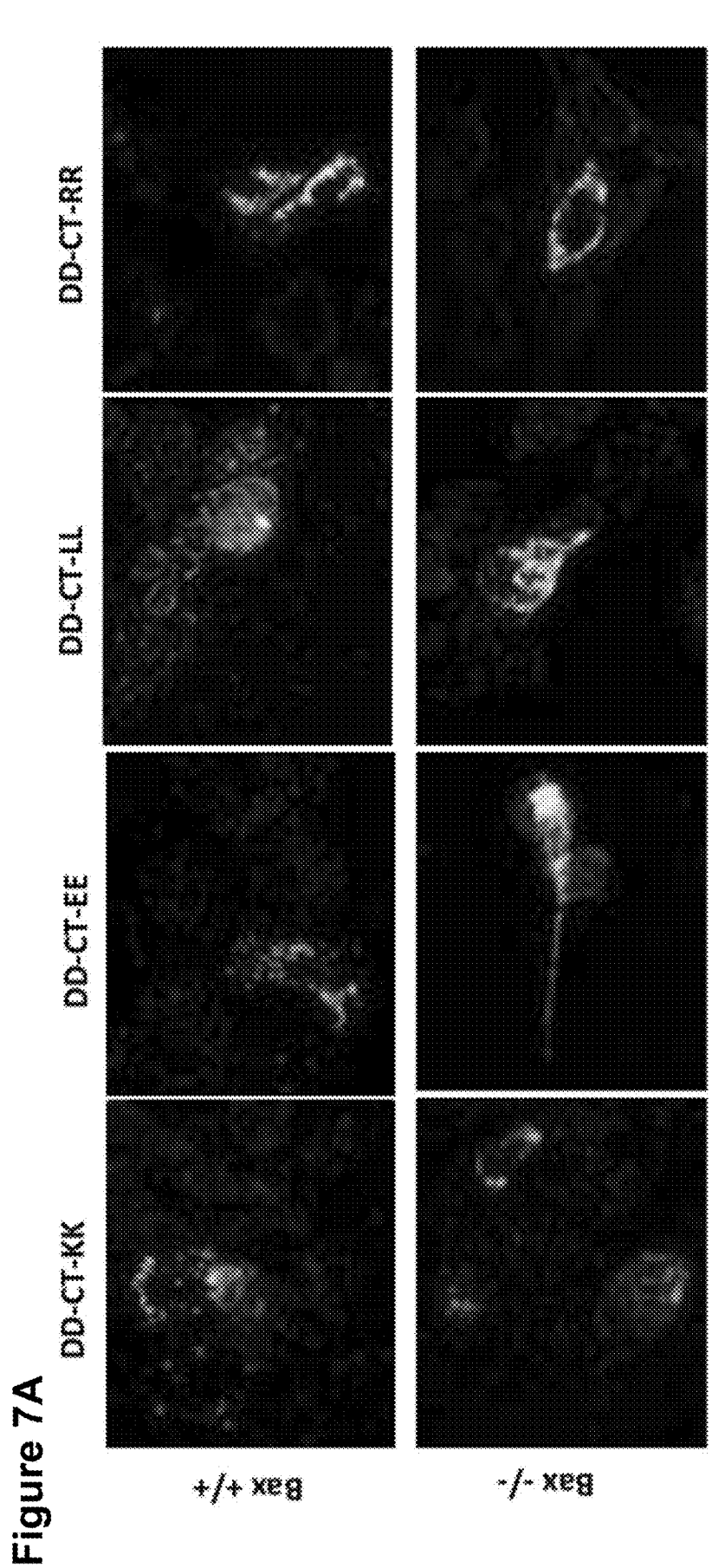
FIG. 7A illustrates that the DD-CT20p peptide is co-localized with mitochondria.
Figure 7B:
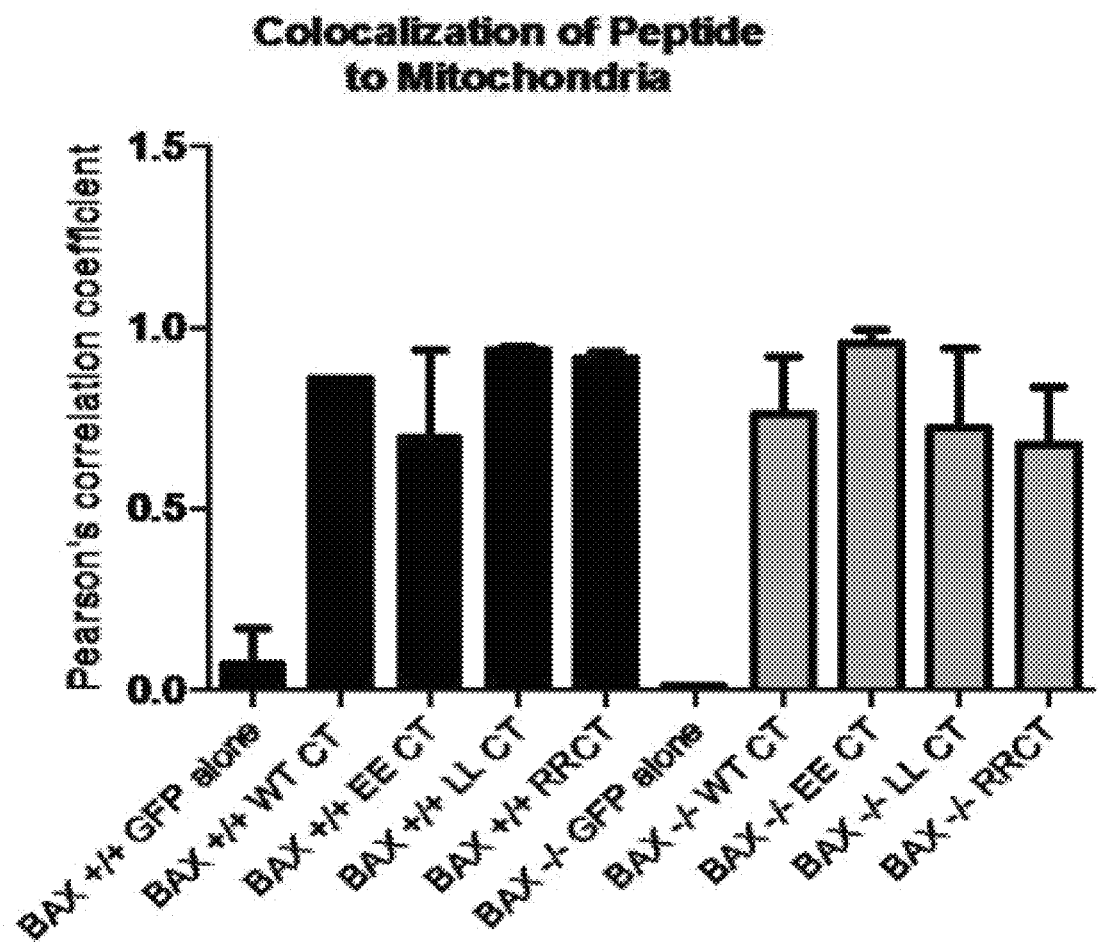
FIG. 7B shows these observations quantified and on a bar graph.

These results were confirmed by immunofluorescence (FIG. 7). In FIG. 7A, cells were fixed and double-stained with primary antibodies for HSP60 and DD. The fixed cells were then incubated with secondary anti-rabbit-Cy3 and anti-mouse-Texas red. The overlay appears as white. In FIG. 7B, the bar graphs indicate the quantitative assay of co-localization of DD-tagged peptides to mitochondria. The measurements are represented by three samples.

Figure 8B:
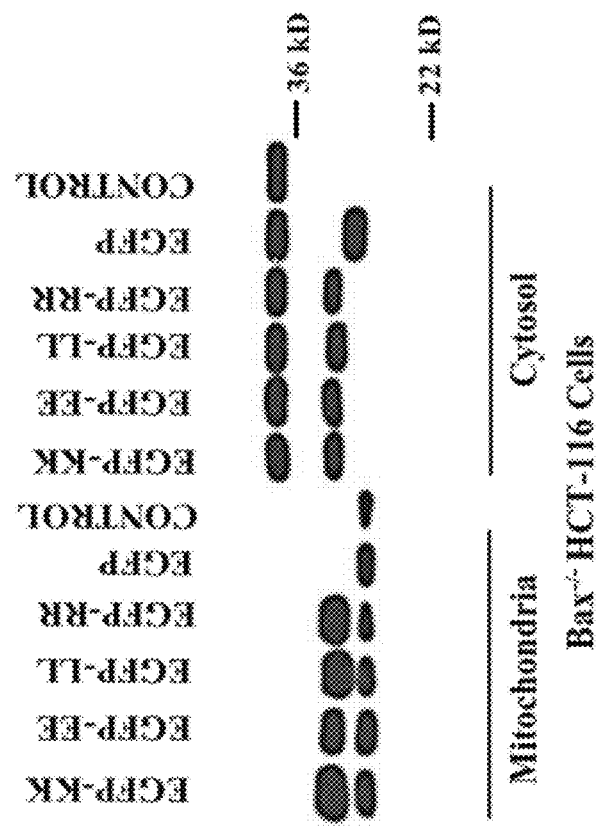
FIGS. 8A and 8B are immunoblots that show the mitochondrial translocation of EGFP-tagged with Bax CT (EGFP-KK) and K189/L190 mutants in $Bax^{+/+}$ HCT-116 cells (FIG. 8A) and $Bax^{-/-}$ HCT-116 cells (FIG. 8B).
Figure 8A:
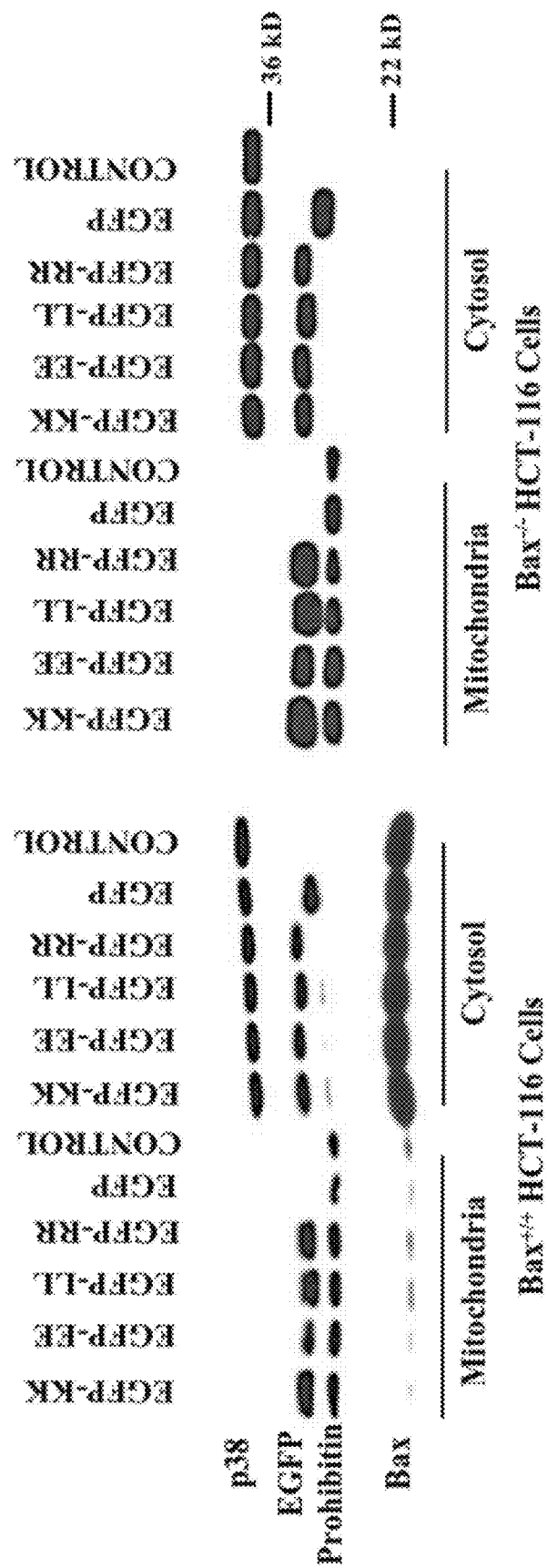

Experiments attaching the CT20 peptides to EGFP confirmed the findings that fusion of the CT20p peptide could confer membrane binding properties (FIGS. 8A and 8B). In FIGS. 8A and 8B, the mitochondrial translocation of EGFP-tagged with Bax CT (EGFP-KK) and K189/K190 mutants was examined in Bax$^{+/+}$ HCT-116 cells (A) and Bax$^{-/-}$ HCT-116 cells (B) by immunoblot. p38 MAPK and Prohibitin were assessed for cytosolic and mitochondrial content, respectively. Control sample are untransfected cells. Data are representative of five independent assays. Images from full-length blots were cropped for concise presentation.

In FIGS. 8C and 8D, Bax$^{+/+}$ HCT-116 cells and Bax$^{-/-}$ HCT-116 cells, respectively, were transfected with the EGFP-KK or K189/K190 mutants. Time-lapse movies were acquired with a 63× Oil objective. For each sample, three different fields of view were acquired. Images shown are snapshots taken at specified time points.

Figure 2C:
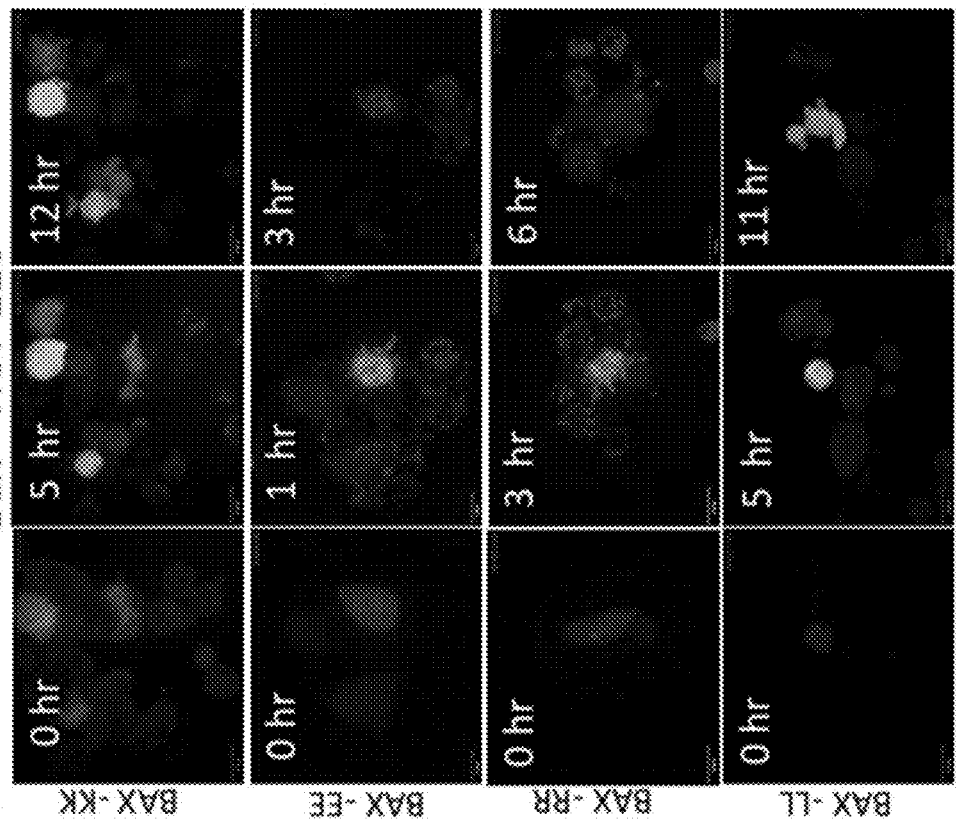
FIGS. 2B and 2C show that DD-tagged CT20 p peptide translocated to mitochondria and caused cell death.
Figure 2B:
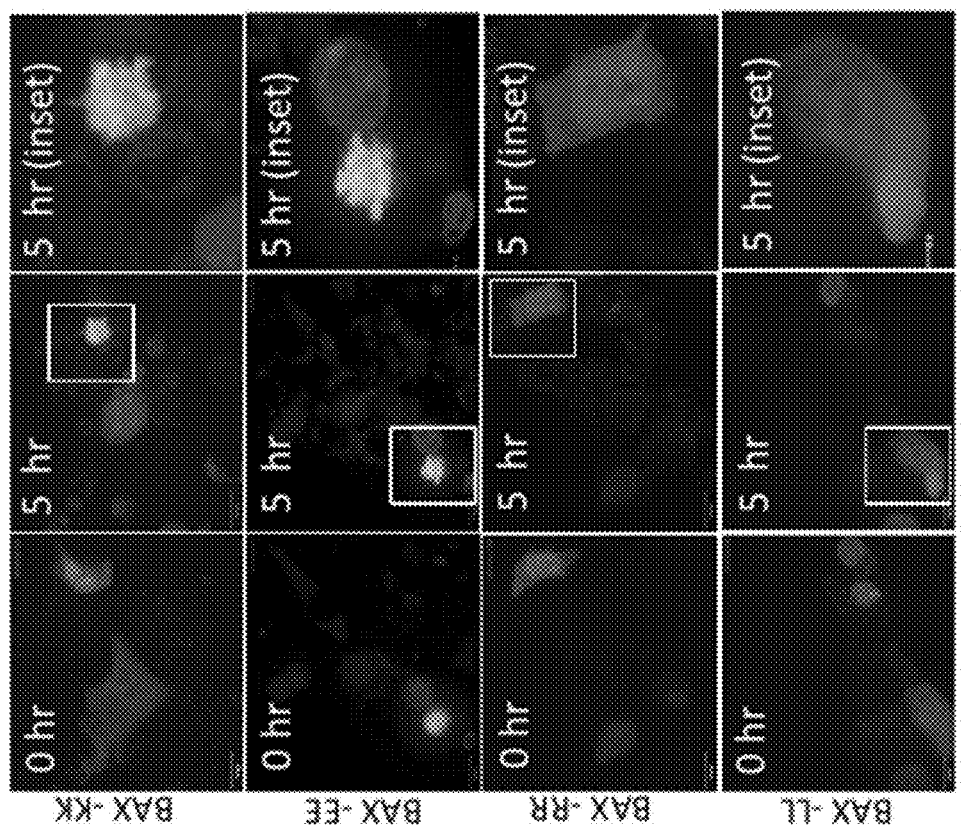
Figure 12:
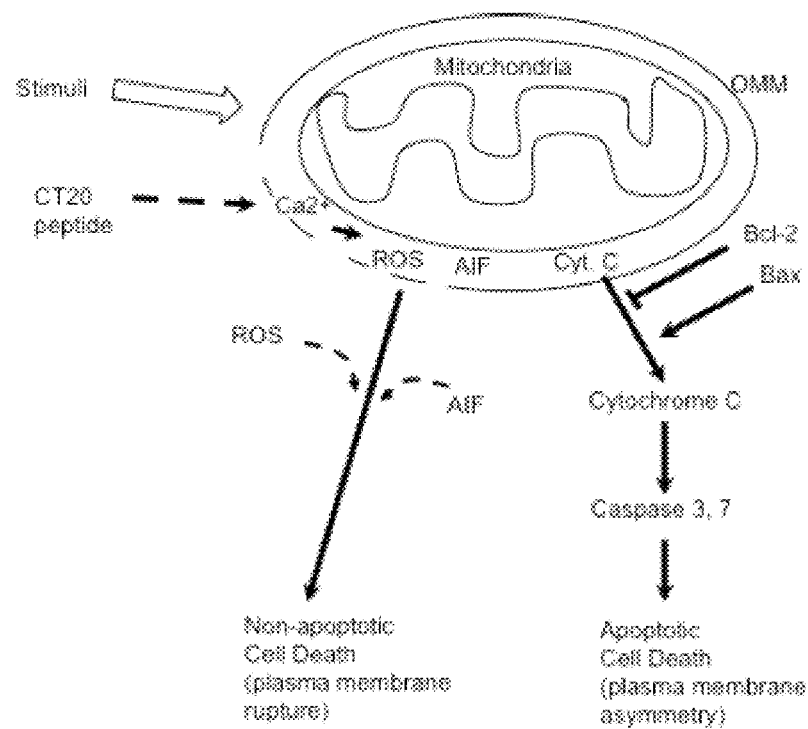
FIG. 12 shows a hypothetical cell death pathway for CT20p peptide using a basic model of apoptotic and non-apoptotic cell death.

The toxicity of DD-CT20 KK peptide was shown when expression was induced in HCT-116 cells (FIG. 2B for Bax$^{+/+}$ cells and FIG. 2C for Bax$^{-/-}$ cells). For each sample, three different fields of view were acquired. Images are representative "snapshots" of four independent experiments. Within five hours of gene induction, the DD-CT20 KK peptide caused membrane perturbations and the death of Bax-containing cells. Similar results were observed with the other forms of DD-CT20 (EE, LL and RR) peptides, although the death kinetics varied depending on the mutation (LL and RR mutants took longer to cause death) (FIG. 2B, 5 hours; insets in FIG. 2B were increased 3-fold). Moreover, Bax deficiency did not impair the lethality of the CT20 Bax peptide. This was observed by expressing DD-CT20 KK in Bax$^{-/-}$ HCT 116 cells, which caused cell death detectable by 3-5 hours (FIG. 2C, 12 hours). DD-CT20 EE caused membrane disturbances by 1 hour of induction and death by 3 hours. This was followed by DD-CT20 RR, with loss of membrane integrity observed within 3 hours, and DD-CT20 LL causing membrane fluctuations by 5 hours and death by 11 or 12 hours (FIG. 2C). While mutation of the C-terminal lysines did not block mitochondrial translocation (FIG. 2A) or prevent cell death, it did alter the timeframe in which death occurred. These finding were confirmed with multiple similar experiments, which accounted for differences in transfection efficiency and expression of individual constructs. The data indicate that the C-terminal lysines were needed to "fine tune" the interaction of the CT20 peptide with mitochondrial membranes, altering its capacity to induce cell death. (See FIG. 1C showing that CT20 peptides (WT and mutants) associated with lipid membranes, which affected membrane rigidity, but that only the CT20 WT (containing K189/K190) enabled the maximal release of calcein from loaded vesicles).

4. Delivery of the CT20 Peptide Using Polymeric Nanoparticles Kills Cancer Cells To determine whether the CT20p peptide could directly kill cancer cells, the CT20 wild type peptide was encapsulated in polymeric nanoparticles. As the CT20p peptide is amphipathic, it can be encapsulated within the hydrophobic pockets of aliphatic polymeric nanoparticles. FIG. 3A shows a schematic representation of the three dimensional structure of aliphatic hyperbranched nanoparticles, in which DiI (fluorescent dye) and commercially synthesized CT20 Bax peptides were encapsulated into positively charged, aminated (AM) or negatively charged, carboxylated (COOH) nanoparticles (Santra et al., 2010). To verify that the nanoparticles would not release the CT20 peptide at neutral pH, calcein loaded liposomes were prepared. While the CT20p peptide alone (350 pM) did induce the release of calcein (as shown in FIG. 1C), nanoparticles loaded with CT20 peptide (350 pM) did not induce the release of calcein from liposomes, indicating that the nanoparticles were intact at pH 7 (FIG. 9).

Figure 9A:
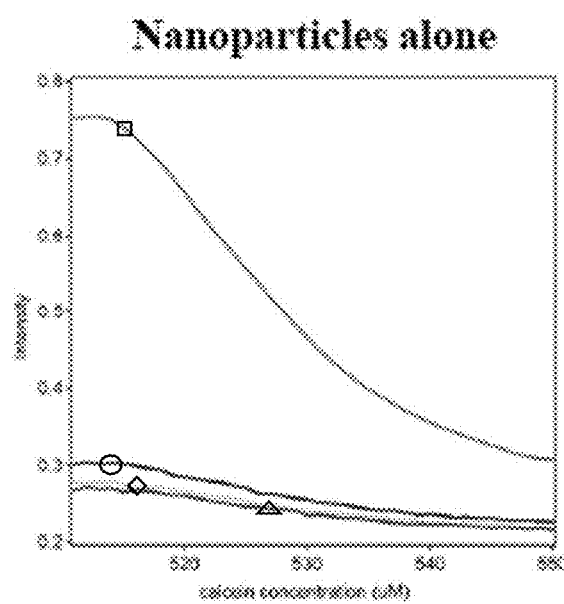
FIGS. 9A and 9B show the effect of nanoparticles alone (FIG. 9A) or with BAX peptide (FIG. 9B) on lipid vesicles.
Figure 9B:
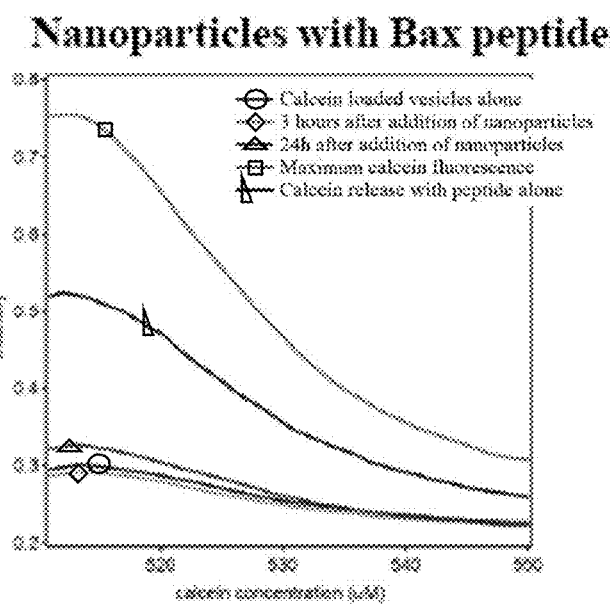

In FIG. 9, a calcein release assay was performed with calcein loaded lipid vesicles prepared with the composition of the mitochondrial membrane. Calcein release was measured as fluorescence. Controls were calcein release achieved with CT20p peptide alone and maximum calcein release obtained upon addition of Triton x100. A representative experiment of two independent experiments is shown. This confirmed that cargo is released from nanoparticles only by intracellular esterases or acidic pH (Santra et al., 2010).

Figure 3B:
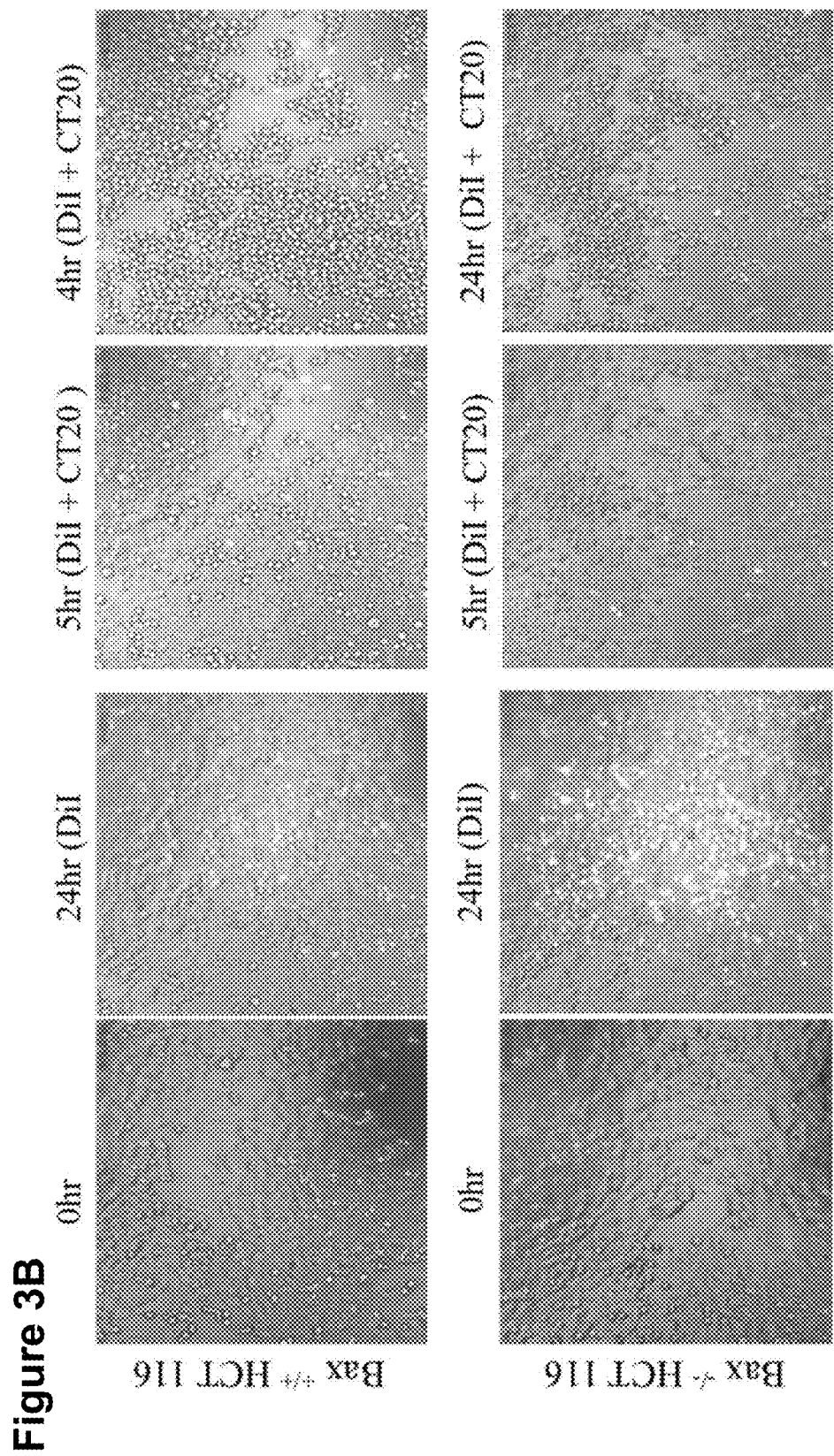
FIG. 3B shows a schematic representation of cells taking up nanoparticles.

The uptake of DiI-loaded nanoparticles and effect upon the viability of HCT-116 cells was evaluated. HCT-116 cells were treated with nanoparticles loaded with DiI or DiI+ CT20 peptide (0.07 nM) for 24 hours. FIG. 3B shows that HCT-116 cells took up nanoparticles, more so for the Bax-deficient cells that were highly glycolytic (Boohaker et al., 2011). While treatment of HCT-116 cells with nanoparticles (unloaded) did not cause significant cell death (FIG. 3B), treatment of HCT-116 cells with CT20 peptide-loaded nanoparticles at a concentration of 700 pM (or 0.07 nM), caused rapid cell death (FIG. 3B). For each sample, three different fields of view were acquired. Images are representative "snapshots" of two independent experiments.

To demonstrate that nanoparticles alone (i.e., without the CT20 peptide) did not cause death, a DNA-binding dye (Sytox) was utilized to detect membrane rupture of dead cells. FIG. 3C shows that minimal (Bax$^{+/+}$ HCT-116) to no (Bax$^{-/-}$ HCT-116) cell death was detected upon addition of DiI-loaded nanoparticles (5 µg, 10 µg or 15 µg) as compared to the positive control (dead cells). To minimize off-target effects, all subsequent experiments were performed at the lowest dose of the CT20 peptide (350 pM)-nanoparticles (2.5 µg).

Figure 4A:
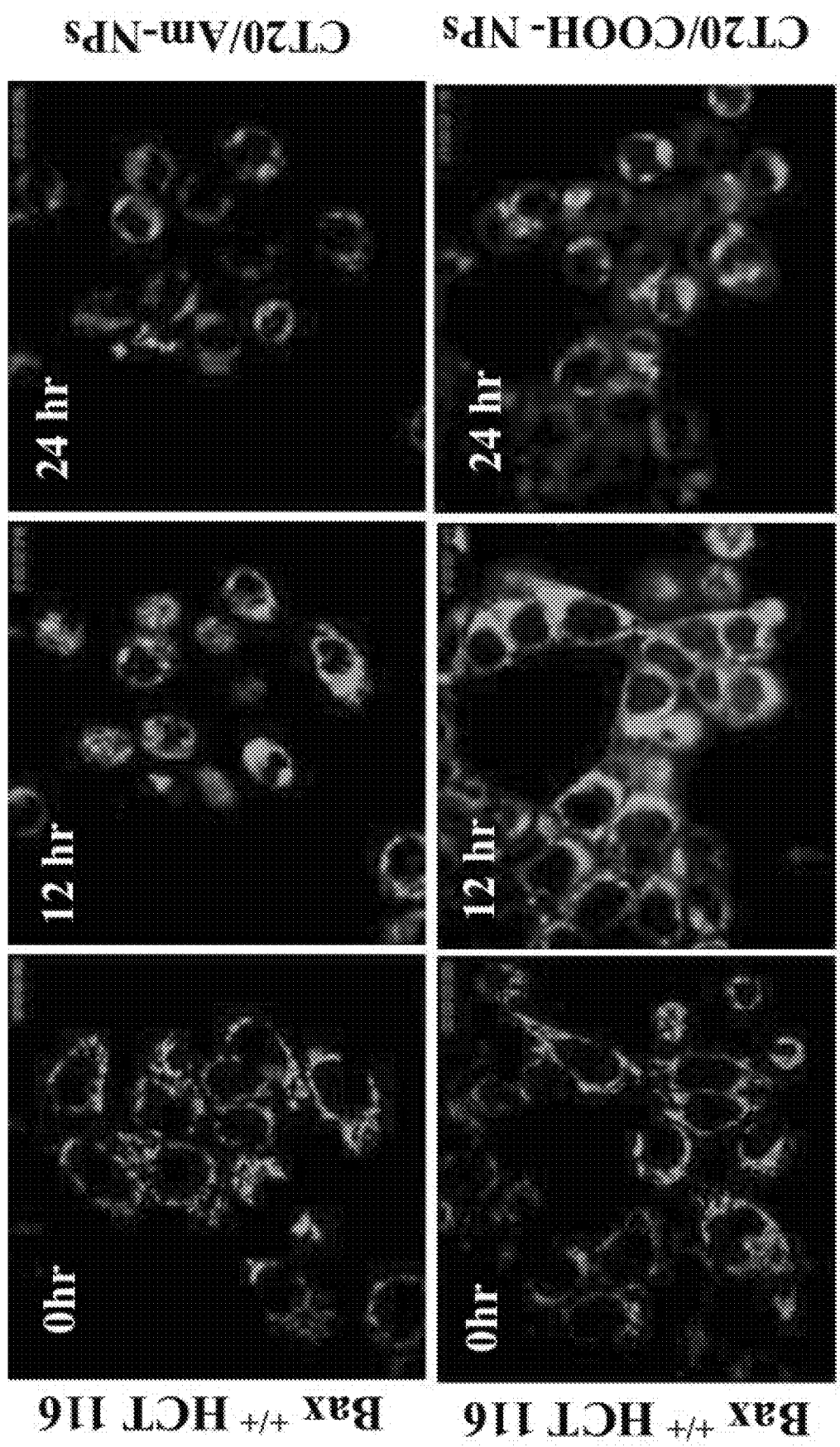
FIG. 4A shows changes in cell morphology, including disruption of mitochondria, cell shrinkage and membrane perturbations that are indicative of cell death of $Bax^{+/+}$ HCT-116 cells.
Figure 4B:
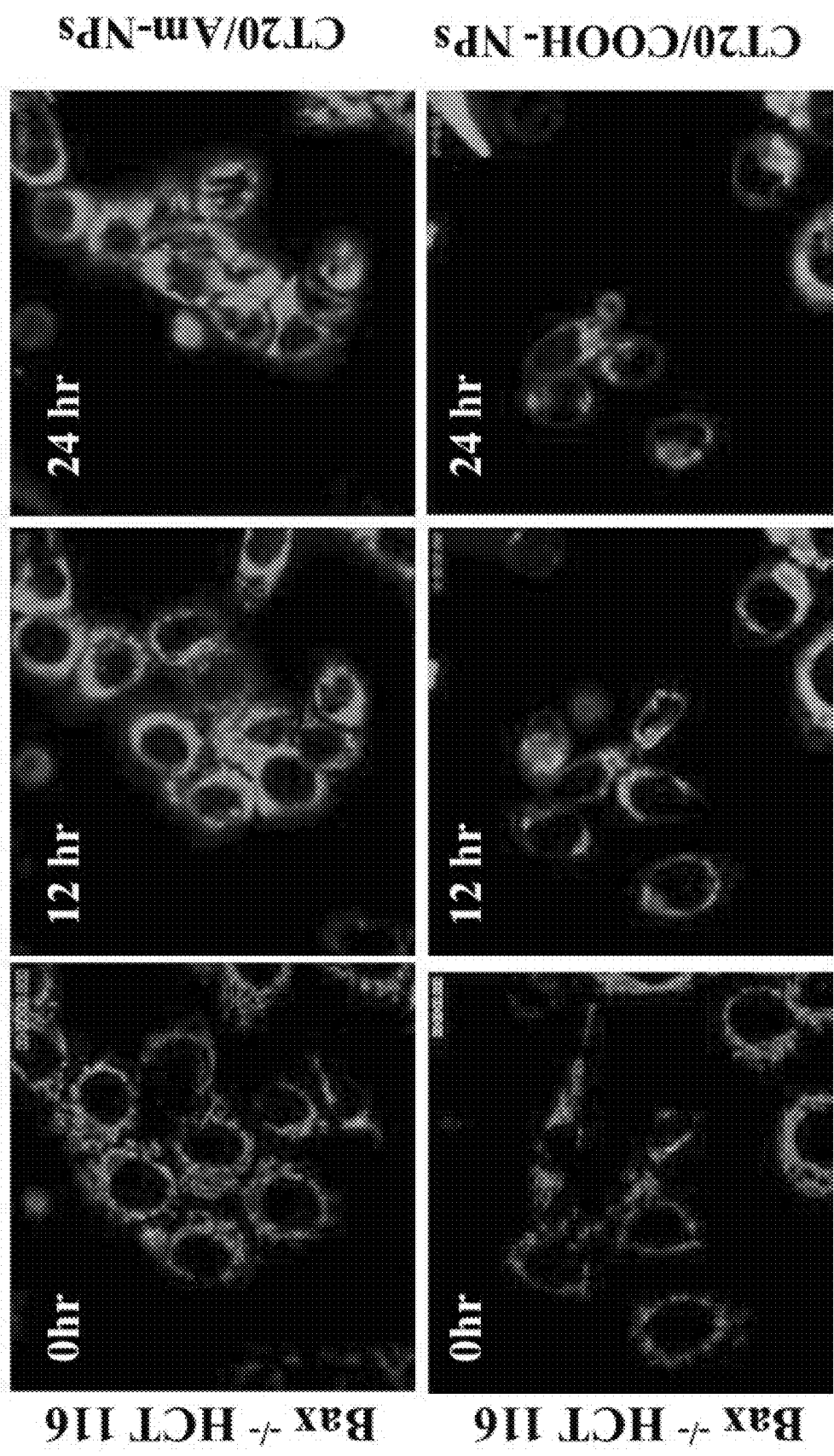
FIG. 4B shows changes in cell morphology, including disruption of mitochondria, cell shrinkage and membrane perturbations that are indicative of cell death of $Bax^{-/-}$ HCT-116 cells.

To visualize the effect of CT20 Bax peptide-nanoparticles upon mitochondria, Bax-containing or Bax-deficient HCT-116 cells were stained with Mitotracker and imaged live cells. Bax$^{+/+}$ (FIG. 4A) and Bax$^{-/-}$ (FIG. 4B) HCT-116 cells were treated with AM- or COOH-nanoparticles loaded with CT20 peptide (350 pM) for 24 hours. To visualize mitochondria, cells were treated with MitoTracker Red 580 and time-lapse movies were acquired using a 63× Oil objective. FIGS. 4A and 4B show "snapshots" at 0, 12, and 24 hour time points. These snapshots revealed changes in cell morphology, which changes included disruption of mitochondria (reduced or faint Mitotracker staining), as well as cell shrinkage and membrane perturbations, which were indicative of cell death.

Figure 4C:
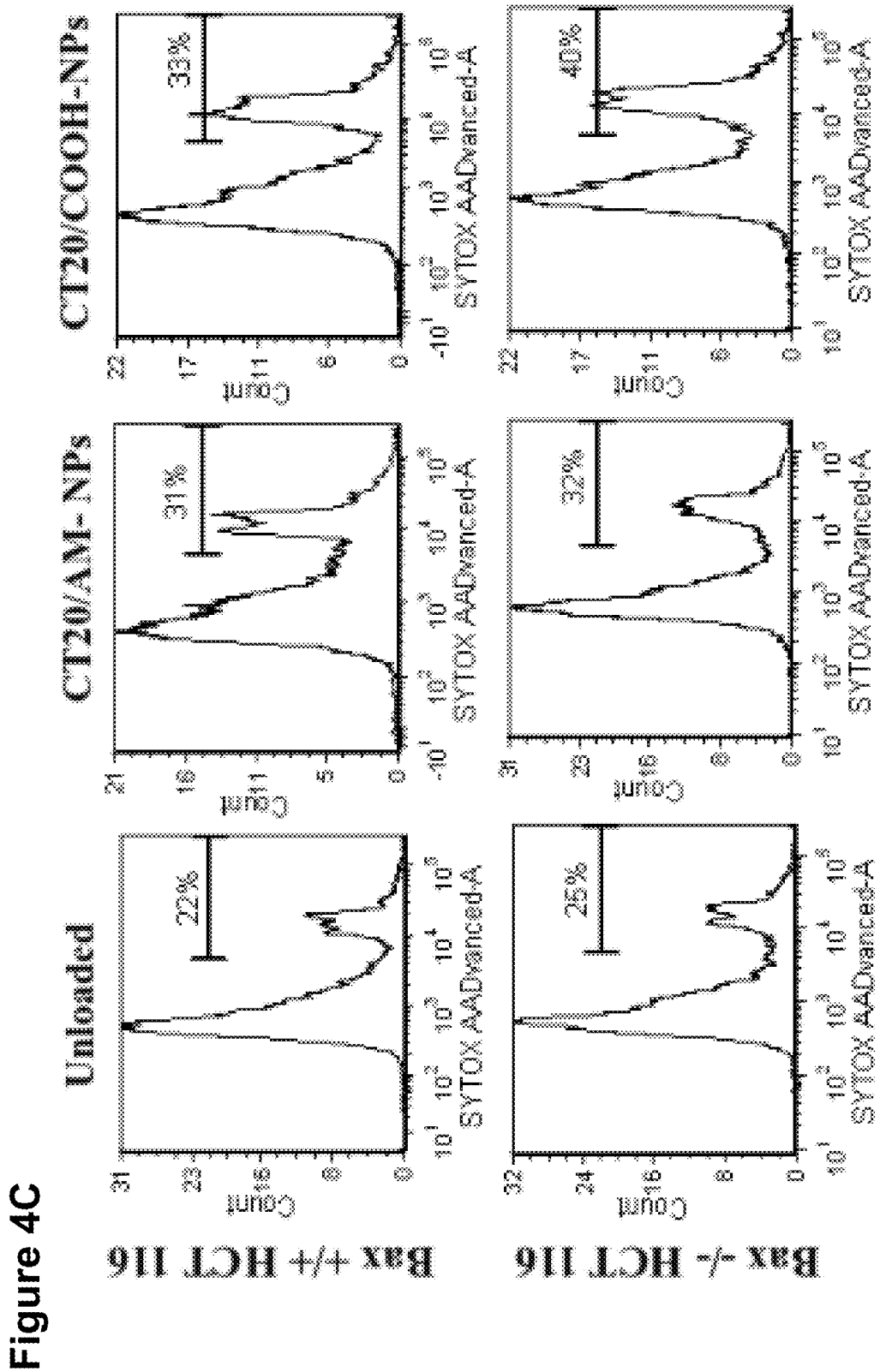
FIG. 4C shows that cell death was measured and the loss of membrane integrity was detected within three hours of treatment with CT20 Bax peptide-nanoparticles.

Similarly, HCT-116 cells were treated with nanoparticles loaded with CT20 peptide (350 pM). Cell death was measured and the loss of membrane integrity was detected within three hours of treatment with CT20 Bax peptide-nanoparticles (FIG. 4C). Both AM-nanoparticles and COOH-nanoparticles containing CT20p peptide were efficacious in initiating cell death (FIG. 4C), although the COOH-nanoparticle formulation appeared more effective. These results coupled with those in FIG. 2 indicated that the death-inducing activity of the CT20p peptide was independent of endogenous Bax. With respect to FIGS. 4A-C, three different fields of view were acquired for each sample. Images are representative "snapshots" of three independent experiments.

Figure 5A:
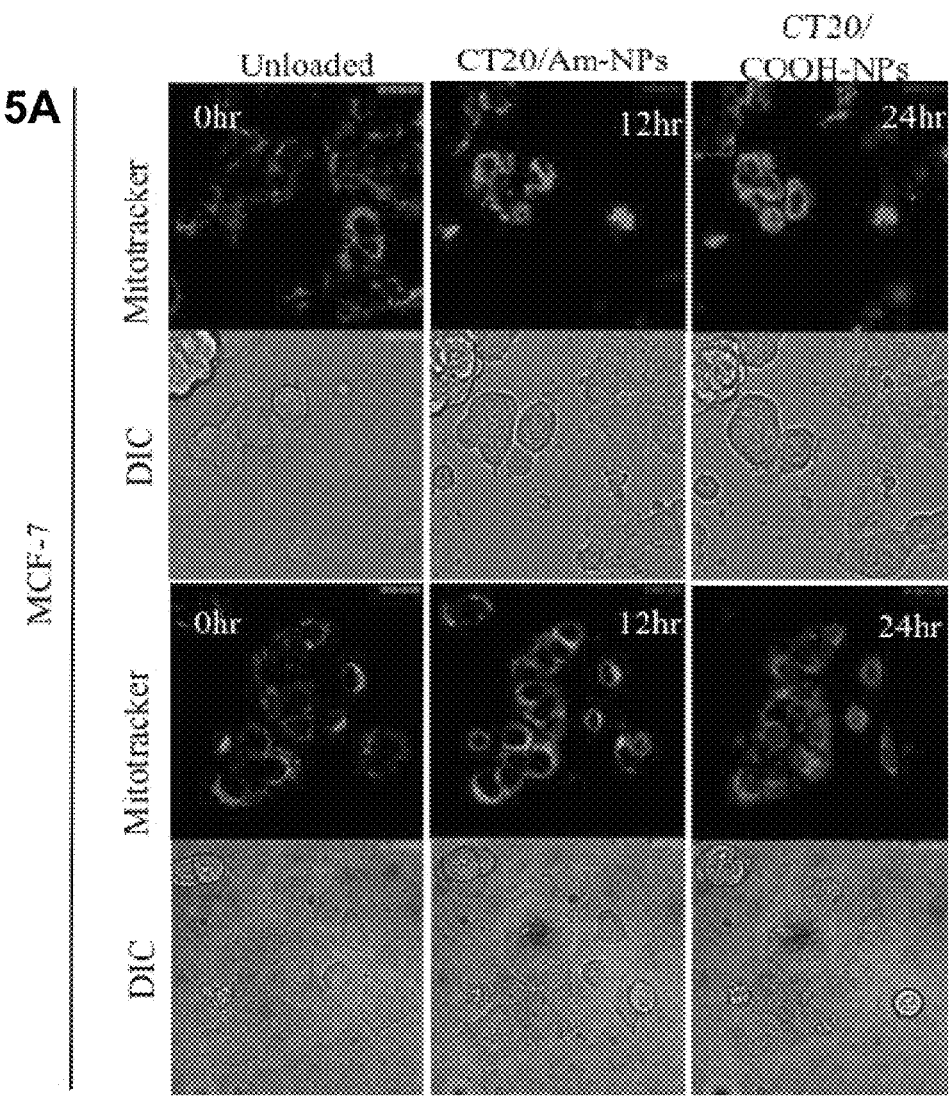
FIGS. 5A and 5C show morphological changes in MCF-7 (FIG. 5A) and MDS-MB-231 (FIG. 5C) cells following treatment with CT20p peptide nanoparticles.
Figure 5B:
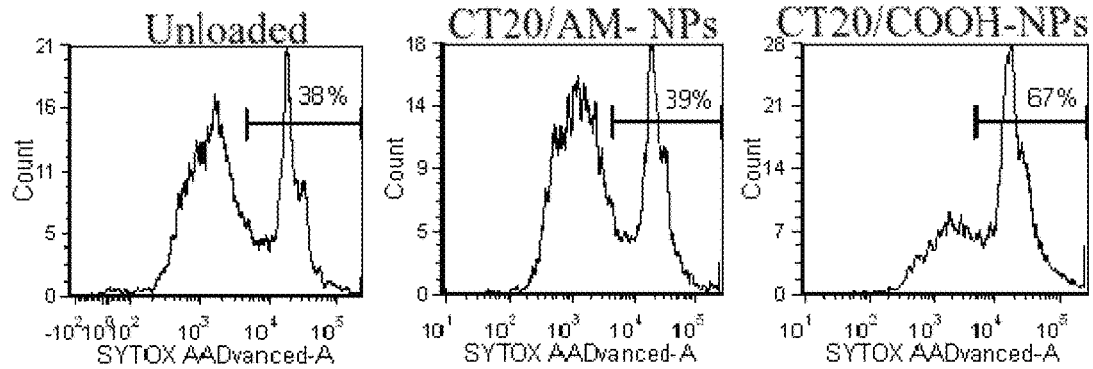
FIGS. 5B and 5D show that the loss of membrane integrity was detected by 3 hours of treatment in MCF-7 (FIG. 5B) and MDS-MB-231 (FIG. 5D).
Figure 5C:
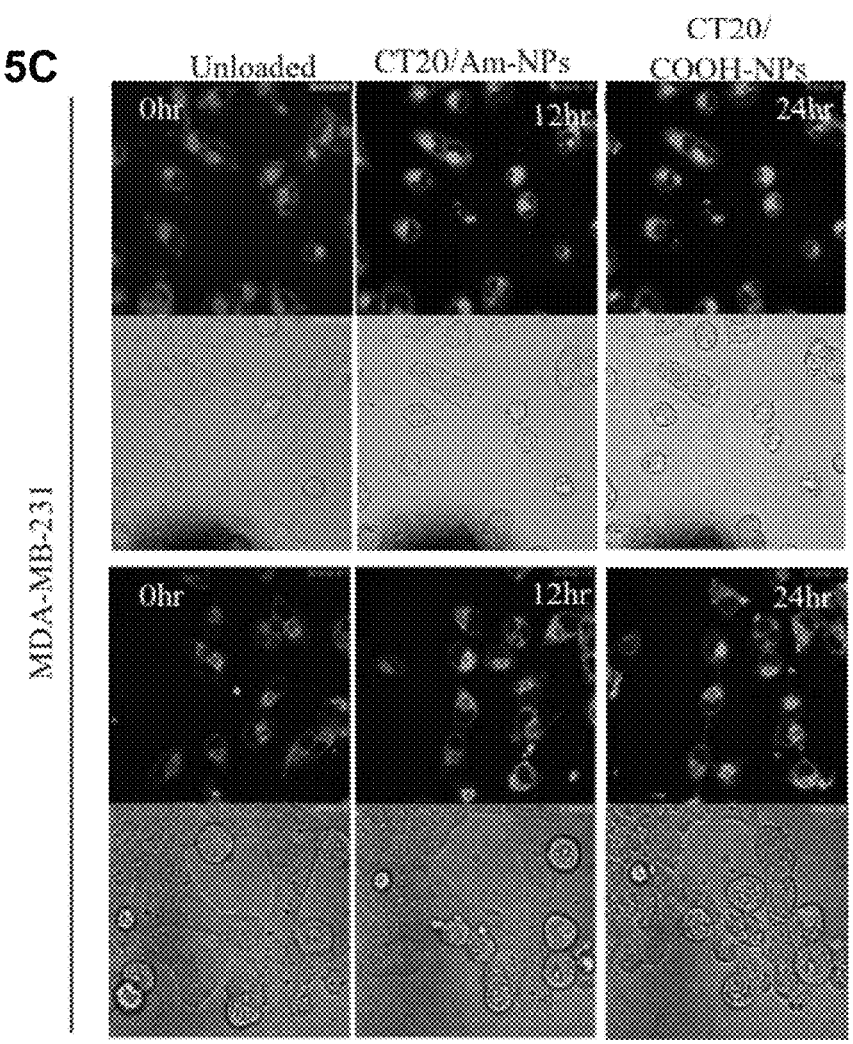
Figure 5D:
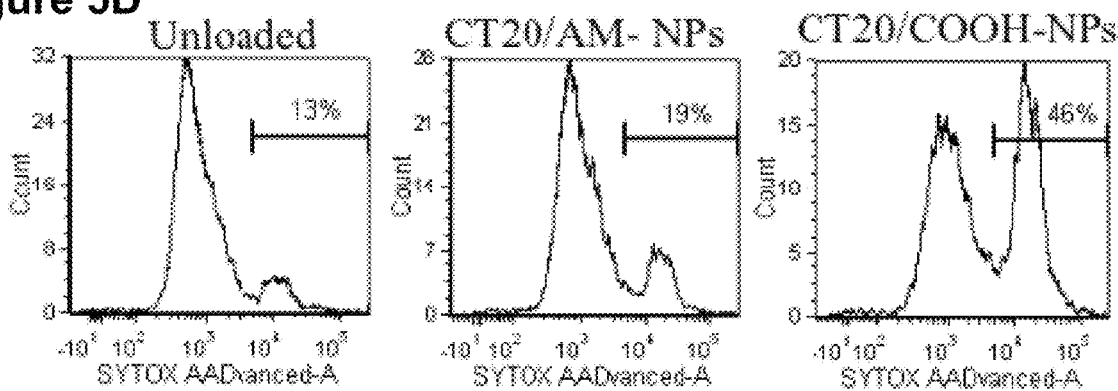

Whether the CT20 peptide was able to kill the breast cancer cells, MCF-7 and MDA-MB-231, was examined. As shown in FIG. 5A, morphological changes such as cell shrinkage and membrane perturbations in MCF-7 cells following treatment for 24 hours with AM- or COOH-nanoparticles containing the CT20p peptide(350 pM) were observed. For each sample, three different fields of view were acquired. Images are representative "snapshots" of three independent experiments Most MCF-7 cells died within 24 hours, while loss of membrane integrity was detected by 3 hours of treatment (FIG. 5B). In FIG. 5C, the live cell imaging experiment revealed vacuolization, membrane fluctuations, and cell shrinkage of MDA-MB-231 cells following treatment with CT20 peptide-nanoparticles. Within three hours, increased membrane rupture was detected in MDA-MB-231 cells treated with COOH-nanoparticles loaded with CT20 peptide (FIG. 5D). These results demonstrated that the CT20 peptide, once introduced into cells, rapidly triggered cell death. While the CT20 peptide encapsulated in nanoparticles caused the death of four cancer cell lines (colon and breast), the CT20 Bax peptide/nanoparticle formulation was less effective inducing death in two lung cancer cell lines. This data indicated that that differences in the uptake and efficacy of the CT20 peptide/nanoparticles could exist that are related to the physiology of the cancer cell.

5. The Death-Inducing Activity of the CT20p Peptide is Independent of Caspases and Resistant to BCL-2.

Figure 6A:
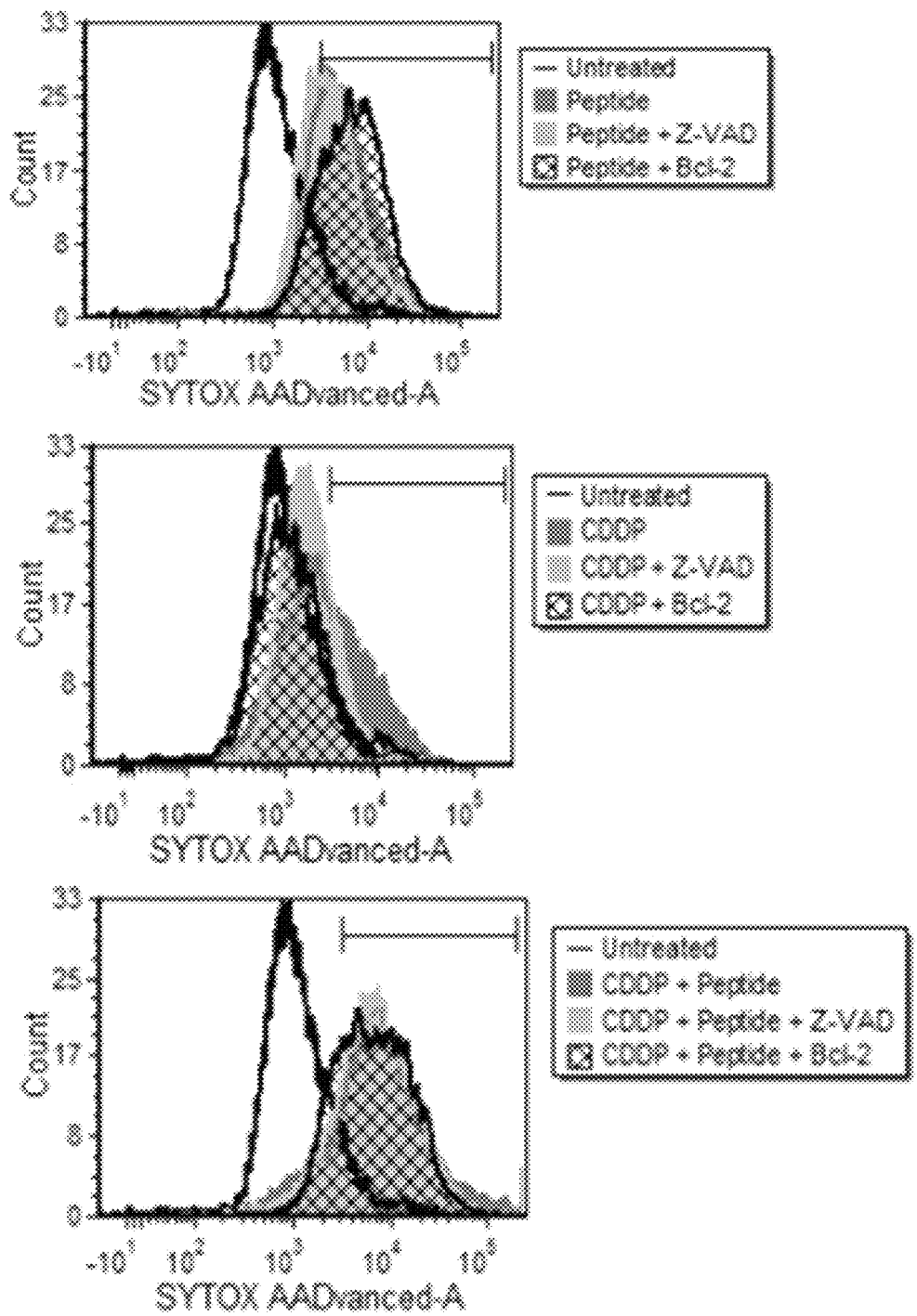
FIGS. 6A and 6B show data for membrane and cellular effects of CT20p peptide, including that tumor cell death mediated by the CT20p peptide is independent of effector caspases and is resistant to Bcl-2 overexpression.

To investigate the mechanism by which the CT20p peptide was inducing cell death, MDA-MB-231 cells were treated with CT20 Bax peptide/nanoparticles (350 pM). A caspase inhibitor (e.g., ZVAD-Fmk and/or CDDP) was added or Bcl-2 was overexpressed. As shown in FIG. 6A, the CT20 peptide caused significant loss of membrane integrity, which was largely unaffected by caspase inhibition with Z-VAD-FMK. In contrast, treatment of MDA-MB-231 cells with cisplatin (CDDP) induced cell death that was inhibited by ZVAD-FMK. These results indicated that the death pathway induced by the CT20p peptide was different than CDDP and was independent of the effector caspases inhibited by ZVAD-FMK. When Bcl-2 was overexpressed, the overexpression did not impair the death activity of the CT20 Bax peptide, but rather slightly enhanced it. Bcl-2 overexpression impaired death induced by CDDP (FIG. 6A). Administration of CDDP followed by treatment with the CT20 peptide was the most effective in inducing cell death, which was not inhibited by ZVAD-FMK or Bcl-2 (FIG. 6A). The expression of Bcl-2 by transfected cells was confirmed by immunoblotting lysates prepared from cells (FIG. 10).

In FIG. 10, cells were transiently transfected with Bcl-2, treated with nanoparticles/CT20. Lysates were immunoblotted for Bcl-2. Controls are untransfected cells (UT) and untreated cells (control). * denotes a non-specific band. A representative blot of two performed is shown.

Figure 6B:
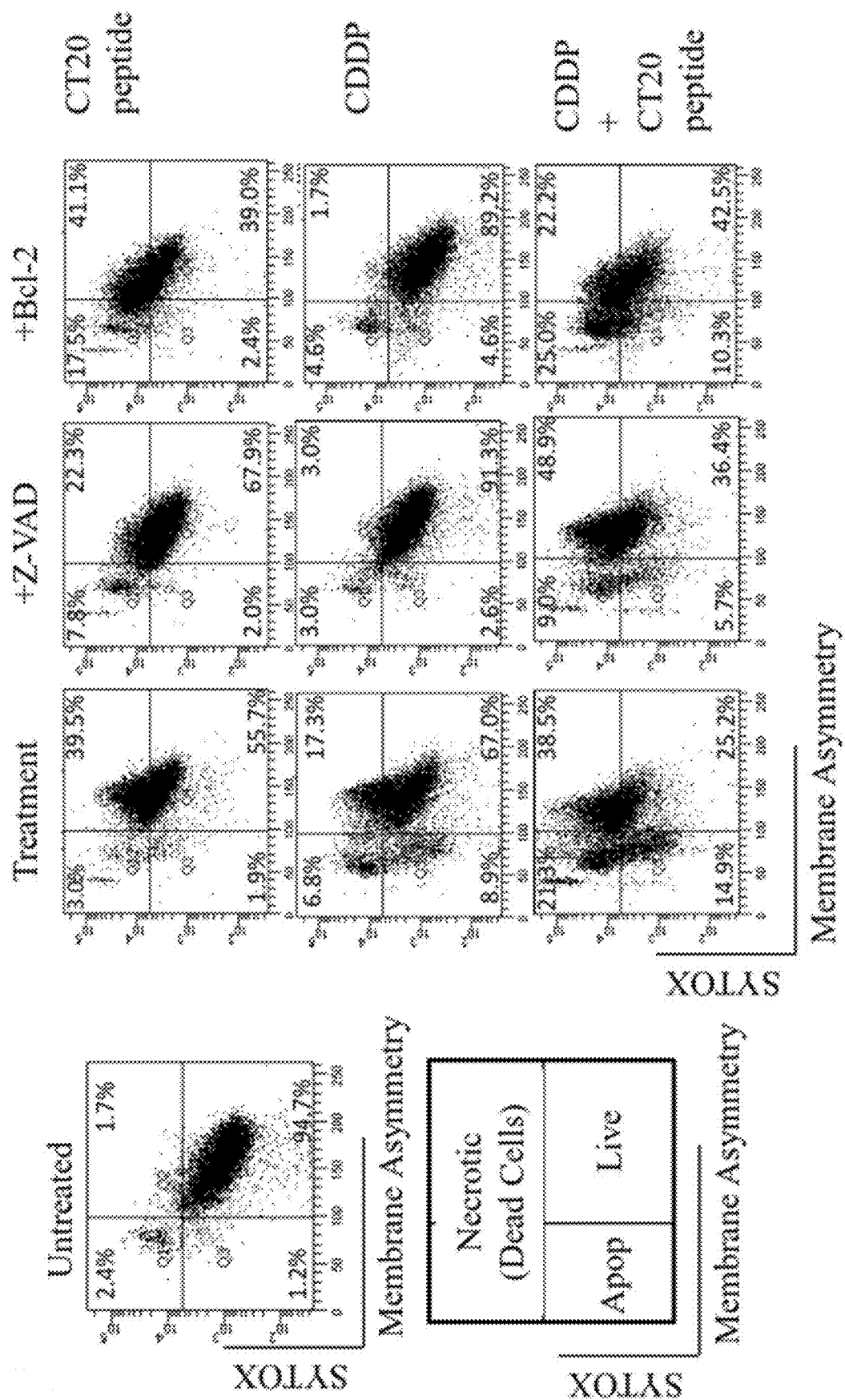

While Sytox is good indicator of cell death, it does not distinguish between apoptotic and necrotic cell death. Therefore, to determine whether the CT20p peptide induced apoptotic cell death, the amount of membrane asymmetry caused by flipping of phospholipids phospholipids in the plasma membrane using a violet ratiometric probe was determined. In FIG. 6B, dot blots show the comparison of loss of membrane integrity to changes in membrane symmetry in MDA-MB-231 cells treated with CT20p peptide and/or CDDP. Treatment with the CT20p peptide encapsulated in nanoparticles enabled penetration of the DNA-binding dye (as shown in FIG. 6A), but did not promote changes in membrane symmetry. This was minimally affected by caspase inhibition or Bcl-2 expression. In contrast, contrast, CDDP induced significant alterations in the membrane symmetry detectable by the violet ratiometric probe, which alterations were inhibited by ZVAD-FMK or Bcl-2 (FIG. 6B; data shown is representative of more than three independent experiments). The combination treatment of CDDP and CT20p peptide was the most efficacious and was minimally affected by caspase inhibition or Bcl-2 expression (FIG. 6B). These findings indicate that the CT20 peptide engages in a death mechanism distinct from that of CDDP, and and that this distinct mechanism is independent of ZVD-FMK inhibited-caspases and is resistant to Bcl-2.

Figure 6C:
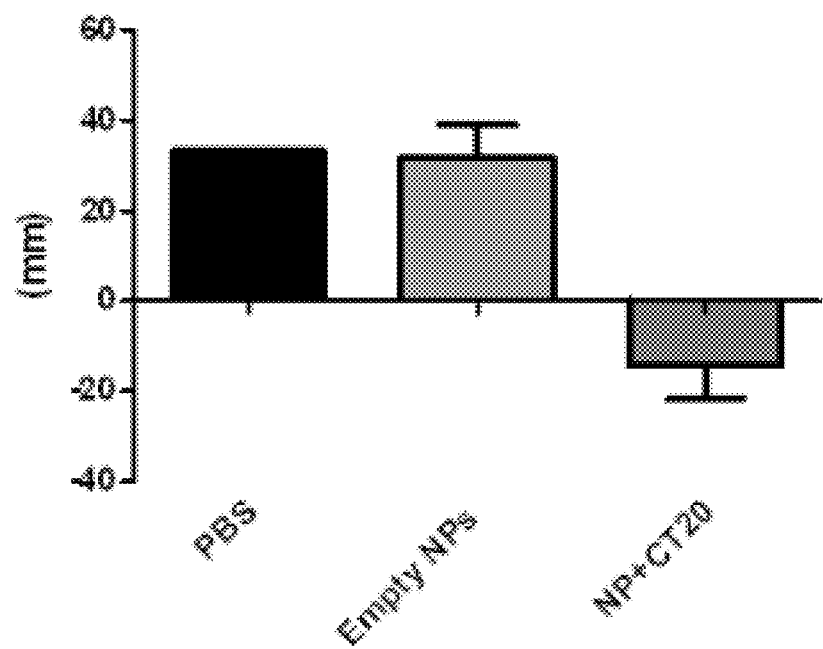
FIGS. 6C-D show that CT20p peptide can cause tumor regression in a mouse model of breast cancer.

To demonstrate that the CT20 peptide could kill cancer cells in vivo, a small scale murine tumor experiment was performed. MDA-MB-231 cells were implanted in the flanks of nude mice. Initial growth of tumors was detected after 2 weeks. At this time tumors were measured, and over a 4-5 day period, the mice were treated with intratumoral injections of PBS, unloaded or empty nanoparticles (NP), or CT20 peptide/nanoparticles. The CT20 peptide prevented tumor growth as compared to empty nanoparticles or a PBS-treated tumor. (FIG. 6C; results displayed in the graph show the change in tumor volume during the four days of treatment and are a representative of three independent experiments). These results demonstrated that the CT20 peptide was effective not only in tissue culture, but also in the tumor environment.

Figure 6D:
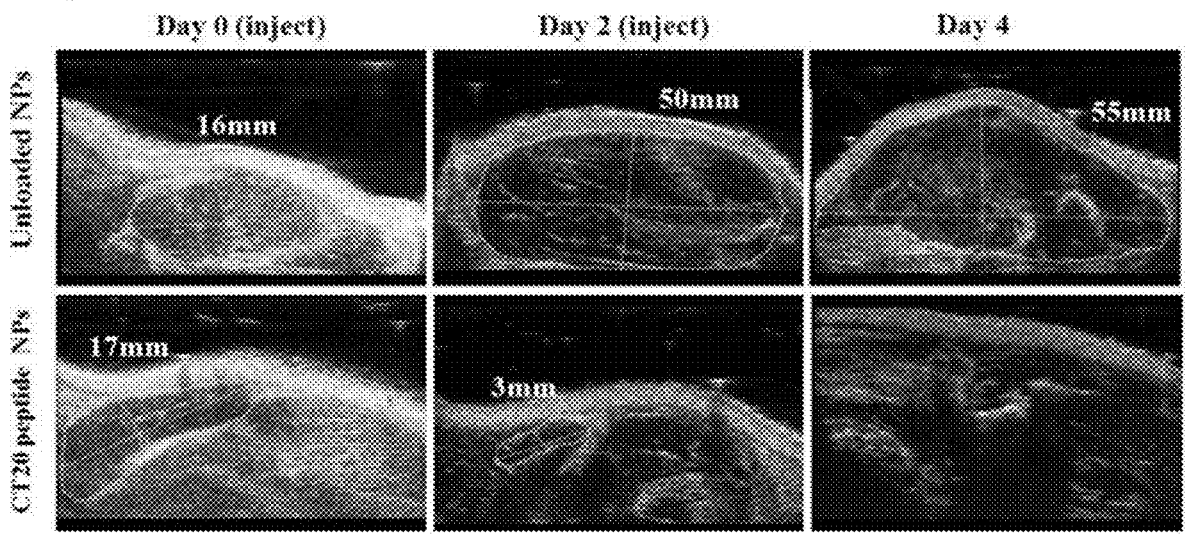

Moreover, the ultrasound data in FIG. 6D showed little to no observable damage of normal tissue surrounding the regressing tumors treated with the CT20 peptide. FIG. 6D provides representative ultrasound image of changes in tumor volume induced by treatment on days 0, 2 and 4 with the unloaded or CT20 peptide loaded nanoparticles. These findings indicate reduced uptake or effectiveness in non-cancerous cells.

Collectively, these data demonstrated that the C-terminal domain of Bax has membrane-binding capacity. The CT20p peptide permeabilized membranes and caused cell death. The CT20 peptide, unlike the full-length Bax protein, caused a lethal cascade that resulted in membrane rupture that is not characteristic of conventional apoptosis. The amphipathic features of the CT20 peptide made it amenable to encapsulation in nanoparticles and delivery to cancer cells. The CT20 peptide caused the death of colon and breast cancer cells, even in the absence of endogenous Bax or expression of Bcl-2, and led to reduced tumor volume in a murine model. The CT20 peptide caused cell death in a manner that was different from the apoptotic mechanism activated by CDDP.

Central to the lethal function of Bax is the membrane binding capacity of domains like the C-terminal alpha-9 helix. Loss of the C-terminus, or mutagenesis of K189/K190, modulated the ability of Bax to associate with mitochondria. The CT20 peptide, derived from the C-terminal a9 helix of Bax, penetrated and permeabilized lipid vesicles. The CT20 Bax peptide, when encapsulated in nanoparticles, was toxic at picomolar concentrations. The CT20 Bax peptide/nanoparticle mixture induced morphological features of cell death such loss of membrane integrity and cell shrinkage, but did not cause the changes in membrane symmetry that characterizes apoptosis. Use of the Bax CT20 peptide/nanoparticles as an anti-cancer agent was demonstrated when breast cancer cell lines succumbed to treatment as indicated by increased loss of membrane integrity that was not impaired by caspase inhibition or Bcl-2 expression. The CT20 peptide caused a form of cell death that was mechanistically different from typical anti-cancer drugs like CDDP.

The data indicate that the CT20p peptide kills cells caused the formation of pores in mitochondrial membranes. The CT20p peptide was efficient at forming pores in zwitterionic and anionic lipid membranes, leading to the release of calcein from loaded lipid vesicles. FIG. 11, for example, shows a model for a membrane pore formed by the CT20 Bax peptide. Control peptides did not permeabilize lipid membranes, causing calcein release, which indicated that the observed pore formation was specific to the CT20 Bax peptide. Second-order rate kinetics revealed that initial pore formation by the CT20p peptide was slow, which was followed by a faster rate of assembly. The data indicate that the CT20p peptide formed pores leading to membrane destabilization, ion exchange, and/or the release of sequestered molecules.

Pore-forming proteins or peptides that can spontaneously insert into lipid membranes and form stable pores have significant biological interest and clinical application. As demonstrated herein, the CT20 peptide, a shorter version of the α9 helix of Bax (amino acids 172-192), caused cell death indicated by membrane rupture. These findings indicate that the CT20 peptide may cause necrotic-like cell death, rather than conventional apoptosis, and therefore has the potential for additive effects in combinatorial therapies with agents like CDDP that induce apoptosis. The data presented herein show that a small amount of the CT20 peptide was lethal under conditions when the apoptotic machinery is intact (such as Bax-containing HCT-116 cells) or when the apoptosis machinery is defective (such as Bax deficient HCT-116 cells). The CT20 peptide was also effective under conditions of effector caspase inhibition or Bcl-2 over expression. These data indicate that the CT20 peptide may be a potent killing tool in cancers with abnormal levels of anti-apoptotic proteins, as well as cancers in which other survival signaling mechanism may be irregular. FIG. 12, for example, shows a hypothetical cell death pathway for CT20p peptide using a basic model of apoptotic and non-apoptotic cell death.

Example 6. Pore Formation by CT20p Peptide

An analysis of formation of relatively large membrane pores by Bax C-terminal 20-reside peptide (CT20p) and two mutants where the two native lysines are replaced either with glutamates (charge reversal mutation) or leucines (charge neutralization mutation) were examined. The three peptides demonstrate distinct potencies to form pores in both zwitterionic and anionic membranes that transport calcein ($M_r$~623). The most efficient pores are formed by the wild-type peptide in anionic membranes. The kinetics of calcein release at various concentrations of the three peptides allowed identification of the second-order rate constants of pore formation within the membrane, the affinity constants of peptide units composing the pore, and the oligomeric pore structure. Nucleation of the pore is shown to be relatively slow and involve 2-3 peptide molecules, followed by a faster process of assembly of the pore that includes up to eight peptide molecules. Structural studies led to a model of an octameric transmembrane pore with an inner diameter of 20-22 A. Analysis of the kinetics of calcein release from lipid vesicles allows determination of rate constants of pore formation, peptide-peptide affinities within the membrane, the oligomeric state of transmembrane pores, and the role of the lysine residues.

In summary, the C-terminal 20-residue stretch of Bax has the capability of forming relatively large membrane pores with a radius of at least 13 Å. Replacement of the two lysine residues close to the C-terminus with anionic glutamate or nonpolar leucine residues reduce the pore forming activity of the peptide, but the mutant peptides are still quite capable pore formers. In general, the pore formation is a two-stage process, nucleation and assembly of the final pore structure that includes up to eight peptide molecules, and is stabilized by intermolecular interaction energies of −10 to −13 kcal/mol, which is quite significant for 20-mer peptides.

Additionally, the pore structure was analyzed by polarized Fourier transform infrared, circular dichroism, and fluorescence experiments on the peptides reconstituted in phospholipid membranes. The peptides assumed an α/β-type secondary structure within membranes. Both β- strands and a-helices are significantly tilted relative to the membrane normal, by 30-60 degrees. The tryptophan residue embed into zwitterionic membranes at 8-9 A from membrane center. Membrane anionic charge causes a deeper insertion of tryptophan for BaxC-KK and BaxC-LL but not BaxC-EE. Combined with pore stoichiometry, these data suggest a pore model where eight peptide molecules form an "α/β-ring" structure with pore inner diameter of 20-22 Å. These results identified a strong membranotropic activity of Bax C-terminus and proposed a new mechanism by which peptides can efficiently perforate cell membranes and thus be used as cytotoxic agents.

Additionally, membrane insertion of the peptide and subsequent pore formation was mediated mainly by hydrophobic rather than electrostatic interactions. In the presence of bulk water, the peptides assume an α/β-type structure, with the β-strands and α-helices significantly tilted relative to the membrane normal. Altogether, the data are consistent with an octameric "α/β-ring" structure with an internal pore diameter of at least 13 Å to 20-22 Å that can effectively transfer calcein and larger molecules. The data establish a foundation for characterization of the molecular structure of the α/β ring transmembrane pore formed by Bax-derived peptides.

Example of Killing Microbial Cells

Figure 14:
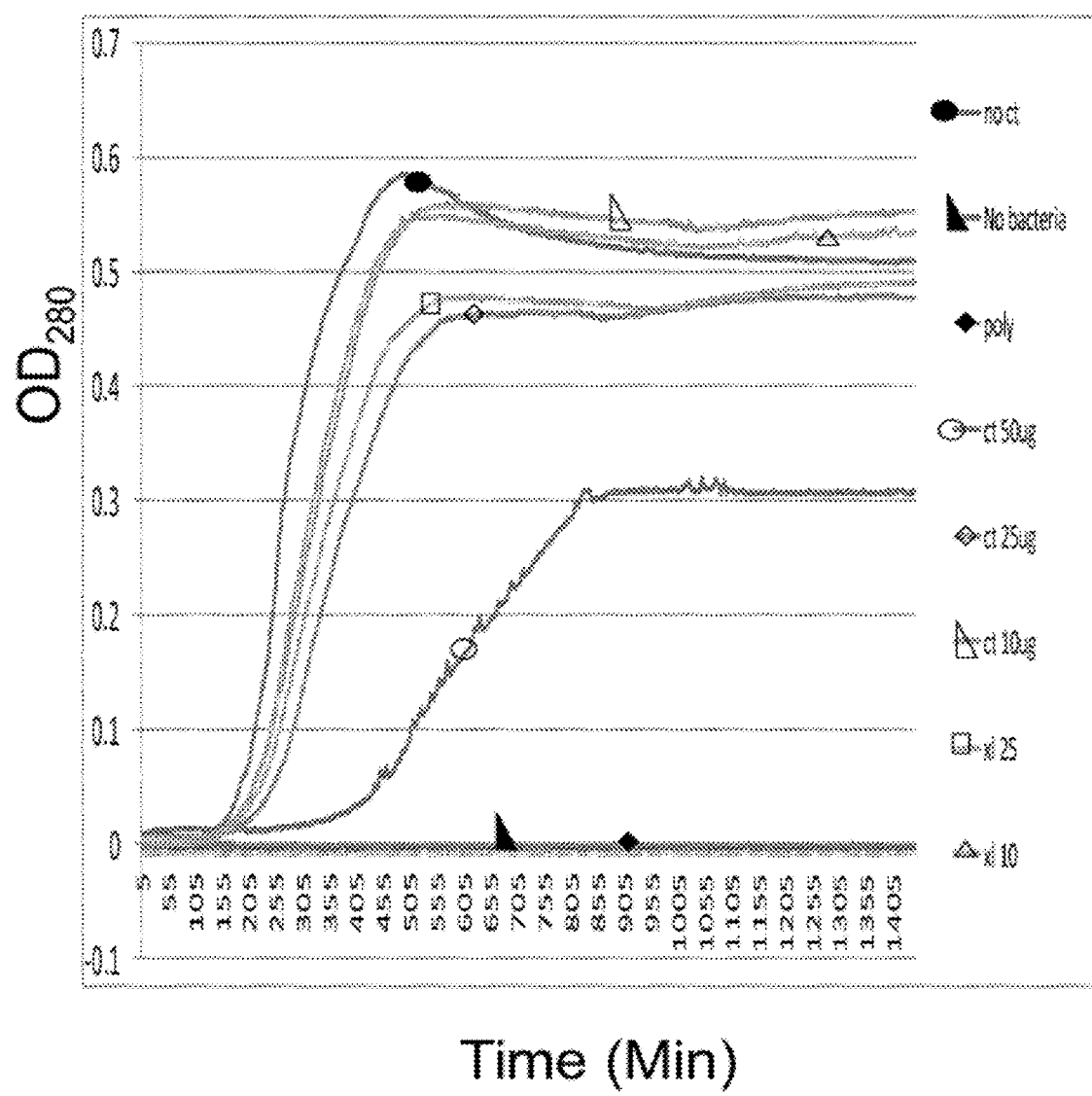
FIG. 14 shows a graph of killing of microbial cells, a measure of wild type *E. coli* growth by optical density (OD280) over 24 hours with increasing concentration of CT20p. The inhibiting concentration (IC50) was found to be 50 ug of CT20p in 100 mL LB broth.

FIG. 13 shows a comparison of CT20p peptde with antimicrobial peptides and apoptosis-inducing peptides. Attributes are shared among the peptides. FIG. 14 shows that Ct20p peptide inhibited the growth of E. coli, a gam negative bacteria, in a dose dependent manner, inhibiting 50% of the growth of bacteria at a dose of 50 μg. The inhibition of growth began around 3 hours and reached a plateau at 13 hours, see graph. These results compared to control peptide XL or no peptide, in which growth began at 3 hours and plateaued at 6-7 hours. The E. coli were grown in the presence of a peptide, concentrations of CT20p peptide or for control, SCR peptide, or no peptide for a control, in standard conditions for growing bacteria in broth media.

Figure 15:
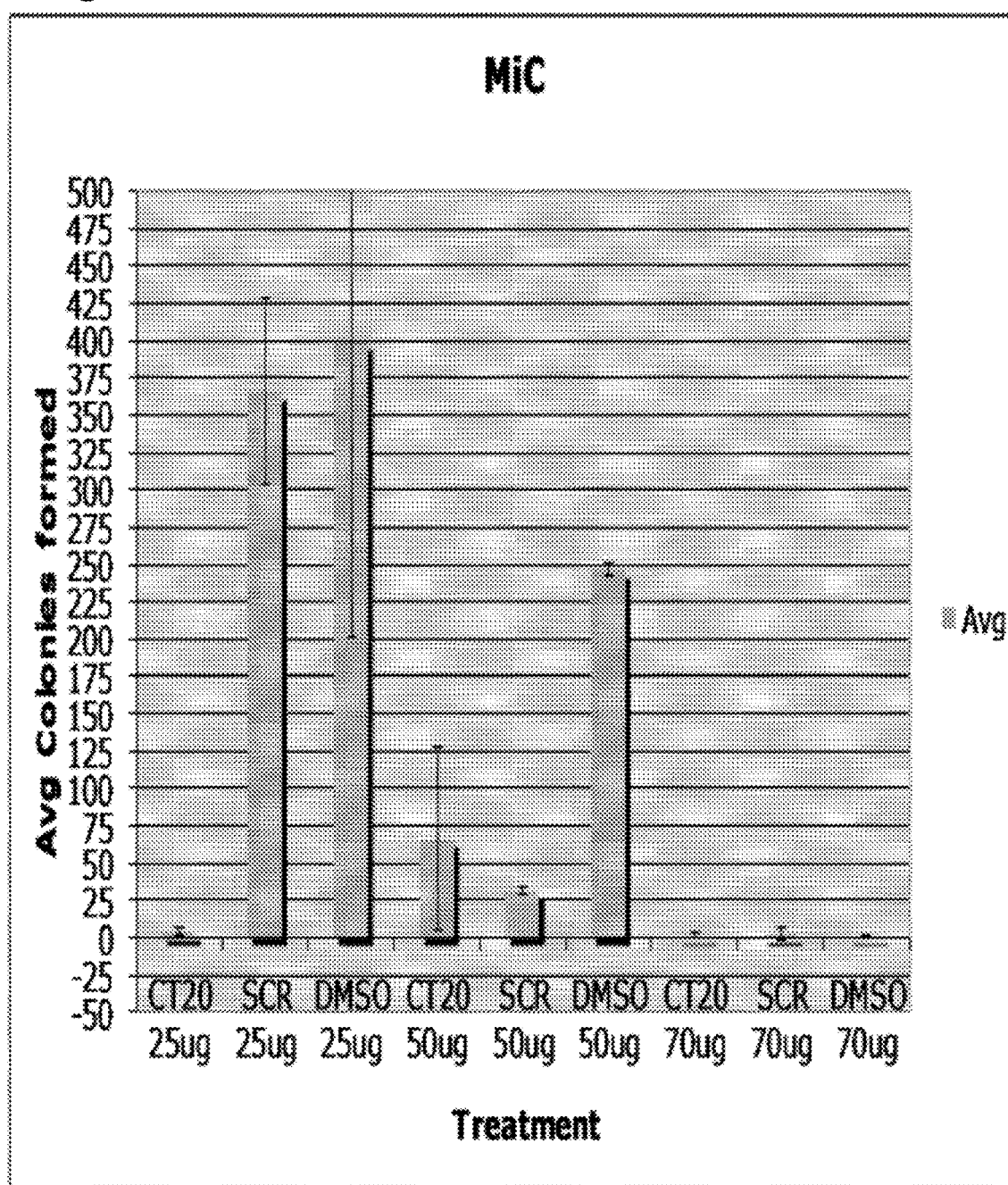
FIG. 15 shows a graph of killing microbial cells, a measure of wild type *E. coli* colony formation after treatment with both CT20p and Scrambled (SCR) peptide shows that the minimum inhibitory concentration (MiC) of the CT20p is 25 mg. This was determined by plating the *E. coli* after treatment then counting the resulting colonies after 24 hour incubation.

FIG. 15 shows counts of the bacterial colonies from the broth culture of FIG. 14. The bacterial culture media was plated after 24 hours of treatment/exposure to Ct20p or the control conditions, a peptide (SCR) or no peptide and addition of DMSO, and the resulting colonies were counted. There were few bacterial colonies detected with CT20p treatment of 24 hours, which indicated that the effects of CT20p peptide were bactericidal, not bacteriostatic (inhibition of growth). A conclusion was that the inhibition of growth seen in FIG. 14 was due to the killing or lysing of bacteria.

All of the compositions and/or methods disclosed and claimed herein can be made and executed without undue experimentation in light of the present disclosure. It will be apparent to those skilled in the art that various modifications and variations can be made in the present invention without departing from the scope or spirit of the invention.

More specifically, certain agents which are both chemically and physiologically related can be substituted for the agents described herein while the same or similar results can be achieved. All such similar substitutes and modifications apparent to those skilled in the art are deemed to be within the spirit, scope and concept of the invention as defined by the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

E. References

A. Ausili, et al. The interaction of the Bax C-terminal domain with negatively charged lipids modifies the secondary structure and changes its way of insertion into membranes, J. Struct. Biol. 164 (2008) 146.

A. J. Garcia-Saez, et al. Membrane-insertion fragments of Bcl-xL, Bax, and Bid, Biochemistry 43 (2004) 10930.

A. J. Garcia-Saez, et al. Peptides corresponding to helices 5 and 6 of Bax can independently form large lipid pores, FEBS J. 273 (2006) 971.

A. J. Garcia-Saez, et al. Peptides derived from apoptotic Bax and Bid reproduce the poration activity of the parent full-length proteins, Biophys. J. 88 (2005) 3976.

A. Nechushtan, et al. Conformation of the Bax C-terminus regulates subcellular location and cell death, EMBO J 18 (1999) 2330.

A. Schinzel, et al. Conformational control of Bax localization and apoptotic activity by Pro168, J. Cell Biol. 164 (2004) 1021.

C. Horie, et al. Characterization of signal that directs C-tail-anchored proteins to mammalian mitochondrial outer membrane, Mol. Biol. Cell 13 (2002) 1615.

D. Westphal, et al. Molecular biology of Bax and Bak activation and action, Biochim. Biophys. Acta 1813 (2011) 521.

E. Er, et al. Control of Bax homodimerization by its carboxyl terminus, J. Biol. Chem. 282 (2007) 24938.

G. Basanez, et al. Bax-type apoptotic proteins porate pure lipid bilayers through a mechanism sensitive to intrinsic monolayer curvature, J. Biol. Chem. 277 (2002) 49360.

G. V. Putcha, et al. BAX translocation is a critical event in neuronal apoptosis: regulation by neuroprotectants, BCL-2, and caspases, J. Neurosci. 19 (1999) 7476.

J. Deng, et al. BH3 profiling identifies three distinct classes of apoptotic blocks to predict response to ABT-737 and conventional chemotherapeutic agents, Cancer Cell 12 (2007) 171.

J. G. Valero, et al. Bax-derived membrane-active peptides act as potent and direct inducers of apoptosis in cancer cells, J. Cell Sci. 124 (2011) 556.

K. G. Wolter, et al. Movement of Bax from the cytosol to mitochondria during apoptosis, J Cell Biol 139 (1997) 1281.

L. Zhang, et al. Role of BAX in the apoptotic response to anticancer agents, Science 290 (2000) 989.

M. Mar Martinez-Senac, et al. Conformation of the C-terminal domain of the pro-apoptotic protein Bax and mutants and its interaction with membranes, Biochemistry 40 (2001) 9983.

M. Suzuki, et al. Structure of Bax: coregulation of dimer formation and intracellular localization, Cell 103 (2000) 645.

N. M. George, et al. Bax contains two functional mitochondrial targeting sequences and translocates to mitochondria in a conformational change- and homo-oligomerization-driven process, J. Biol. Chem. 285 (2010) 1384.

P. F. Cartron, et al. Distinct domains control the addressing and the insertion of Bax into mitochondria, J. Biol. Chem. 280 (2005) 10587.

P. F. Cartron, et al. The expression of a new variant of the pro-apoptotic molecule Bax, Baxpsi, is correlated with an increased survival of glioblastoma multiforme patients, Hum. Mol. Genet. 11 (2002) 675.

P. F. Cartron, et al. The N-terminal end of Bax contains a mitochondrial-targeting signal, J. Biol. Chem. 278 (2003) 11633.

P. H. Schlesinger, et al. The Bax pore in liposomes, Biophysics, Cell Death. Differ. 13 (2006) 1403.

R. Eskes, et al. Bax-induced cytochrome C release from mitochondria is independent of the permeability transition pore but highly dependent on Mg2+ ions, J Cell Biol 143 (1998) 217.

R. J. Boohaker, et al. BAX supports the mitochondrial network, promoting bioenergetics in nonapoptotic cells, Am. J. Physiol Cell Physiol 300 (2011) C1466-C1478.

S. Santra, et al. Aliphatic hyperbranched polyester: a new building block in the construction of multifunctional nanoparticles and nanocomposites, Langmuir 26 (2010) 5364.

T. Kaufmann, et al. Characterization of the signal that directs Bcl-x(L), but not Bcl-2, to the mitochondrial outer membrane, J. Cell Biol. 160 (2003) 53.

T. Oltersdorf, et al. An inhibitor of Bcl-2 family proteins induces regression of solid tumours, Nature 435 (2005) 677.

Z. N. Oltvai, et al. Bcl-2 heterodimerizes in vivo with a conserved homolog, Bax, that accelerates programmed cell death, Cell 74 (1993) 609.

TABLE 1

F. Sequences

| Seq ID No. | Description | Sequence |
|---|---|---|
| 1 | CT20Bax WT | VTIFVAGVLTASLTIWKKMG |
| 2 | CT20Bax EE | VTIFVAGVLTASLTIWEEMG |
| 3 | CT20Bax LL | VTIFVAGVLTASLTIWLLMG |
| 4 | CT20Bax RR | VTIFVAGVLTASLTIWRRMG |
| 5 | BAX-KK (for) | 5'-GGATCACTCTCGGCCTGGACACCATGGG GATGTACCCATACGATGTTCCAG ATTACGCTGACGGGTCCGGGGAGCAG-3' |
| 6 | BAX-KK (rev) | 5'-CGTCGACTGCAGAATTCTCAGCCCATC TTCTTCCAGATGGTGAGCGAGG-3' |
| 7 | BAX-ΔNT (1-19) (for) | 5'-CCGGGGAGCAGCCCCATATGTACCCAT ACGATGTTCCAGATTACGCTATGAAG ACAGGGGCCCTTTTGC-3' |

TABLE 1-continued

F. Sequences

| Seq ID No. | Description | Sequence |
|---|---|---|
| 8 | BAX-ΔNT (1-19) (rev) | 5'-CGTCGACTGCAGAATTCTCAGCCCATCTT CTTCCAGATGGTGAGCGAGG-3' |
| 9 | BAX-ΔCT (173-192) (for) | 5'-GGATCACTCTCGGCCTGGACACCATGG GGATGTACCCATACGATGTTCCAG ATTACGCTGACGGGTCCGGGGAGCAG-3' |
| 10 | BAX-ΔCT (173-192) (rev) | 5'-CGTCGACTGCAGAATTCTCAGGTCTGCCA CGTGGGCGTCCAAAG-3' |
| 11 | BAX-LL (for) | 5'-GGATCACTCTCGGCCTGGACACCATGG GGATGTACC CATACGA TGTTCCAG ATTACGCTGACGGGTCCGGGGAGCAG-3' |
| 12 | BAX-LL (rev) | 5'-CGTCGACTGCAGAATTCTCAGCCCATGA GGAGCCAGATGGTGAGCGAGG-3' |
| 13 | BAX-DD (for) | 5'-GGATCACTCTCGGCCTGGACACCATG GGGATGTACCCATACGATGTTCCAG ATTACGCTGACGGGTCCGGGGAGCAG-3' |
| 14 | BAX-DD (rev) | 5'-CGTCGACTGCAGAATTCTC AGCCCATGTCGTCCCAGATGGTGAGCGAGG-3' |
| 15 | BAX-EE (for) | 5'-GGATCACTCTCGGCCTGGACACCATGGG GATGTACCCATACGATGTTCCAG ATTACGCTGACGGGTCCGGGGAGCAG-3' |
| 16 | BAX-EE (rev) | 5'-CGTCGACTGCAGAATTCTCAGCCC ATCTCCTCCCAGATGGTGAGCGAGG-3' |
| 17 | BAX-RR (for) | 5'-GGATCACTCTCGGCCTGGACACCATG GGGATGTACCCATACGATGTTCCAG ATTACGCTGACGGGTCCGGGGAGCAG-3' |
| 18 | BAX-RR (rev) | 5'-CGTCGATCTCAGCCCATTCGTCGCC ACATGGTGAGCGAGG-3' |
| 19 | BAX-QQ (for) | 5'-GGATCACTCTCGGCCTGGACACCAT GGGGATGTACCCATACGATGTTCCAG ATTACGCTGACGGGTCCGGGGAGCAG-3' |
| 20 | BAX-QQ (rev) | 5'-CGTCGACTGCAGAATTC TCAGCCCATC TGCTGCCAGATGGTGAGCGAGG-3' |
| 21 | BAX-KMGK (for) | 5'-GGATCACTCTCGGCCTGGACACCATG GGGATGTACCCATACGATGTTCCAG ATTACGCTGACGGGTCCGGGGAGCAG-3' |
| 22 | BAX-KMGK (rev) | 5'-CGTCGACTGCAGAATTCTCACTTCCCCA TCTTCCAGATGGTG AGCGAGG-3' |
| 23 | BAX-EK (for) | 5'-GGATCACTCTCGGCCTGGACACCATG GGGATGTACCCATACGATGTTCCAG ATTACGCTGACGGGTCCGGGGAGCAG-3' |
| 24 | BAX-EK (rev) | 5'-CGTCGACTGCAGAATTCTCAGCCCA TCTTCTCCCAGATGGTGAGCGAGG-3' |
| 25 | GFP-CT-WT (for) | 5'-GGATCACTCTCGGCCTGGACGA GGATATCATGGTGAGCAAG-3' |
| 26 | GFP-CT-WT (rev) | 5'-CGTCGACTGCAGATATCTCAGCCCA TCTTCTTCCAGATGGTGAGCGAGG CGGTGAGCACTCCCGCCACAAAGATG GTCACGGTGTTATCTAGATC-3' |
| 27 | GFP-CT-EE (for) | 5'-GGATCACTCTCGGCCTGGACGA GGATATCATGGTGAGCAAG-3' |
| 28 | GFP-CT-EE (rev) | 5'-CGTCGACTGCAGATATCTCAGCCCATC TCCTCCCAGATGGTGAGCGAGGC GGTGAGCACTCCCGCCACAAAGATGG TCACGGTGTTATCTAGATC-3' |

TABLE 1-continued

F. Sequences

| Seq ID No. | Description | Sequence |
|---|---|---|
| 29 | GFP-CT-RR (for) | 5'-GGATCACTCTCGGCCTGGACGAGGATATCATGGTGAGCAAG-3' |
| 30 | GFP-CT-RR (rev) | 5'-CGTCGACTGCAGATATCTCAGCCCATGAGGAGCCAGATGGTGAGCGAGGCGGTGAGCACTCCCGCCACAAAGATGGTCACGGTGTTATCTAGATC-3' |
| 31 | DD-CT-WT (for) | 5'-AATTCTGTGACCATCTTTGTGGCGGGAGTGCTCACCGCCTCGCTCACCATCTGGAAGAAGATGGGCTGA-3' |
| 32 | DD-CT-WT (rev) | 5'-GATCTCAGCCCATCTTCTTCCAGATGGTGAGCGAGGCGGTGAGCACTCCCGCCACAAAGATGGTCACAG-3' |
| 33 | DD-CT-EE (for) | 5'-AATTCTGTGACCATCTTTGTGGCGGGAGTGCTCACCGCCTCGCTCACCATCTGGGAGGAGATGGGCTGA-3' |
| 34 | DD-CT-EE (rev) | 5'-GATCTCAGCCCATCTCCTCCCAGATGGTGAGCGAGGCGGTGAGCACTCCCGCCACAAAGATGGTCACAG-3' |
| 35 | DD-CT-LL (for) | 5'-AATTCTGTGACCATCTTTGTGGCGGGAGTGCTCACCGCCTCGCTCACCATCTGGCTCCTCATGGGCTGA-3' |
| 36 | DD-CT-LL (rev) | 5'-GATCTCAGCCCATGAGGAGCCAGATGGTGAGCGAGGCGGTGAGCACTCCCGCCACAAA GATGGTCACAG-3' |
| 37 | DD-CT-RR (for) | 5'-AATTCTGTGACCATCTTTGTGGCGGGAGTGCTCACCGCCTCGCTCACCATCTGGCGACGAATGGGCTGA-3' |
| 38 | DD-CT-RR (rev) | 5-GATCTCAGCCCATTCGTCGCCAGATGGTGAGCGAGGCGGTGAGCACTCCCGCCACAAA GATGGTCACAG-3' |

---

What is claimed is:

1. A method for treating cancer in a subject in need thereof, comprising administering to the subject a therapeutically effective amount of a composition comprising a C-terminal B cell lymphoma-2 (Bcl-2)-associated X protein (Bax) peptide (CT20p peptide) and a pharmaceutically acceptable carrier, wherein the CT20p peptide consists of the amino acid sequence of SEQ ID NO: 1, SEQ ID NO: 2, SEQ ID NO: 3, or SEQ ID NO: 4; and wherein the cancer is selected from the group consisting of breast cancer, colorectal cancer, lung cancer, and liver cancer.

2. The method of claim 1, further comprising administering to the subject an anti-cancer drug.

3. The method of claim 2, further comprising administering to the subject a chemotherapeutic drug.

4. The method of claim 2, further comprising administering to the subject a radiosensitizer.

5. The method of claim 1, wherein the CT20p peptide is administered directly into the cancer.

6. The method of claim 1, further comprising repeating the administration of the therapeutically effective amount of the composition comprising the CT20p peptide and the pharmaceutically acceptable carrier.

7. The method of claim 1, wherein the CT20p peptide is encapsulated in a nanoparticle.

8. The method of claim 7, wherein the nanoparticle is aminated.

9. The method of claim 7, wherein the nanoparticle is carboxylated.

10. The method of claim 7, wherein the nanoparticle is a polymeric nanoparticle.

11. The method of claim 10, wherein the polymeric nanoparticle is a hyperbranched polymeric (HBPE) nanoparticle.

* * * * *

SEQUENCE LISTING

<160> NUMBER OF SEQ ID NOS: 64

<210> SEQ ID NO 1
<211> LENGTH: 20
<212> TYPE: PRT
<213> ORGANISM: Homo sapiens

<400> SEQUENCE: 1

Val Thr Ile Phe Val Ala Gly Val Leu Thr Ala Ser Leu Thr Ile Trp
1               5                   10                  15

Lys Lys Met Gly
            20

<210> SEQ ID NO 2
<211> LENGTH: 20
<212> TYPE: PRT
<213> ORGANISM: Artificial Sequence
<220> FEATURE:
<223> OTHER INFORMATION: Description of artificial sequence note = synthetic construct

<400> SEQUENCE: 2

Val Thr Ile Phe Val Ala Gly Val Leu Thr Ala Ser Leu Thr Ile Trp
1               5                   10                  15

Glu Glu Met Gly
        20

<210> SEQ ID NO 3
<211> LENGTH: 20
<212> TYPE: PRT
<213> ORGANISM: Artificial Sequence
<220> FEATURE:
<223> OTHER INFORMATION: Description of artificial sequence note =
      synthetic construct

<400> SEQUENCE: 3

Val Thr Ile Phe Val Ala Gly Val Leu Thr Ala Ser Leu Thr Ile Trp
1               5                   10                  15

Leu Leu Met Gly
        20

<210> SEQ ID NO 4
<211> LENGTH: 20
<212> TYPE: PRT
<213> ORGANISM: Artificial Sequence
<220> FEATURE:
<223> OTHER INFORMATION: Description of artificial sequence note =
      synthetic construct

<400> SEQUENCE: 4

Val Thr Ile Phe Val Ala Gly Val Leu Thr Ala Ser Leu Thr Ile Trp
1               5                   10                  15

Arg Arg Met Gly
        20

<210> SEQ ID NO 5
<211> LENGTH: 77
<212> TYPE: DNA
<213> ORGANISM: Artificial Sequence
<220> FEATURE:
<223> OTHER INFORMATION: Description of artificial sequence note =
      synthetic construct

<400> SEQUENCE: 5
ggatcactct cggcctggac accatgggga tgtacccata cgatgttcca gattacgctg     60
acgggtccgg ggagcag                                                   77

<210> SEQ ID NO 6
<211> LENGTH: 49
<212> TYPE: DNA
<213> ORGANISM: Artificial Sequence
<220> FEATURE:
<223> OTHER INFORMATION: Description of artificial sequence note =
      synthetic construct

<400> SEQUENCE: 6
cgtcgactgc agaattctca gcccatcttc ttccagatgg tgagcgagg                49

<210> SEQ ID NO 7
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 7
ccggggagca gccccatatg tacccatacg atgttccaga ttacgctatg aagacagggg     60
cccttttgc                                                            69

<210> SEQ ID NO 8
<211> LENGTH: 49
<212> TYPE: DNA
<213> ORGANISM: Artificial Sequence
<220> FEATURE:
<223> OTHER INFORMATION: Description of artificial sequence note =
      synthetic construct

<400> SEQUENCE: 8
cgtcgactgc agaattctca gcccatcttc ttccagatgg tgagcgagg            49

<210> SEQ ID NO 9
<211> LENGTH: 77
<212> TYPE: DNA
<213> ORGANISM: Artificial Sequence
<220> FEATURE:
<223> OTHER INFORMATION: Description of artificial sequence note =
      synthetic construct

<400> SEQUENCE: 9
ggatcactct cggcctggac accatgggga tgtacccata cgatgttcca gattacgctg    60
acgggtccgg ggagcag                                                  77

<210> SEQ ID NO 10
<211> LENGTH: 44
<212> TYPE: DNA
<213> ORGANISM: Artificial Sequence
<220> FEATURE:
<223> OTHER INFORMATION: Description of artificial sequence note =
      synthetic construct

<400> SEQUENCE: 10
cgtcgactgc agaattctca ggtctgccac gtgggcgtcc aaag                 44

<210> SEQ ID NO 11
<211> LENGTH: 77
<212> TYPE: DNA
<213> ORGANISM: Artificial Sequence
<220> FEATURE:
<223> OTHER INFORMATION: Description of artificial sequence note =
      synthetic construct

<400> SEQUENCE: 11
ggatcactct cggcctggac accatgggga tgtacccata cgatgttcca gattacgctg    60
acgggtccgg ggagcag                                                  77

<210> SEQ ID NO 12
<211> LENGTH: 49
<212> TYPE: DNA
<213> ORGANISM: Artificial Sequence
<220> FEATURE:
<223> OTHER INFORMATION: Description of artificial sequence note =
      synthetic construct

<400> SEQUENCE: 12
cgtcgactgc agaattctca gcccatgagg agccagatgg tgagcgagg            49

<210> SEQ ID NO 13
<211> LENGTH: 77
<212> TYPE: DNA
<213> ORGANISM: Artificial Sequence
<220> FEATURE:
<223> OTHER INFORMATION: Description of artificial sequence note =
      synthetic construct

<400> SEQUENCE: 13
ggatcactct cggcctggac accatgggga tgtacccata cgatgttcca gattacgctg    60
acgggtccgg ggagcag    77

<210> SEQ ID NO 14
<211> LENGTH: 49
<212> TYPE: DNA
<213> ORGANISM: Artificial Sequence
<220> FEATURE:
<223> OTHER INFORMATION: Description of artificial sequence note =
      synthetic construct

<400> SEQUENCE: 14
cgtcgactgc agaattctca gcccatgtcg tcccagatgg tgagcgagg    49

<210> SEQ ID NO 15
<211> LENGTH: 77
<212> TYPE: DNA
<213> ORGANISM: Artificial Sequence
<220> FEATURE:
<223> OTHER INFORMATION: Description of artificial sequence note =
      synthetic construct

<400> SEQUENCE: 15
ggatcactct cggcctggac accatgggga tgtacccata cgatgttcca gattacgctg    60
acgggtccgg ggagcag    77

<210> SEQ ID NO 16
<211> LENGTH: 49
<212> TYPE: DNA
<213> ORGANISM: Artificial Sequence
<220> FEATURE:
<223> OTHER INFORMATION: Description of artificial sequence note =
      synthetic construct

<400> SEQUENCE: 16
cgtcgactgc agaattctca gcccatctcc tcccagatgg tgagcgagg    49

<210> SEQ ID NO 17
<211> LENGTH: 77
<212> TYPE: DNA
<213> ORGANISM: Artificial Sequence
<220> FEATURE:
<223> OTHER INFORMATION: Description of artificial sequence note =
      synthetic construct

<400> SEQUENCE: 17
ggatcactct cggcctggac accatgggga tgtacccata cgatgttcca gattacgctg    60
acgggtccgg ggagcag    77

<210> SEQ ID NO 18
<211> LENGTH: 40
<212> TYPE: DNA
<213> ORGANISM: Artificial Sequence
<220> FEATURE:
<223> OTHER INFORMATION: Description of artificial sequence note =
      synthetic construct

<400> SEQUENCE: 18
cgtcgatctc agcccattcg tcgccacatg gtgagcgagg    40

<210> SEQ ID NO 19
<211> LENGTH: 77
<212> TYPE: DNA

<213> ORGANISM: Artificial Sequence
<220> FEATURE:
<223> OTHER INFORMATION: Description of artificial sequence note = synthetic construct

<400> SEQUENCE: 19
ggatcactct cggcctggac accatgggga tgtacccata cgatgttcca gattacgctg    60
acgggtccgg ggagcag                                                    77

<210> SEQ ID NO 20
<211> LENGTH: 49
<212> TYPE: DNA
<213> ORGANISM: Artificial Sequence
<220> FEATURE:
<223> OTHER INFORMATION: Description of artificial sequence note = synthetic construct

<400> SEQUENCE: 20
cgtcgactgc agaattctca gcccatctgc tgccagatgg tgagcgagg    49

<210> SEQ ID NO 21
<211> LENGTH: 77
<212> TYPE: DNA
<213> ORGANISM: Artificial Sequence
<220> FEATURE:
<223> OTHER INFORMATION: Description of artificial sequence note = synthetic construct

<400> SEQUENCE: 21
ggatcactct cggcctggac accatgggga tgtacccata cgatgttcca gattacgctg    60
acgggtccgg ggagcag                                                    77

<210> SEQ ID NO 22
<211> LENGTH: 49
<212> TYPE: DNA
<213> ORGANISM: Artificial Sequence
<220> FEATURE:
<223> OTHER INFORMATION: Description of artificial sequence note = synthetic construct

<400> SEQUENCE: 22
cgtcgactgc agaattctca cttccccatc ttccagatgg tgagcgagg    49

<210> SEQ ID NO 23
<211> LENGTH: 77
<212> TYPE: DNA
<213> ORGANISM: Artificial Sequence
<220> FEATURE:
<223> OTHER INFORMATION: Description of artificial sequence note = synthetic construct

<400> SEQUENCE: 23
ggatcactct cggcctggac accatgggga tgtacccata cgatgttcca gattacgctg    60
acgggtccgg ggagcag                                                    77

<210> SEQ ID NO 24
<211> LENGTH: 49
<212> TYPE: DNA
<213> ORGANISM: Artificial Sequence
<220> FEATURE:
<223> OTHER INFORMATION: Description of artificial sequence note = synthetic construct

<400> SEQUENCE: 24
cgtcgactgc agaattctca gcccatcttc tcccagatgg tgagcgagg    49

<210> SEQ ID NO 25
<211> LENGTH: 41
<212> TYPE: DNA
<213> ORGANISM: Artificial Sequence
<220> FEATURE:
<223> OTHER INFORMATION: Description of artificial sequence note =
      synthetic construct

<400> SEQUENCE: 25
ggatcactct cggcctggac gaggatatca tggtgagcaa g                 41

<210> SEQ ID NO 26
<211> LENGTH: 95
<212> TYPE: DNA
<213> ORGANISM: Artificial Sequence
<220> FEATURE:
<223> OTHER INFORMATION: Description of artificial sequence note =
      synthetic construct

<400> SEQUENCE: 26
cgtcgactgc agatatctca gcccatcttc ttccagatgg tgagcgaggc ggtgagcact    60
cccgccacaa agatggtcac ggtgttatct agatc                              95

<210> SEQ ID NO 27
<211> LENGTH: 41
<212> TYPE: DNA
<213> ORGANISM: Artificial Sequence
<220> FEATURE:
<223> OTHER INFORMATION: Description of artificial sequence note =
      synthetic construct

<400> SEQUENCE: 27
ggatcactct cggcctggac gaggatatca tggtgagcaa g                 41

<210> SEQ ID NO 28
<211> LENGTH: 95
<212> TYPE: DNA
<213> ORGANISM: Artificial Sequence
<220> FEATURE:
<223> OTHER INFORMATION: Description of artificial sequence note =
      synthetic construct

<400> SEQUENCE: 28
cgtcgactgc agatatctca gcccatctcc tcccagatgg tgagcgaggc ggtgagcact    60
cccgccacaa agatggtcac ggtgttatct agatc                              95

<210> SEQ ID NO 29
<211> LENGTH: 41
<212> TYPE: DNA
<213> ORGANISM: Artificial Sequence
<220> FEATURE:
<223> OTHER INFORMATION: Description of artificial sequence note =
      synthetic construct

<400> SEQUENCE: 29
ggatcactct cggcctggac gaggatatca tggtgagcaa g                 41

<210> SEQ ID NO 30
<211> LENGTH: 95
<212> TYPE: DNA
<213> ORGANISM: Artificial Sequence
<220> FEATURE:
<223> OTHER INFORMATION: Description of artificial sequence note =
      synthetic construct

<400> SEQUENCE: 30
cgtcgactgc agatatctca gcccatgagg agccagatgg tgagcgaggc ggtgagcact      60
cccgccacaa agatggtcac ggtgttatct agatc                                 95

<210> SEQ ID NO 31
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 31
aattctgtga ccatctttgt ggcgggagtg ctcaccgcct cgctcaccat ctggaagaag      60
atgggctga                                                              69

<210> SEQ ID NO 32
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 32
gatctcagcc catcttcttc cagatggtga gcgaggcggt gagcactccc gccacaaaga      60
tggtcacag                                                              69

<210> SEQ ID NO 33
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 33
aattctgtga ccatctttgt ggcgggagtg ctcaccgcct cgctcaccat ctgggaggag      60
atgggctga                                                              69

<210> SEQ ID NO 34
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 34
gatctcagcc catctcctcc cagatggtga gcgaggcggt gagcactccc gccacaaaga      60
tggtcacag                                                              69

<210> SEQ ID NO 35
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 35
aattctgtga ccatctttgt ggcgggagtg ctcaccgcct cgctcaccat ctggctcctc      60

```
atgggctga                                                              69

<210> SEQ ID NO 36
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 36
gatctcagcc catgaggagc cagatggtga gcgaggcggt gagcactccc gccacaaaga      60
tggtcacag                                                              69

<210> SEQ ID NO 37
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 37
aattctgtga ccatctttgt ggcgggagtg ctcaccgcct cgctcaccat ctggcgacga      60
atgggctga                                                              69

<210> SEQ ID NO 38
<211> LENGTH: 69
<212> TYPE: DNA
<213> ORGANISM: Artificial Sequence
<220> FEATURE:
<223> OTHER INFORMATION: Description of artificial sequence note =
      synthetic construct

<400> SEQUENCE: 38
gatctcagcc cattcgtcgc cagatggtga gcgaggcggt gagcactccc gccacaaaga      60
tggtcacag                                                              69

<210> SEQ ID NO 39
<211> LENGTH: 25
<212> TYPE: PRT
<213> ORGANISM: Bos taurus

<400> SEQUENCE: 39

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 40
<211> LENGTH: 13
<212> TYPE: PRT
<213> ORGANISM: Bos taurus

<400> SEQUENCE: 40

Ile Leu Pro Trp Lys Trp Pro Trp Trp Pro Trp Arg Arg
1               5                   10

<210> SEQ ID NO 41
<211> LENGTH: 26
<212> TYPE: PRT
<213> ORGANISM: Apis mellifera

<400> SEQUENCE: 41
```

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 42
<211> LENGTH: 24
<212> TYPE: PRT
<213> ORGANISM: Rana acanthi

<400> SEQUENCE: 42

Phe Leu Pro Val Leu Ala Gly Ile Ala Ala Lys Val Val Pro Ala Leu
1               5                   10                  15

Phe Cys Lys Ile Thr Lys Lys Cys
            20

<210> SEQ ID NO 43
<211> LENGTH: 20
<212> TYPE: PRT
<213> ORGANISM: Rana acanthi

<400> SEQUENCE: 43

Phe Leu Gly Gly Leu Ile Lys Ile Val Pro Ala Met Ile Cys Ala Val
1               5                   10                  15

Thr Lys Lys Cys
            20

<210> SEQ ID NO 44
<211> LENGTH: 37
<212> TYPE: PRT
<213> ORGANISM: Trigoniopthalmus alternatus

<400> SEQUENCE: 44

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 45
<211> LENGTH: 34
<212> TYPE: PRT
<213> ORGANISM: Rana acanthi

<400> SEQUENCE: 45

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 46
<211> LENGTH: 23
<212> TYPE: PRT
<213> ORGANISM: Rana acanthi

<400> SEQUENCE: 46

Gly Ile Gly Lys Phe Leu His Ser Ala Lys Lys Phe Gly Lys Ala Phe
1               5                   10                  15
```

Val Gly Glu Ile Met Asn Ser
            20

<210> SEQ ID NO 47
<211> LENGTH: 20
<212> TYPE: PRT
<213> ORGANISM: Artificial Sequence
<220> FEATURE:
<223> OTHER INFORMATION: synthetic construct; CT20p REV peptide

<400> SEQUENCE: 47

Gly Met Lys Lys Trp Ile Thr Leu Ser Ala Thr Leu Val Gly Ala Val
1               5                   10                  15

Phe Thr Ile Val
            20

<210> SEQ ID NO 48
<211> LENGTH: 14
<212> TYPE: PRT
<213> ORGANISM: Artificial Sequence
<220> FEATURE:
<223> OTHER INFORMATION: synthetic construct; KLA peptide

<400> SEQUENCE: 48

Lys Leu Ala Lys Leu Ala Lys Lys Leu Ala Lys Leu Ala Lys
1               5                   10

<210> SEQ ID NO 49
<211> LENGTH: 29
<212> TYPE: PRT
<213> ORGANISM: Homo sapiens

<400> SEQUENCE: 49

Asp Gly Asn Phe Asn Trp Gly Arg Val Val Ala Leu Phe Tyr Phe Ala
1               5                   10                  15

Ser Lys Leu Val Leu Lys Val Pro Glu Leu Ile Arg Thr
            20                  25

<210> SEQ ID NO 50
<211> LENGTH: 20
<212> TYPE: PRT
<213> ORGANISM: Homo sapiens

<400> SEQUENCE: 50

Met Arg Pro Glu Ile Trp Ile Ala Gln Glu Leu Arg Arg Ile Gly Asp
1               5                   10                  15

Glu Phe Asn Ala
            20

<210> SEQ ID NO 51
<211> LENGTH: 20
<212> TYPE: PRT
<213> ORGANISM: Homo sapiens

<400> SEQUENCE: 51

Glu Asp Ile Ile Arg Asn Ile Ala Arg His Leu Ala Gln Val Gly Asp
1               5                   10                  15

Ser Met Asp Arg
            20

<210> SEQ ID NO 52
<211> LENGTH: 16
<212> TYPE: PRT
<213> ORGANISM: Homo sapiens

<400> SEQUENCE: 52

Gly Gln Val Gly Arg Gln Leu Ala Ile Ile Gly Asp Asp Ile Asn Arg
1               5                   10                  15

<210> SEQ ID NO 53
<211> LENGTH: 20
<212> TYPE: PRT
<213> ORGANISM: Artificial Sequence
<220> FEATURE:
<223> OTHER INFORMATION: synthetic construct; CT20p peptide
<220> FEATURE:
<221> NAME/KEY: MOD_RES
<222> LOCATION: (1)..(1)
<223> OTHER INFORMATION: ACETYLATION

<400> SEQUENCE: 53

Val Ile Thr Phe Val Ala Gly Val Leu Thr Ala Ser Leu Thr Ile Trp
1               5                   10                  15

Lys Lys Met Gly
            20

<210> SEQ ID NO 54
<211> LENGTH: 4
<212> TYPE: PRT
<213> ORGANISM: Artificial Sequence
<220> FEATURE:
<223> OTHER INFORMATION: synthetic construct; Bax intracellular
      localization peptide

<400> SEQUENCE: 54

Lys Lys Met Gly
1

<210> SEQ ID NO 55
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 55

Leu Lys Met Gly
1

<210> SEQ ID NO 56
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 56

Lys Leu Met Gly
1

<210> SEQ ID NO 57
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 57

Leu Leu Met Gly
1

<210> SEQ ID NO 58
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 58

Glu Lys Met Gly
1

<210> SEQ ID NO 59
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 59

Lys Glu Met Lys
1

<210> SEQ ID NO 60
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 60

Glu Glu Met Gly
1

<210> SEQ ID NO 61
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 61

Gln Gln Met Gly
1

<210> SEQ ID NO 62
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 62

Asp Asp Met Gly
1

<210> SEQ ID NO 63
<211> LENGTH: 4
<212> TYPE: PRT
<213> ORGANISM: Artificial Sequence
<220> FEATURE:

```
<223> OTHER INFORMATION: synthetic construct; mutant Bax intracellular
      localization peptide

<400> SEQUENCE: 63

Arg Arg Met Gly
1

<210> SEQ ID NO 64
<211> LENGTH: 4
<212> TYPE: PRT
<213> ORGANISM: Artificial Sequence
<220> FEATURE:
<223> OTHER INFORMATION: synthetic construct; mutant Bax intracellular
      localization peptide

<400> SEQUENCE: 64

Lys Met Gly Lys
1
```